(12) United States Patent
Chan et al.

(10) Patent No.: US 9,035,132 B2
(45) Date of Patent: May 19, 2015

(54) **MODIFIED *HELIANTHUS ANNUUS* TRANSCRIPTION FACTOR IMPROVES YIELD**

(71) Applicants: Lia Raquel Chan, Santa Fe (AR); Daniel Hector Gonzalez, Santa Fe (AR)

(72) Inventors: Lia Raquel Chan, Santa Fe (AR); Daniel Hector Gonzalez, Santa Fe (AR)

(*) Notice: Subject to any disclaimer, the term of this patent is extended or adjusted under 35 U.S.C. 154(b) by 283 days.

(21) Appl. No.: 13/771,989

(22) Filed: Feb. 20, 2013

(65) Prior Publication Data

US 2013/0263327 A1 Oct. 3, 2013

Related U.S. Application Data

(60) Provisional application No. 61/601,335, filed on Feb. 21, 2012.

(51) Int. Cl.
*C12N 15/82* (2006.01)
*C07K 14/415* (2006.01)

(52) U.S. Cl.
CPC .......... *C12N 15/8261* (2013.01); *C07K 14/415* (2013.01); *C12N 15/8273* (2013.01); *C12N 15/8269* (2013.01)

(58) Field of Classification Search
None
See application file for complete search history.

(56) References Cited

U.S. PATENT DOCUMENTS

| | | | |
|---|---|---|---|
| 5,981,729 A | 11/1999 | Chun et al. | |
| 6,265,638 B1 | 7/2001 | Bidney et al. | |
| 7,674,955 B2 | 3/2010 | Chan et al. | |
| 8,283,521 B2 | 10/2012 | Chan et al. | |
| 2008/0148432 A1 | 6/2008 | Abad | |
| 2010/0192252 A1 | 7/2010 | Chan et al. | |
| 2011/0277190 A1 | 11/2011 | Abad | |

FOREIGN PATENT DOCUMENTS

WO   WO 01/77311 A2   10/2001

OTHER PUBLICATIONS

Arce, A.L., et al., "Patents on Plant Transcription Factors," *Recent Patents on Biotechnology* 2:209-217, Bentham Science Publishers Ltd., Netherlands (2008).
Arce, A.L., et al., "Uncharacterized conversed motifs outside the HD-Zip domain in HD-Zip subfamily I transcription factors; a potential source of functional diversity," *BMC Plant Biology* 11:42, BioMed Central Ltd., England (2011).
Ariel, F., et al., "Environmental Regulation of Lateral Root Emergence in *Medicago truncatula* Requires the HD-Zip I Transcription," *The Plant Cell* 22:2171-2183, American Society of Plant Biologists, United States (Jul. 2010).
Ariel, F.D., et al., "The true story of the HD-Zip family," *TRENDS in Plant Science* 12(9):419-426, Elsevier Ltd., England (2007).
Benfey, P.N., et al., "The CaMV 35S enhancer contains at least two domains which can confer different developmental and tissue-specific expression patterns," *The EMBO Journal* 8(8):2195-2202, IRL Press, England (1989).
Benfey, P.N. and Chua, N-H., "The Cauliflower Mosaic Virus 35S Promoter: Combinatorial Regulation of Transcription in Plants," *Science* 250(4983):959-966, American Association for the Advancement of Science, United States (1990).
Brandle, J.E., et al., "Leaf ESTs from *Stevia rebaudiana*: A resource for gene discovery in diterpene synthesis," Plant Physiol. 2001, (GenBank Accession No. BG522661, entered Nov. 16, 2001), 2 pgs.
Bray, E.A., "Molecular Responses to Water Deficit," *Plant Physiol.* 103:1035-1040, American Society of Plant Physiologists, United States (1993).
Bray, E.A., "Plant Responses to Water Deficit," *Trends Plant Sci.* 2:48-54, Elsevier Science, Ltd., England (1997).
Cabello, J.V., et al., "The homologous HD-Zip I transcription factors HaHB1 and AtHB13 confer cold tolerance via the induction of pathogenesis-related and glucanase proteins," *The Plant Journal* 69:141-153, Blackwell Publishing Ltd, England (2011).
Cabello, J.V., et al., "The homologous homeodomain-leucine zipper transcription factors HaHB1 and AtHB13 confer tolerance to drought and salinity stresses via the induction of proteins that stabilize membranes," *Plant Biotechnology Journal* 10:815-825, Blackwell Publishing Ltd., England (2012).
Cabello, J.V., et al., "The intron of the *Arabidopsis thaliana COX5c* gene is able to improve the drought tolerance conferred by the sunflower *Hahb*-4 transcription factor," *Planta* 226:1143-1154, Springer-Verlag, Germany (2007).
Carabelli, M., et al., "The *Arabidopsis Athb-2* and -4 genes are strongly induced by far-red-rich light," *Plant J.* 4:469-479, Blackwell Scientific Publishers, England (1993).
Century, K., et al., "Regulating the Regulators: The Future Prospects for Transcription-Factor-Based Agricultural Biotechnology Products," *Plant Physiol.* 147:20-29, American Society of Plant Physiologists, United States (2008).
Chan, R.L. and Gonzalez, D.H., "A cDNA Encoding an HD-Zip Protein from Sunflower," *Plant Physiology* 106:1687-1688, American Society of Plant Physiologists, United States (1994).
Chan, R.L., et al., "Homeoboxes in plant development," *Biochim. Biophys. Acta.* 1442:1-19, Elsevier Science B.V., Netherlands (1998).
Chan, R.L., "The use of sunflower transcription factors as biotechnological tools to improve yield and stress tolerance in crops," *Phyton* 78:5-10, Instituto de Agrobiotecnologia del Litoral (IAL), Universidad Nacional del Litoral, Argentina (2009).
Dezar, C.A., et al., "*Hahb-4*, a sunflower homeobox-leucine zipper gene, is a developmental regulator and confers drought tolerance to *Arabidopsis thaliana* plants," *Transgenic Research* 14:429-440, Springer, Germany (2005).

(Continued)

*Primary Examiner* — Medina A Ibrahim
*Assistant Examiner* — Russell Boggs

(57) ABSTRACT

The invention relates to polynucleotides encoding a modified HaHB4 transcription factor and polynucleotides encoding functionally active fragments and variants of a modified HaHB4 transcription factor as well as vectors and host cells containing these polynucleotides and the polypeptides encoded by these polynucleotides. The invention also encompasses transgenic host cells, plants, seed, pollen, and plant parts containing the polypeptides and/or polynucleotides of the invention. The invention further encompasses methods of producing transgenic host cells, plants, seed, pollen, and plant parts and the processed plant products produced from these transgenic hosts.

30 Claims, 13 Drawing Sheets

(56) References Cited

OTHER PUBLICATIONS

Figure 1B:
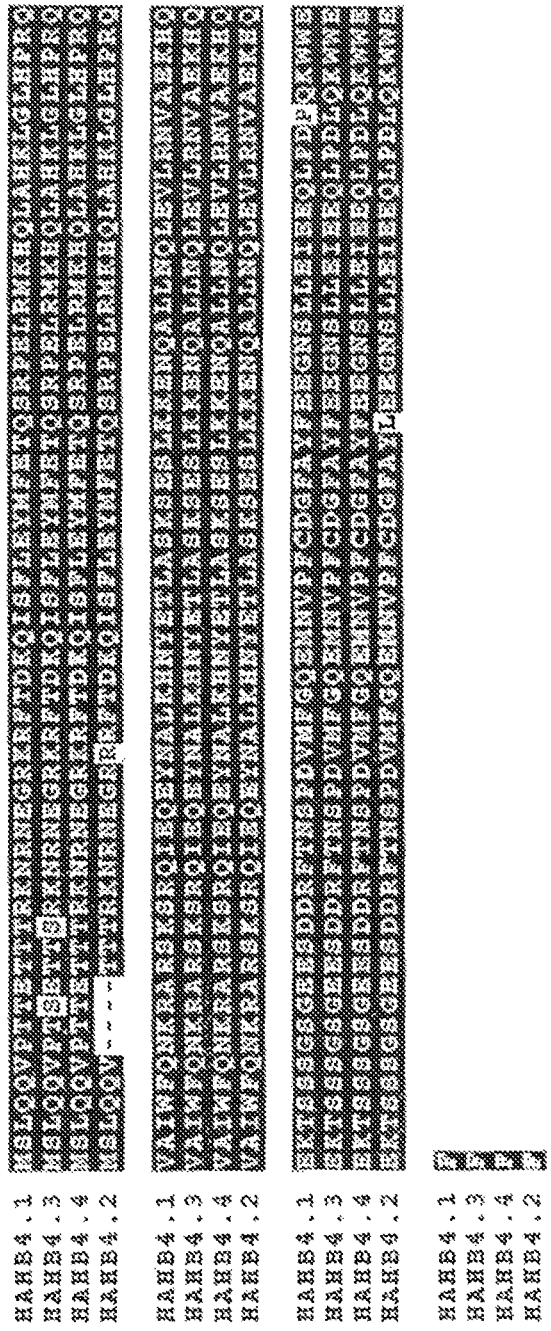

Dezar, C.A., et al., "The promoter of the sunflower HD-Zip protein gene *Hahb4* directs tissue-specific expression and is inducible by water stress, high salt concentrations and ABA," *Plant Science* 169:447-459, Elsevier Ireland Ltd., Ireland (2005).

Gago, G.M., et al.,"*Hahb-4*, a homeobox-leucine zipper gene potentially involved in abscisic acid-dependent responses to water stress in sunflower," *Plant Cell Environ.* 25:633-640, Blackwell Science Ltd, England (2002).

Gehring, W.J., "Homeo Boxes in the Study of Development," *Science* 236:1245-1252, American Association for the Advancement of Science, United States (1987).

Gehring, W.J., et al., "Homeodomain Proteins," *Annu. Rev. Biochem.* 63:487-526, Annual Reviews, United States (1994).

Gonzalez, D.H., et al., "Interaction between proteins containing homeodomains associated to leucine zippers from sunflower," *Biochimica et Biophysica Acta* 1351:137-149, Elsevier Science B.V., Netherlands (1997).

Gonzalez, D.H. and Chan, R.L., "Screening cDNA libraries by PCR using λ sequencing primers and degenerate oligonucleotides," *Trends in Genetics* 9(7):231-232, Elsevier Science Publishers, England (1993).

Hjellström, M., et al., "Constitutive expression of the water deficit-inducible homeobox gene *ATHB7* in transgenic *Arabidopsis* causes a suppression of stem elongation growth," *Plant Cell Environ.* 26:1127-1136, Blackwell Scientific Publications, England (2003).

Ingram, J., and Bartels, D., "The Molecular Basis of Dehydration Tolerance in Plants," *Annu. Rev. Plant Physiol. Plant Mol. Biol.* 47:377-403, Annual Reviews Inc., United States (1996).

Kagaya, Y., et al., "The promoter from the rice nuclear gene encoding chloroplast aldolase confers mesophyll-specific and light-regulated expression in transgenic tobacco," *Mol Gen Genet* 248:668-674, Springer-Verlag, Germany (1995).

Lee, Y-H., and Chun, J-Y., "A new homeodomain-leucine zipper gene from *Arabidopsis thaliana* induced by water stress and abscisic acid treatment," *Plant Mol. Biol.* 37:277-384, Kluwer Academic, Netherlands (1998).

Leung, J., and Giraudat, J., "Abscisic Acid Signal Transduction," *Annu. Rev. Plant Physiol. Plant Mol. Biol.* 49:199-222, Annual Reviews Inc., United States (1998).

Liu, Q., et al., "Two Transcription Factors, *DREB1* and *DREB2*, with an EREBP/AP2 DNA Binding Domain Separate Two Cellular Signal Transduction Pathways in Drought- and Low-Temperature-Responsive Gene Expression, Respectively, in *Arabidopsis*," *Plant Cell* 10:1391-1406, American Society of Plant Physiologists, United States (1998).

Manavella, P.A., et al., "Cross-talk between ethylene and drought signalling pathways is mediated by the sunflower Hahb-4 transcription factor," *The Plant Journal* 48:125-137, Blackwell Publishers Ltd, England (2006).

Manavella, P.A., et al., "HAHB4, a sunflower HD-Zip protein, integrates signals from the jasmonic acid and ethylene pathways during wounding and biotic stress responses," *The Plant Journal* 56:376-388, Blackwell Publishers Ltd, England (2008).

Manavella, P.A., et al., "The sunflower HD-Zip transcription factor HAHB4 is up-regulated in darkness, reducing the transcription of photosynthesis-related genes," *Journal of Experimental Botany* 59(11):3143-3155, Oxford University Press, England (2008).

Manavella, P.A., and Chan, R.L., "Transient transformation of sunflower leaf discs via an *Agrobacterium*-mediated method: applications for gene ezpression and silencing studies," *Nature Protocols* 4(11):1699-1707, Nature Publishing Group, England (2009).

Manavella, P.A., et al., "Two ABREs, two redundant root-specific and one W-box *cis*-acting elements are functional in the sunflower *HAHB4* promoter," *Plant Physiology and Biochemistry* 46:860-867, Elsevier Masson SAS, France (2008).

Nakashima, K., and Yamaguchi-Shinozaki, K., "Molecular Studies on Stress-Responsive Gene Expression in *Arabidopsis* and Improvement of Stress Tolerance in Crop Plants by Regulon Biotechnology," *JARQ* 39:221-229, Japan International Research Center for Agricultural Sciences, Japan (2005).

Olsson, A.S., et al., "The homeobox genes *ATHB12* and *ATHB7* encode potential regulators of growth in response to water deficit in *Arabidopsis*," *Plant Mol. Biol.* 55:663-677, Kluwer Academic, Netherlands (2004).

Palena, C.M., "A monomer-dimer equilibrium modulates the interaction of the sunflower homeodomain leucine-zipper protein Hahb-4 with DNA," *Biochem. J.* 341:81-87, Portland Press, England (1999).

Palena, C.M., et al., "A novel type of dimerization motif, related to leucine zippers, is present in plant homeodomain proteins," *Biochimica et Biophysica Acta* 1352:203-212, Elsevier Science B.V., Netherlands (1997).

Palena, C.M., et al., "Expression of Sunflower Homeodomain Containing Proteins in *Escherichia coli*: Purification and Functional Studies," *Protein Expression and Purification* 13:97-103, Academic Press, United States (1998).

Palena, C.M., et al., "Positively Charged Residues at the N-terminal Arm of the Homeodomain are Required for Efficient DNA Binding by Homeodomain-leucine Zipper Proteins," *Journal of Molecular Biology* 308:39-47, Academic Press, United States (2001).

Pimentel, D., et al., "Water Resources: Agriculture, the Environment and Society," *BioScience* 47:97-106, American Institute of Biological Sciences, United States (1997).

Ré, D.A., et al., "RNAi-mediated silencing of the HD-Zip gene *HD20* in *Nicotiana attenuata* affects benzyl acetone emission from corollas via ABA levels and the expression of metabolic genes," *BMC Plant Biology* 12:60, BioMed Central Ltd., England (2012).

Ré, D.A., et al., "*Nicotiana attenuata* NaHD20 plays a role in leaf ABA accumulation during water stress, benzylacetone emission from flowers, and the timing of bolting and flower transitions," *Journal of Experimental Botany* 62(1):155-166, Oxford Univeristy Press, England (2010).

Riechmann, J.L. and Ratcliffe, O.J., "A genomic perspective on plant transcription factors," *Current Opinion in Plant Biology* 3:423-434, Elsevier Science Ltd., England (2000).

Rueda, E.C., et al.,"*Hahb-10*, a Sunflower Homeobox-Leucine Zipper Gene, is Regulated by Light Quality and Quantity, and PromotesEarly Flowering when Expressed in *Arabidopsis*," *Plant and Cell Physiology* 46(12):1954-1963, Japanese Society of Plant Physiologists, Japan (2005).

Schena, M., et al., "The *HAT4* gene of *Arabidopsis* encodes a developmental regulator," *Genes Dev.* 7:367-379, Cold Spring Laboratory Press, United States (1993).

Sessa, G., et al., "The Athb-1 and -2 HD-Zip domains homodimerize forming complexes of different DNA binding specificities," *EMBO J.* 12:3507-3517, Oxford University Press, England (1993).

Sessa, G., et al., "DNA-binding Specificity of the Homeodomain-leucine Zipper Domain," *J. Mol. Biol.* 274:303-309, Academic Press, United States (1997).

Shinozaki, K., and Yamaguchi-Shinozaki, K., "Gene Expression and Signal Transduction in Water-Stress Response," *Plant Physiol.* 115:327-334, American Society of Plant Physiologists, United States (1997).

Söderman, E., et al., "The *Arabidopsis* homeobox gene *ATHB-7* is induced by water deficit and by abscisic acid," *Plant J.* 10:375-381, Blackwell Scientific Publishers, England (1996).

Söderman, E., et al., "The HD-Zip gene *ATHB6* in *Arabidopsis* is expressed in developing leaves, roots and carpels and up-regulated by water deficit conditions," *Plant Mol. Biol.* 40:1073-1083, Kluwer Academic, Netherlands (1999).

Tron, A.E., et al., "Combinatorial interactions of two amino acids with a single base pair define target site specificity in plant dimeric homeodomain proteins," *Nucleic Acids Research* 29(23):4866-4872, Oxford University Press, England (2001).

Tron, A.E., et al., "Redox Regulation of Plant Homeodomain Transcription Factors," *Journal of Biological Chemistry* 277(38):34800-34807, The American Society for Biochemistry and Molecular Biology, Inc., United States (2002).

Valle, E.M., et al., "Isolation and expression pattern of *hahr1*, a homeobox-containing cDNA from *Helianthus annuus*," *Gene* 196:61-68, Elsevier Science B.V., Netherlands (1997).

Yang, D., et al., "Expression of the REB transcriptional activator in rice grains improves the yield of recombinant proteins whose genes

(56) References Cited

OTHER PUBLICATIONS are controlled by a *Reb*-responsive promoter," *PNAS* 98(20):11438-11443, National Academy of Sciences, United States (2001).
Zanetti, M.E., et al., "Homeodomain-leucine Zipper Proteins Interact with a Plant Homologue of the Transcriptional Co-activator Multiprotein Bridging Factor 1," *Journal of Biochemistry and Molecular Biology* 37(3):320-324, Springer-Verlag, Germany (2004).
Accession No. AF339749, NCBI Database, Gago et al., accessed at www.ncbi.nlm.gov/nuccore/af339749, accessed on Dec. 9, 2011.
International Search Report for International application No. PCT/US2013/026945, mailed Jun. 25, 2013.

```
Hahb-4       MSLQQVPTTETTTRKN RNEGRKRFTDKQISFLEYMFETQSRPELRMKHQLAHKLGLHPRQ 60
mod1Hahb-4   MSLQQVTT----TRKN RNEGRRRFTDKQISFLEYMFETQSRPELRMKHQLAHKLGLHPRQ 56
mod2Hahb-4   MSLQQVP-----TRKN RNEGRRRFTDKQISFLEYMFETQSRPELRMKHQLAHKLGLHPRQ 55

Hahb-4       VAIWFQNKRARSKSRQIEQEYNALKHNYETLASKSESLKKENQALLNQLEVLRNV AEKHQ 120
mod1Hahb-4   VAIWFQNKRARSKSRQIEQEYNALKHNYETLASKSESLKKENQALLNQLEVLRNV AEKHQ 116
mod2Hahb-4   VAIWFQNKRARSKSRQIEQEYNALKHNYETLASKSESLKKENQALLNQLEVLRNV AEKHQ 115

Hahb-4       EKTSSSGSGEESDDRFTNSPDVMFGQEMNVPFCDGFAYFEEGNSLLEIEEQLPDPQKWWEF 181
mod1Hahb-4   EKTSSSGSGEESDDRFTNSPDVMFGQEMNVPFCDGFAYLEEGNSLLEIEEQLPDLQKWWEF 177
mod2Hahb-4   EKTSSSGSGEESDDRFTNSPDVMFGQEMNVPFCDGFAYLEEGNSLLEIEEQLPDLQKWWEF 176
```

MODIFIED *HELIANTHUS ANNUUS* TRANSCRIPTION FACTOR IMPROVES YIELD

CROSS REFERENCE TO RELATED APPLICATIONS

This application claims the benefit of U.S. Provisional App. No. 61/601,335, filed Feb. 21, 2012, which is incorporated by reference in its entirety.

REFERENCE TO SEQUENCE LISTING SUBMITTED ELECTRONICALLY

The content of the electronically submitted sequence listing (Name: 2510_0090001_Sequence_Listing_ASCII.txt; Size: 2800 bytes; and Date of Creation: Feb. 20, 2013) filed with the application is incorporated herein by reference in its entirety.

BACKGROUND OF THE INVENTION

1. Field of the Invention

The invention relates to polynucleotides encoding a modified HaHB4 transcription factor and polynucleotides encoding functionally active fragments and variants of a modified HaHB4 transcription factor as well as vectors and host cells containing these polynucleotides and the polypeptides encoded by these polynucleotides. The invention also encompasses transgenic host cells (including plant cells), plants, seed, pollen, and plant parts containing the polypeptides and/or polynucleotides of the invention. The invention further encompasses methods of producing transgenic host cells, plants, seed, pollen, and plant parts and the processed plant products produced from these transgenic hosts.

2. Background Art

The homeodomain is generally known to be a conserved DNA binding motif of 61 amino acids present in a subset eukaryotic transcription factors that are involved in regulating developmental processes in higher organisms (Gehring, Science 236: 1245-1252 (1987)). Genes encoding homeodomain containing proteins have been isolated from many eukaryotic organisms including fungi, mammals and plants (Gehring et al., Annu. Rev. Biochem. 63:487-526 (1994)). However, genes encoding proteins that contain a homeodomain associated with a protein interacting leucine zipper domain (often referred to as HD-Zip proteins) have to date, only been found in plants. Homeodomain-leucine zipper proteins are generally believed to be involved in regulating developmental processes associated with the response of plants to environmental conditions (Chan et al., Biochim. Biophys. Acts 1442(1): 1-9 (1998), Carabelli et al., Plant J. 4:469-479 (1993); Schena et al., Genes Dev. 7:367-379 (1993)).

HaHB4 is a sunflower (*Helianthus annuus*) transcription factor that belongs to the subfamily 1 of HD-Zip proteins and shares about 50% amino acid sequence identity within the homeodomain with other members of this sub-family, with the exception of the *Arabidopsis thaliana* transcription factors AtHB7 and AtHB12, that share 60% and 53% identity, respectively with the corresponding HaHB4 homeodomain sequence HaHB4 is endogenously expressed at very low levels in sunflower plants grown under controlled and normal environmental conditions. The upregulation of endogenous HaHB4 expression in limited water availability and upon exposure to abscisic acid (ABA) is believed to lead to an increased tolerance to the sunflower plant to water stress. Similarly, transgenic *Arabidopsis thaliana* expressing recombinant HaHB4 have been reported to demonstrate increased tolerance for water stress (drought) conditions. In particular, U.S. Pat. No. 7,674,955 discloses that transgenic *Arabidopsis thaliana* plants overexpressing HaHB4 display increased tolerance to drought as compared to the wild type variety of the *Arabidopsis thaliana* plant under the same conditions. However, U.S. Pat. No. 7,674,955 does not disclose the modified HaHB4 transcription factors described herein, or the increased yield of transgenic plants containing these modified HaHB4 transcription factors under water-stressed and non-water stressed conditions as compared to the wild type variety of the plants under the same conditions.

Increasing agricultural yields and the ability of crops to tolerate a wider range of environmental conditions present two approaches for addressing the major challenges faced by world agriculture in feeding an ever growing population on continuously shrinking arable land resources. Accordingly, there is a need to provide new varieties of crops and other plants that display increased crop yield and tolerance to environmental stress.

BRIEF SUMMARY OF THE INVENTION

HaHB4 is a member of a sub-family of plant transcription factors that are believed to be involved in regulating developmental processes associated with the response of plants to environmental conditions. Genetically engineered expression of *Helianthus annuus* transcription factor HaHB4 in transgenic plants has been reported to improve agronomic tolerance to drought and salinity conditions. No yield improvement has reported in standard growth conditions, but light penalties in production have been reported when the expression of HaHB4 was too high when directed by a constitutive promoter. Here we report on the use of modified HaHB4 sequences for the genetic engineering of transgenic plants with increased yield. More particularly, upon sequencing the HaHB4 transgenes from wheat, maize and soybean lines displaying increased yields, the inventors have surprisingly determined that the transgenes have distinct sequence alterations when compared to the sequence of native HaHB4 (SEQ ID NO:2). In addition, the inventors have generated an additional modified HaHB4 sequence containing overlapping different segments encoding native and modified HaHB4 proteins.

Accordingly, in one embodiment, the invention relates to polynucleotides encoding a modified HaHB4 transcription factor, which upon expression in transgenic plants, results in an increased yield or tolerance to environmental stress when grown under either water-stressed or non-water stressed conditions as compared to a wild type variety of such plant grown under similar environmental conditions. In an additional embodiment, the invention relates to polynucleotides encoding a modified HaHB4 transcription factor, which upon expression in transgenic plants, results in an increased photosynthesis rate. The invention also relates to polynucleotides encoding modified HaHB4 (modHaHB4 (e.g., mod1HaHB4, mod2HaHB4, mod3HaHB4 and mod4HaHB4)) and polynucleotides encoding functionally active fragments and variants of modHaHB4, as well as vectors and host cells containing these polynucleotides and the proteins encoded by these polynucleotides. The invention also encompasses transgenic host cells (including plant cells), plants, seeds, pollen, and plant parts containing the polypeptides and/or polynucleotides of the invention. Methods of producing transgenic host cells, plants, seeds, pollen, and plant parts using the polynucleotides of the invention and the seed, progeny, and processed plant products produced from these transgenic host cells, plants, seed, pollen, and plant parts are also encompassed by the invention.

According to one embodiment, the invention is directed to a nucleic acid molecule comprising a polynucleotide sequence encoding a fragment or variant of HaHB4 (SEQ ID NO:2) wherein transgenic plants containing the nucleic acid molecule have an increased yield when grown under either water-stressed or non-water stressed conditions as compared to a control wild type variety of such plant grown under similar environmental conditions. In another embodiment, the invention is directed to a nucleic acid molecule comprising a polynucleotide sequence encoding a fragment or variant of HaHB4 (SEQ ID NO:2) wherein transgenic plants containing the nucleic acid molecule have an increased photosynthesis rate. An additional embodiment is directed to a nucleic acid molecule comprising a polynucleotide sequence encoding a fragment or variant of HaHB4 (SEQ ID NO:2) wherein transgenic plants containing the nucleic acid molecule have an increased yield when grown under either water-stressed or non-water stressed conditions as compared transgenic HaHB4 (SEQ ID NO:2) plants of the same variety, wherein recombinant HaHB4 expression is under control of the same promoter. An additional embodiment is directed to a nucleic acid molecule comprising a polynucleotide sequence encoding a fragment or variant of HaHB4 (SEQ ID NO:2) wherein transgenic plants containing the nucleic acid molecule have an increased photosynthesis rate. In another embodiment, nucleic acid molecules of the invention comprise a polynucleotide sequence encoding the HaHB4 variant mod1HaHB4 (HaHB4.2 (SEQ ID NO:4)) wherein transgenic plants containing the nucleic acid molecule have an increased yield when grown under water-stressed or non-water stressed conditions as compared to a control wild type variety of such plant grown under similar environmental conditions. In another embodiment, nucleic acid molecules of the invention comprise a polynucleotide sequence encoding the HaHB4 variant mod1HaHB4 (HaHB4.2 (SEQ ID NO:4)) wherein transgenic plants containing the nucleic acid molecule have an increased photosynthesis rate when grown under water-stressed or non-water stressed conditions as compared to a control wild type variety of such plant grown under similar environmental conditions. An additional embodiment is directed to a nucleic acid molecule comprising a polynucleotide sequence encoding a fragment or variant mod1HaHB4 (HaHB4.2 (SEQ ID NO:4)) wherein transgenic plants containing the nucleic acid molecule have an increased yield and/or increased photosynthesis rate when grown under water-stressed or non-water stressed conditions as compared to transgenic HaHB4 (SEQ ID NO:2) plants of the same variety, wherein recombinant HaHB4 expression is under control of the same promoter. An additional embodiment is directed to a nucleic acid molecule comprising a polynucleotide sequence encoding a fragment or variant mod1HaHB4 (HaHB4.2 (SEQ ID NO:4)) wherein transgenic plants containing the nucleic acid molecule have an increased photosynthesis rate when grown under water-stressed or non-water stressed conditions as compared to transgenic HaHB4 (SEQ ID NO:2) plants of the same variety, wherein recombinant HaHB4 expression is under control of the same promoter.

In an additional embodiment, nucleic acid molecules of the invention comprise a polynucleotide sequence encoding the HaHB4 variant mod2HaHB4 (HaHB4.3 (SEQ ID NO:8)) wherein transgenic plants containing the nucleic acid molecule have an increased yield when grown under water-stressed or non-water stressed conditions as compared to a control wild type variety of such plant grown under similar environmental conditions. In an additional embodiment, nucleic acid molecules of the invention comprise a polynucleotide sequence encoding the HaHB4 variant mod2HaHB4 (HaHB4.3 (SEQ ID NO:8)) wherein transgenic plants containing the nucleic acid molecule have an increased photosynthesis rate when grown under water-stressed or non-water stressed conditions as compared to a control wild type variety of such plant grown under similar environmental conditions. Another embodiment is directed to a nucleic acid molecule comprising a polynucleotide sequence encoding a fragment or variant mod2HaHB4 (HaHB4.3 (SEQ ID NO:8)) wherein transgenic plants containing the nucleic acid molecule have an increased yield when grown under water-stressed or non-water stressed conditions as compared to transgenic HaHB4 (SEQ ID NO:2) plants of the same variety, wherein recombinant HaHB4 expression is under control of the same promoter. Another embodiment is directed to a nucleic acid molecule comprising a polynucleotide sequence encoding a fragment or variant mod2HaHB4 (HaHB4.3 (SEQ ID NO:8)) wherein transgenic plants containing the nucleic acid molecule have an increased photosynthesis rate when grown under water-stressed or non-water stressed conditions as compared to transgenic HaHB4 (SEQ ID NO:2) plants of the same variety, wherein recombinant HaHB4 expression is under control of the same promoter.

In another embodiment, nucleic acid molecules of the invention comprise a polynucleotide sequence encoding the HaHB4 variant mod3HaHB4 (HaHB4.4 (SEQ ID NO:38)) wherein transgenic plants containing the nucleic acid molecule have an increased yield and/or increased photosynthesis rate when grown under water-stressed or non-water stressed conditions as compared to a control wild type variety of such plant grown under similar environmental conditions. Another embodiment is directed to a nucleic acid molecule comprising a polynucleotide sequence encoding a fragment or variant mod3HaHB4 (HaHB4.4 (SEQ ID NO:38)) wherein transgenic plants containing the nucleic acid molecule have an increased yield and/or increased photosynthesis rate when grown under water-stressed or non-water stressed conditions as compared to transgenic HaHB4 (SEQ ID NO:2) plants of the same variety, wherein recombinant HaHB4 expression is under control of the same promoter.

In an additional embodiment, nucleic acid molecules of the invention comprise a polynucleotide sequence encoding the HaHB4 variant mod4HaHB4 (HaHB4.5 (SEQ ID NO:39)) wherein transgenic plants containing the nucleic acid molecule have an increased yield and/or increased photosynthesis rate when grown under water-stressed or non-water stressed conditions as compared to a control wild type variety of such plant grown under similar environmental conditions. Another embodiment is directed to a nucleic acid molecule comprising a polynucleotide sequence encoding a fragment or variant mod4HaHB4 (SEQ ID NO:39) wherein transgenic plants containing the nucleic acid molecule have an increased yield and/or increased photosynthesis rate when grown under water-stressed or non-water stressed conditions as compared to transgenic HaHB4 (SEQ ID NO:2) plants of the same variety, wherein recombinant HaHB4 expression is under control of the same promoter.

The invention also provides a nucleic acid molecule comprising a polynucleotide sequence encoding (a) the HaHB4 variant mod1HaHB4 (HaHB4.2 (SEQ ID NO:4)); (b) a functionally active fragment of mod1HaHB4, wherein the amino acid sequence of said fragment is not present in the corresponding sequence of HaHB4 (SEQ ID NO:2); or (c) a functionally active variant of mod1HaHB4 (SEQ ID NO:4), wherein said variant comprises an amino acid sequence that is at least 80%, 85%, 90%, 95%, 96%, 97%, 98%, or 99% identical to the amino acid sequence of SEQ ID NO:4, and wherein the amino acid sequence of said variant is not present in the corresponding sequence of HaHB4 (SEQ ID NO:2). Isolated nucleic acid molecules comprising the polynucleotide sequence of SEQ ID NO:3, SEQ ID NO:12, SEQ ID NO:13, SEQ ID NO:15 or SEQ ID NO:16 or the complementary strand thereof, and fragments and variants of these nucleic acid molecules that are not present in the corresponding polynucleotide sequence of HaHB4 (SEQ ID NO:1 and SEQ ID NO:18), are also encompassed by the invention.

In another embodiment, the invention provides a nucleic acid molecule comprising a polynucleotide sequence encoding (a) the HaHB4 variant mod2HaHB4 (HaHB4.3 (SEQ ID NO:8)); (b) a functionally active fragment mod2HaHB4, wherein the amino acid sequence of said fragment is not present in the corresponding sequence of HaHB4 (SEQ ID NO:2); or (c) a functionally active variant of mod2HaHB4 (HaHB4.3 (SEQ ID NO:8)) wherein said variant comprises an amino acid sequence that is at least 80%, 85%, 90%, 95%, 96%, 97%, 98%, or 99% identical to the amino acid sequence of SEQ ID NO:8; and wherein the amino acid sequence of said variant is not present in the corresponding sequence of HaHB4 (SEQ ID NO:2). Isolated nucleic acid molecules comprising the polynucleotide sequence of SEQ ID NO:14 or SEQ ID NO:17, or the complementary strand thereof, and fragments and variants of these nucleic acid molecules that are not present in the corresponding polynucleotide sequence of HaHB4 (SEQ ID NO:1 and SEQ ID NO:18), are also encompassed by the invention.

In one embodiment, the invention provides a nucleic acid molecule comprising a polynucleotide sequence encoding the HaHB4 variant mod3HaHB4 (HaHB4.4 (SEQ ID NO:38)). In another embodiment, the invention provides a nucleic acid molecule comprising a polynucleotide sequence encoding the HaHB4 variant mod4HaHB4 (HaHB4.5 (SEQ ID NO:39)).

According to some embodiments, functionally active polypeptide variants or fragments encoded by the polynucleotides of the invention are capable of binding the DNA sequence 5'-CAAT(A/T)ATTG-3' (SEQ ID NO:11) in vitro. In further embodiments, the functionally active polypeptide variants or fragments encoded by the polynucleotides of the invention are capable of binding the DNA sequence 5'-CAAT(A/T)ATTG-3' (SEQ ID NO:1) in a solution consisting of 20 mM HEPES-NaOH (pH 7.6), 50 mM KCl, 2 mM $MgCl_2$, 0.5 mM EDTA, 1.0 mM DTT, 0.5% Triton X-100, 10% glycerol, and 1.0 μg poly(dI-dC), at 24° C. In other embodiments, transgenic plant cells expressing the functionally active polypeptide variants or fragments of the invention have a different gene expression profile, than wild type control cells (e.g., parental) of comparable tissue, at a comparable stage of development, and grown under comparable conditions. In further embodiments, transgenic plant cells expressing the functionally active polypeptide fragments or variants of the invention have a different transcription profile than transgenic HaHB4 cells of comparable tissue, at a comparable stage of development, and grown under comparable conditions, and wherein transgenic HaHB4 expression is under the control of the same promoter as modHaHB4 fragment or variant coding sequence. In additional embodiments, transgenic plants expressing the functionally active polypeptide fragments or variants of the invention have an increased yield when grown under water-stressed or non-water stressed conditions as compared to a wild type variety of such plant grown under similar environmental conditions. In additional embodiments, transgenic plants expressing the functionally active polypeptide fragments or variants of the invention have an increased photosynthesis rate when grown under water-stressed or non-water stressed conditions as compared to a wild type variety of such plant grown under similar environmental conditions. In further embodiments transgenic plants expressing the functionally active polypeptide fragments or variants of the invention have increased yield when grown under water-stressed or non-water stressed conditions as compared to transgenic HaHB4 plants grown under similar environmental conditions, wherein transgenic HaHB4 expression is under the control of the same promoter as mod1HaHB4 fragment or variant coding sequence. In further embodiments transgenic plants expressing the functionally active polypeptide fragments or variants of the invention have increased photosynthesis rate when grown under water-stressed or non-water stressed conditions as compared to transgenic HaHB4 plants grown under similar environmental conditions, wherein transgenic HaHB4 expression is under the control of the same promoter as modHaHB4 fragment or variant coding sequence.

Nucleic acids, including vectors and expression cassettes, comprising the polynucleotides of the invention operably associated with a promoter are also encompassed by the invention. According to some embodiments, the polynucleotides of the invention are operably associated with a constitutive promoter. In particular embodiments, the constitutive promoter is the 35S CaMV promoter or the Ubi1 promoter. According to other embodiments, the polynucleotides of the invention are operably associated with an inducible promoter. In particular embodiments, the inducible promoter is a modified version of HaHB4 promoter fused with the first intron of the *Arabidopsis* Cox5c-2.

The invention also encompasses host cells comprising the nucleic acids of the invention. Exemplary host cells for use according to the invention include, but are not limited to, bacterial, fungal, insect, plant and animal cells. In particular embodiments, the host cell is a plant cell. According to some embodiments, the host is a monocot plant cell. In further embodiments, the host cell is wheat (*Triticum aestivum*), corn (*Zea mays*), or rice (*Oryza sativa*). According to other embodiments, the host cell is a dicot plant cell. In particular embodiments, the host cell is soybean (*Glycine max*). In additional embodiments, the host cell is *Arabidopsis* (*Arabidopsis thaliana*).

Transgenic plants, seed, pollen, plant parts, and transgenic plant cells comprising polynucleotide sequences of the invention are also encompassed by the invention. In one embodiment, the transgenic plant, seed, pollen, plant part, or transgenic plant cell comprises a polynucleotide sequence encoding mod1HaHB4 (SEQ ID NO:4). In further embodiments, the polynucleotide encoding mod1HaHB4 comprises a polynucleotide sequence selected from: SEQ ID NO:3, SEQ ID NO:12, SEQ ID NO:13, SEQ ID NO:15 and SEQ ID NO:16. In another embodiment, the transgenic plant, seed, pollen, plant part, or transgenic plant cell comprises a polynucleotide sequence encoding mod2HaHB4 (SEQ ID NO:8). In further embodiments, the polynucleotide encoding mod2HaHB4 comprises a polynucleotide sequence selected from SEQ ID NO:14 and SEQ ID NO:17.

In another embodiment, the transgenic plant, seed, pollen, plant part, or transgenic plant cell comprises a polynucleotide sequence encoding mod3HaHB4 (SEQ ID NO:38). In another embodiment, the transgenic plant, seed, pollen, plant part, or transgenic plant cell comprises a polynucleotide sequence encoding mod4HaHB4 (SEQ ID NO:39).

In an additional embodiment, the invention encompasses a transgenic plant, seed, pollen or plant part comprising a polynucleotide sequence encoding (a) mod1HaHB4 (SEQ ID NO:4); (b) a functionally active fragment of mod1HaHB4 (SEQ ID NO:4), wherein the amino acid sequence of said fragment is not present in the corresponding sequence of HaHB4 (SEQ ID NO:2); or (c) a functionally active variant of mod1HaHB4 (SEQ ID NO:4), wherein said variant comprises an amino acid sequence that is at least 80%, 85%, 90%, 95%, 96%, 97%, 98%, or 99% identical to the amino acid sequence of SEQ ID NO:4, and wherein the amino acid sequence of said variant is not present in the corresponding sequence of HaHB4 (SEQ ID NO:2).

In another embodiment, the invention encompasses a transgenic plant seed, pollen or plant part comprising a polynucleotide sequence encoding (a) mod2HaHB4 (SEQ ID NO:8); (b) a functionally active fragment of mod2HaHB4, wherein the amino acid sequence of said fragment is not present in HaHB4 protein (SEQ ID NO:2); or (c) a functionally active variant of mod2HaHB4 (SEQ ID NO:8), wherein said variant comprises an amino acid sequence that is at least 80%, 85%, 90%, 95%, 96%, 97%, 98%, or 99% identical to the amino acid sequence of SEQ ID NO:8, and wherein the amino acid sequence of said fragment is not present in HaHB4 (SEQ ID NO:2).

In another embodiment, the invention encompasses a transgenic plant seed, pollen or plant part comprising a polynucleotide sequence encoding (a) mod3HaHB4 (SEQ ID NO:38); (b) a functionally active fragment of mod3HaHB4, wherein the amino acid sequence of said fragment is not present in HaHB4 protein (SEQ ID NO:2); or (c) a functionally active variant of mod3HaHB4 (SEQ ID NO:38), wherein said variant comprises an amino acid sequence that is at least 80%, 85%, 90%, 95%, 96%, 97%, 98%, or 99% identical to the amino acid sequence of SEQ ID NO:38, and wherein the amino acid sequence of said fragment is not present in HaHB4 (SEQ ID NO:2).

In another embodiment, the invention encompasses a transgenic plant seed, pollen or plant part comprising a polynucleotide sequence encoding mod4HaHB4 (SEQ ID NO:39).

According to some embodiments, transgenic plants expressing polynucleotides of the invention have increased yield as compared to the wild type variety of the plant. In other embodiments, transgenic plants expressing polynucleotides of the invention have increased yield when grown under water-stressed or non-water stressed conditions as compared to the wild type variety of the plant. In other embodiments, transgenic plants expressing polynucleotides of the invention have increased photosynthesis rate when grown under water-stressed or non-water stressed conditions as compared to the wild type variety of the plant. In additional embodiments, transgenic plants expressing polynucleotides of the invention have improved tolerance to one or more environmental stresses as compared to the wild type variety of the plant. Environmental stresses in response to which the transgenic plants of the invention may demonstrate improved tolerance, include, but are not limited to drought, salinity, osmotic stress, cold temperature exposure, heat exposure, reduced nitrogen nutrient availability, reduced phosphorous nutrient availability, and high plant density.

In additional embodiments, transgenic plants expressing polynucleotides of the invention have increased yield as compared to a HaHB4 transgenic of the corresponding wild-type plant variety, wherein recombinant HaHB4 expression is under control of the same promoter as the coding polynucleotides of the invention. In other embodiments, transgenic plants expressing polynucleotides of the invention have increased yield when grown under water-stressed or non-water stressed conditions as compared to a HaHB4 transgenic of the corresponding wild-type plant variety, wherein recombinant HaHB4 expression is under control of the same promoter as the coding polynucleotides of the invention. In other embodiments, transgenic plants expressing polynucleotides of the invention have increased photosynthesis rate when grown under water-stressed or non-water stressed conditions as compared to a HaHB4 transgenic of the corresponding wild-type plant variety, wherein recombinant HaHB4 expression is under control of the same promoter as the coding polynucleotides of the invention. In additional embodiments, transgenic plants expressing polynucleotides of the invention have improved tolerance to one or more environmental stresses as compared to a HaHB4 transgenic of the corresponding wild-type plant variety.

According to some embodiments, the transgenic plant, seed, or plant part monocot. In some embodiments, the transgenic plant, seed, or plant part is wheat (*Triticum aestivum*). In additional embodiments, the transgenic plant, seed, or plant part is corn (*Zea mays*). In other embodiments, the transgenic plant, seed, or plant part is rice (*Oryza sativa*). In additional embodiments, the transgenic plant, seed, or plant part of the invention is a dicot. In some embodiments, the transgenic plant, seed, or plant part is soybean (*Glycine max*). In additional embodiments, the transgenic plant, seed, or plant part is *Arabidopsis thaliana*. Seed and progeny of the transgenic plant cells and transgenic plants are also encompassed by the invention, as are the seed and processed plant products produced from these transgenic plants, their seed, and their progeny.

The invention is also directed to methods of producing transgenic hosts, including, but not limited to, bacteria, fungal, and plant cells, and transgenic plants comprising the polynucleotides of the invention. The progeny and seed of the transgenic host cells and transgenic plants produced according to these methods, as well as processed plant products produced from these transgenic hosts, their seed, and their progeny.

BRIEF DESCRIPTION OF THE DRAWINGS/FIGURES

FIG. 1A provides an alignment between HaHB4 transcription factor (SEQ ID NO:2), modified HaHB4 transcription factor 1 (mod1HaHB4HaHB4.2 (SEQ ID NO:4); and modified HaHB4 transcription factor 2 (mod2HaHB4 (SEQ ID NO:8)). The homeodomain-leucine zipper region is boxed. FIG. 1B provides alignment between HaHB4 transcription factor (HaHB4.1 (SEQ ID NO:2)), mod1HaHB4 (HaHB4.2 (SEQ ID NO:4)): mod2HaHB4 (HaHB4.3 (SEQ ID NO:8)); mod3HaHB4 (HaHB4.4 (SEQ ID NO:38)); and mod4HaHB4 (HaHB4.5 (SEQ ID NO:39)).

Figure 2A:
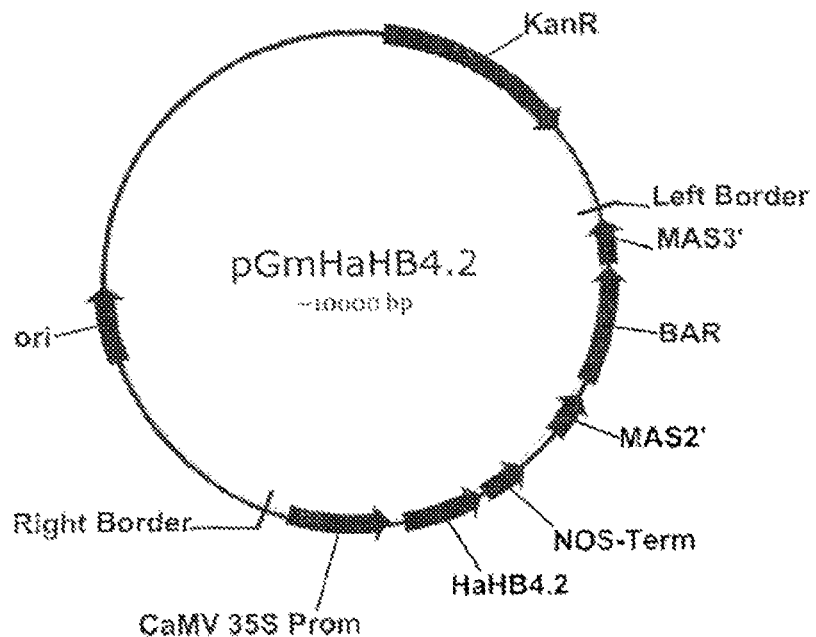
Figure 2B:
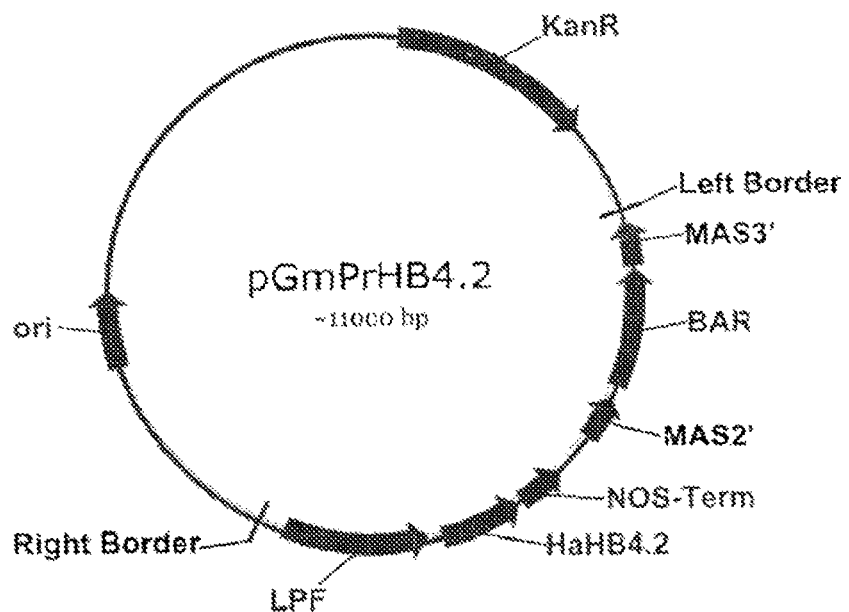
Figure 2C:
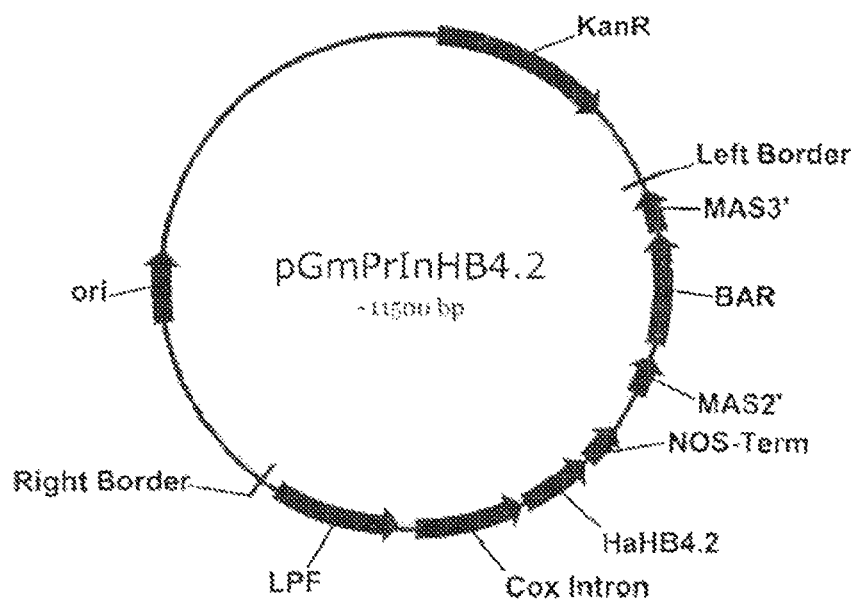
Figure 2D:
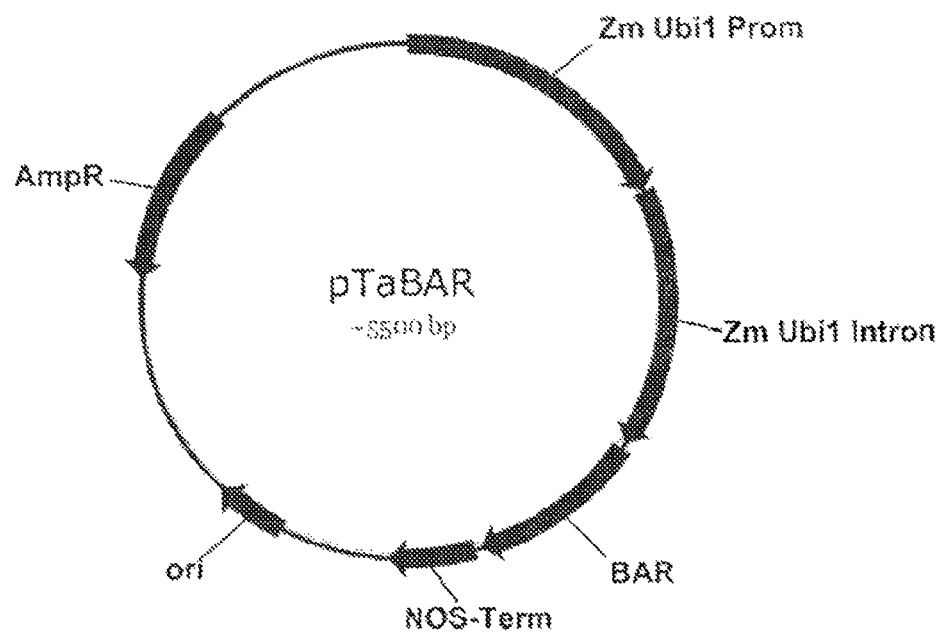
Figure 2E:
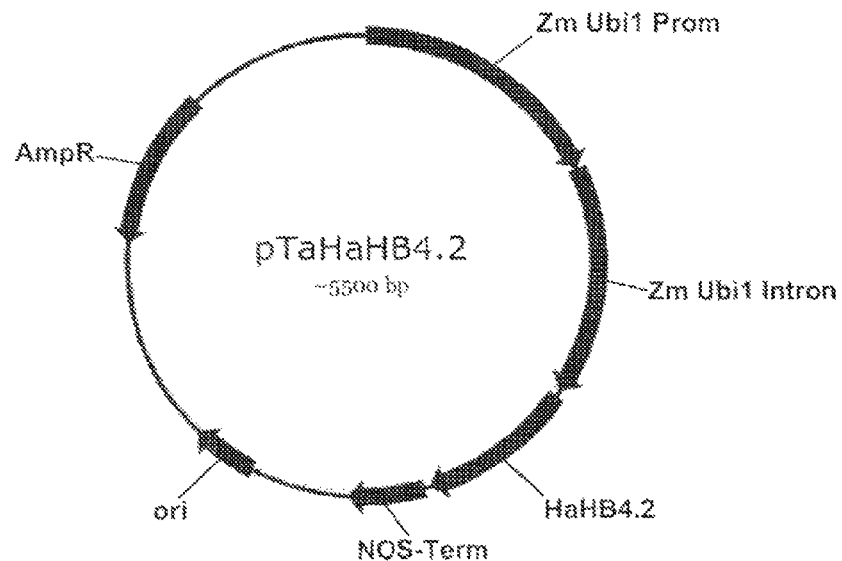
Figure 2F:
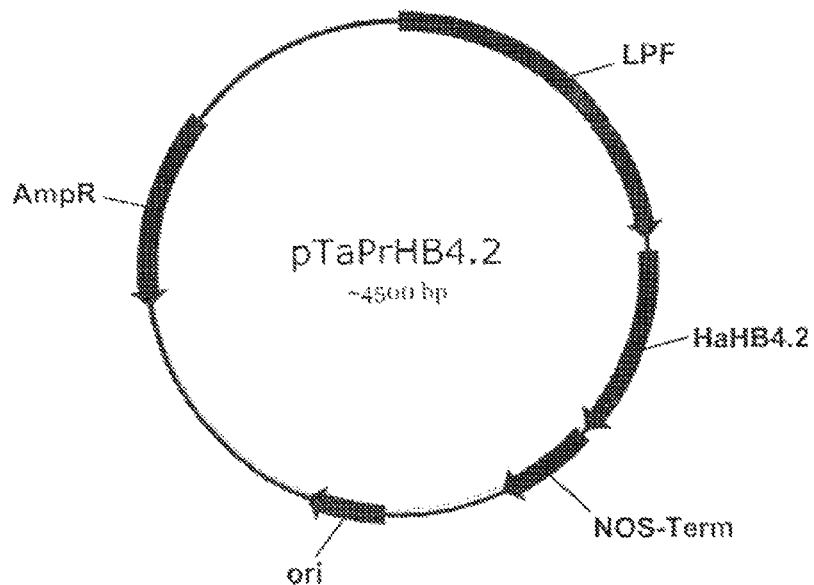
Figure 2G:
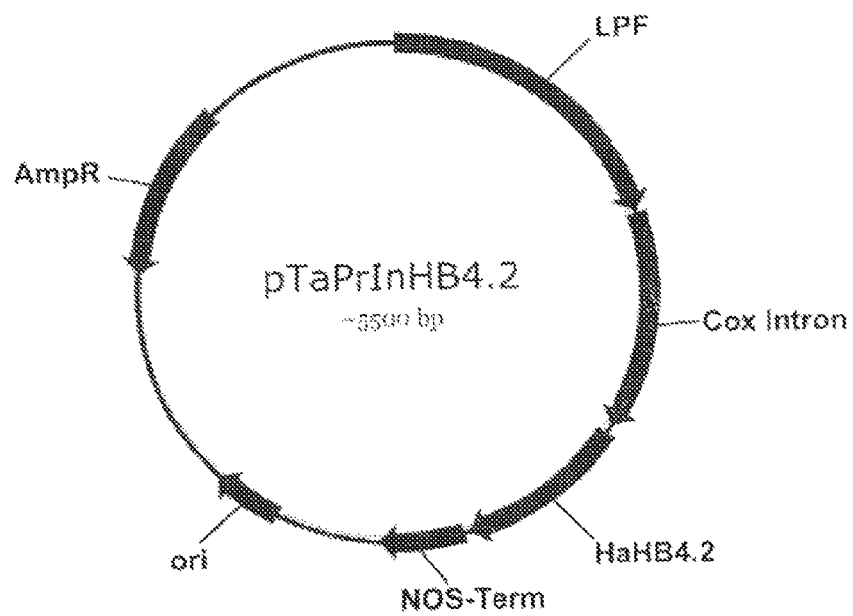
Figure 2H:
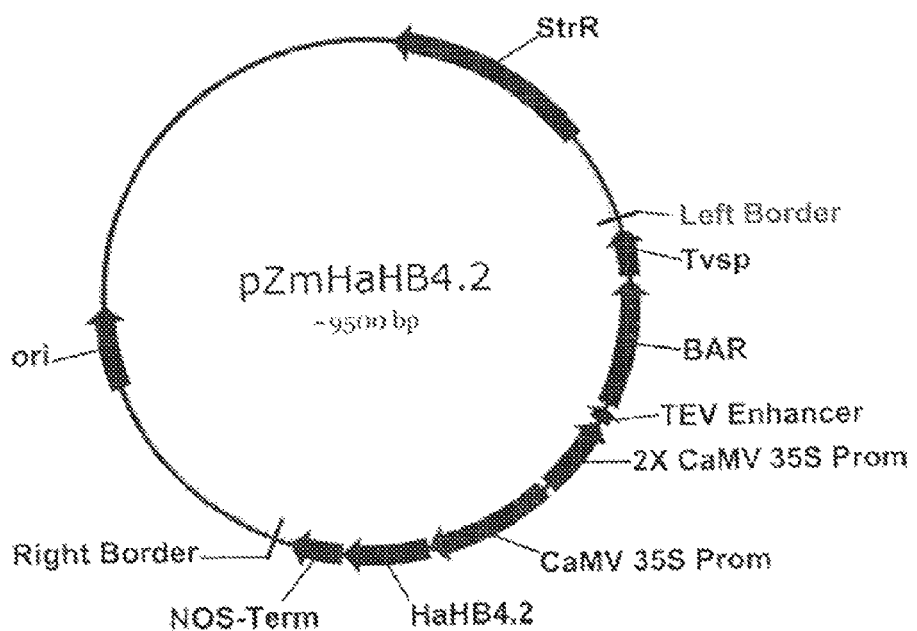
Figure 2I:
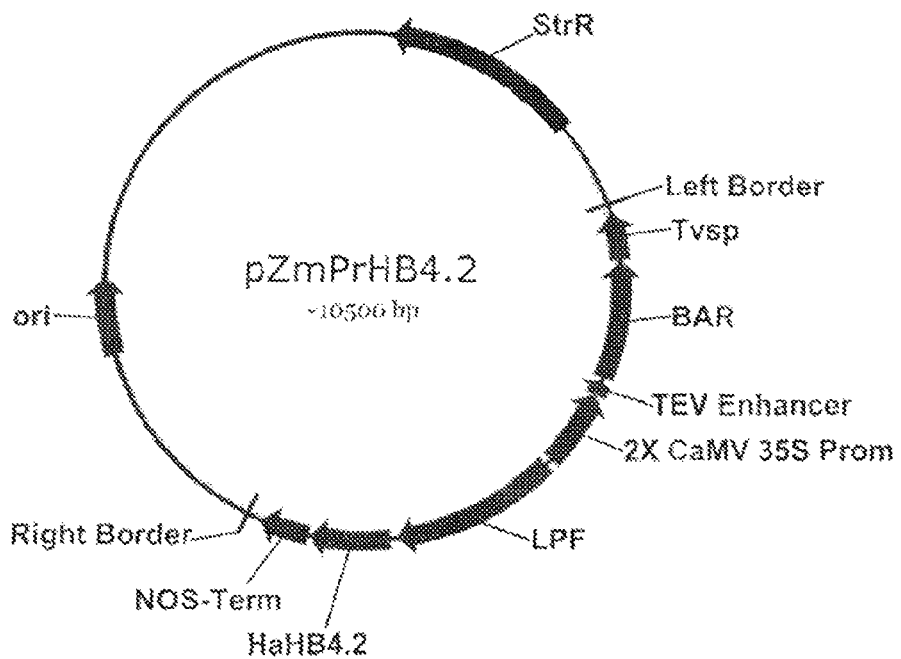
Figure 2J:
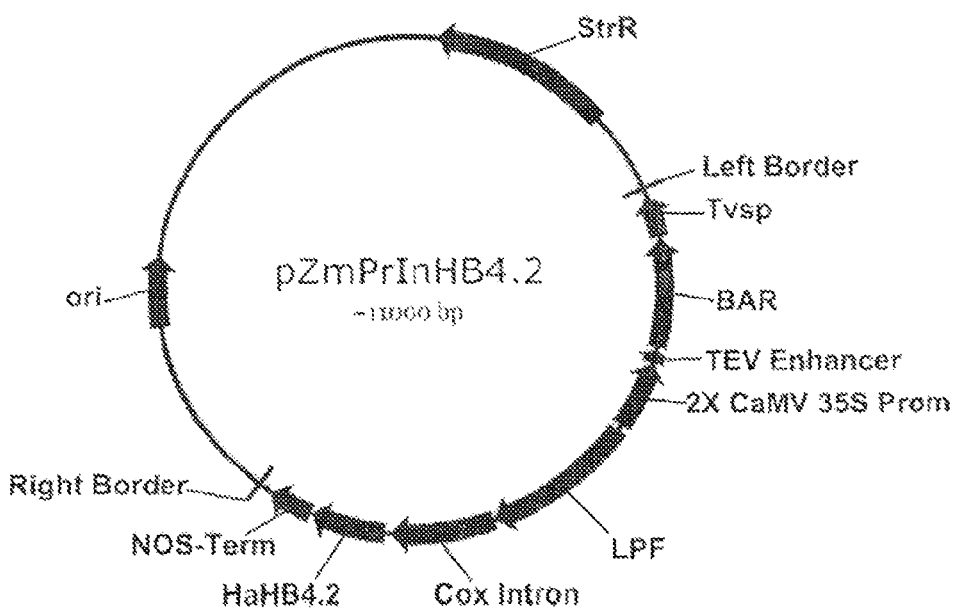

FIGS. 2A-2J provide a schematic depiction of exemplary vectors and constructs referenced in the application for transforming host cells with the polynucleotides of the invention. FIGS. 2A-C depict constructs pGmHaHB4.2, pGmPrHB4.2, and pGmPrInB4.2, respectively, that have applications in transforming, soybean and other plants. FIG. 2 D-G depict constructs pTaBAR, pTaHaHB4.2, pTaPrHB4.2, and pTaPrInHB4.2, respectively, that have applications in transforming wheat and other plants. FIGS. 2H-J depict constructs pZmHaH34.2, pZMPrHB4, and pZmPrInHB4.2, respectively, that have applications in transforming maize and other plants. Abbreviations: aadA (aminoglycoside 3'-adenylyltransferase gene of *S. flexneris* 2a that confers resistance to antibiotic streptomycin), bar (phosphinothricin acetyl transferase gene from *S. hygroscopicus* that confers resistance to herbicide phosphinothricin and its derivatives), P35S (the cauliflower mosaic virus 35S promoter), Tnos (NOS-Term; 3' terminator from nopaline synthase gene of *A. tumefaciens*); Tvsp (3' terminator from soybean vegetative storage protein gene), TEV (Tobacco Etch Virus translational enhancer); RB (T-DNA right border fragment from nopaline strain of *A. tumefaciens*); LB (T-DNA left border fragment from nopaline strain of *A. tumefaciens*); pVSI (broad host range plasmid from *Pseudomonas*); AmpR (Ampicillin resistance gene); KanR (Kanamycin resistance gene); ori (replication origin in bacteria); HaHB4.2 (modified HaHB4 sequence as described in Examples Section (pTHaHB4.2c insert); LPF (1HaHB4 promoter with modifications described in Examples Section); and COX5c-2 intron (first intron of COX5c-2 gene).

Figure 3A:
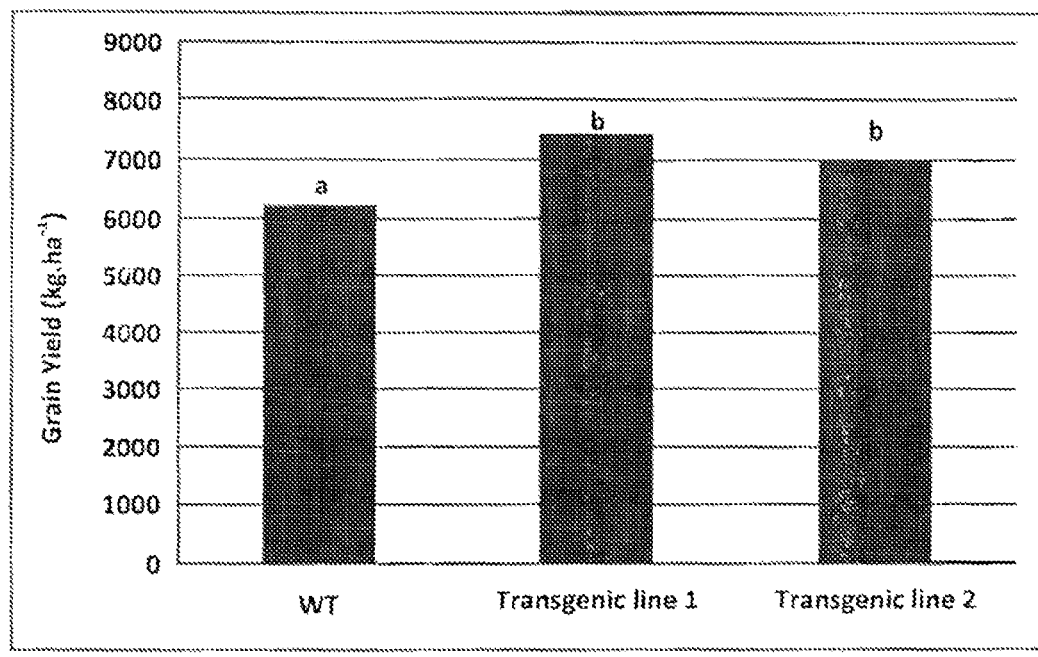
Figure 3B:
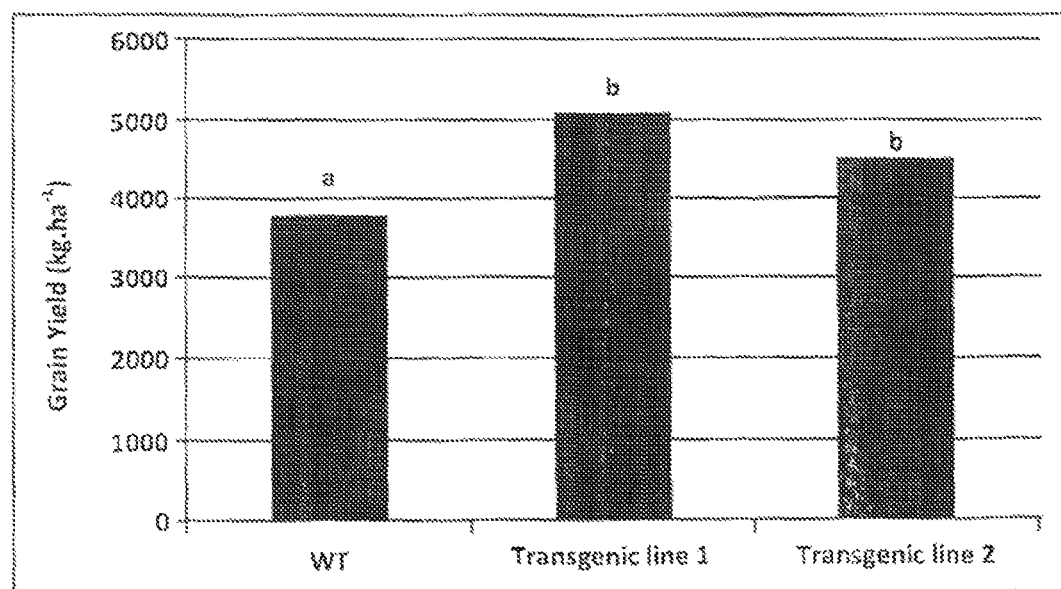
Figure 3C:
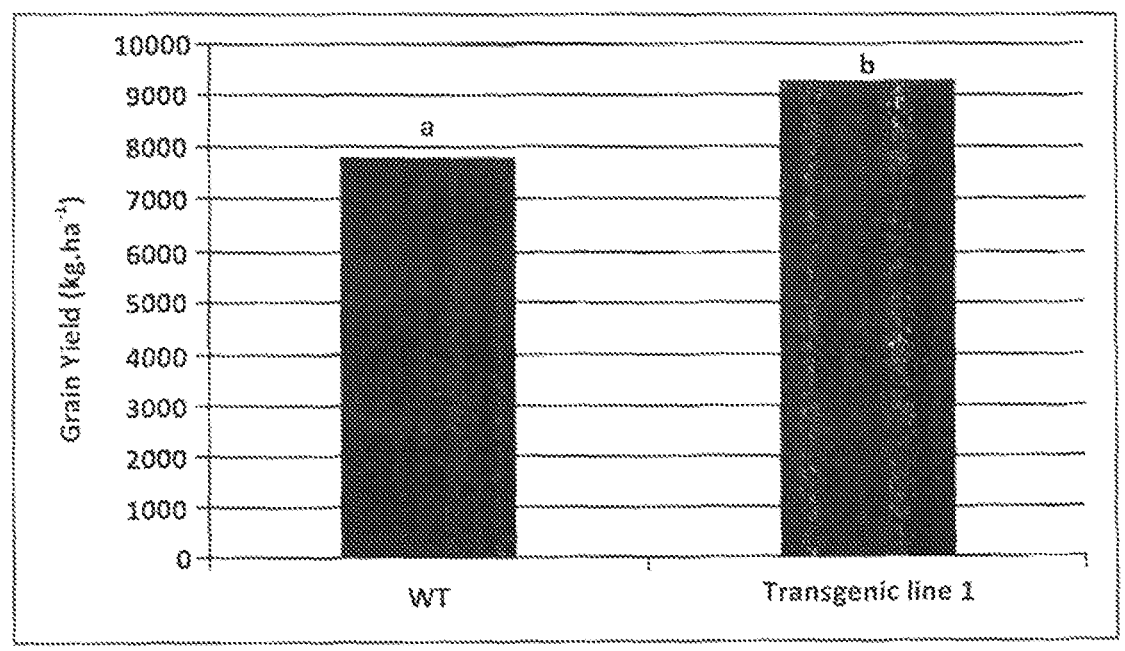
Figure 3D:
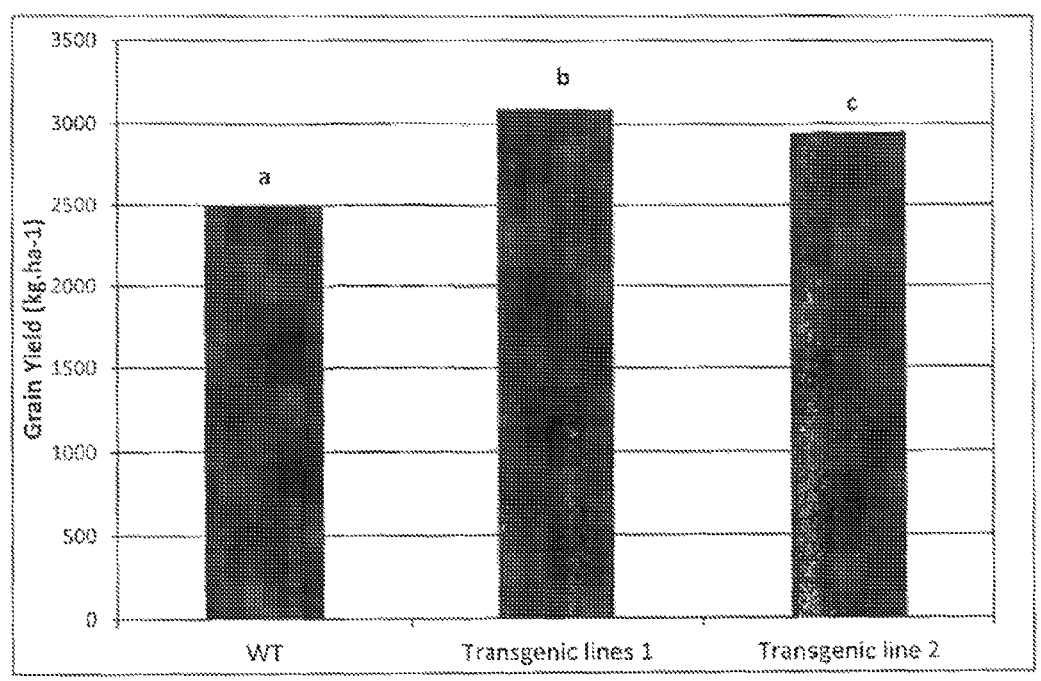

FIGS. 3A-3D provide bar graphs indicating yield improvement in transgenic crops under irrigated field conditions (without water limitations under non-water stressed conditions) in a high productivity environment. FIGS. 3A-3B depict transgenic maize data indicating grain yield (kg/ha) corresponding to two homozygous transgenic maize lines constitutively expressing HaHB4.2 (SEQ ID NO:4) and wild type control maize (WT). Data were collected from replicated field plots in two locations with different soil types: in a silty loam soil with 626 mm of rain received throughout the growing period (FIG. 3A), and in a well-drained silty loam soil with 545 mm of rain received during the crop cycle (FIG. 38). FIG. 3C depicts transgenic wheat data indicating grain yield (kg/ha) corresponding to a homozygous transgenic wheat line constitutively expressing HaHB4.2 (SEQ ID NO:4) and wild type control wheat (WT). Data in FIG. 3C were obtained from replicated field plots in a location with well drained sandy loam soil (pH 7.14%, OM 1.57%). Supplemental irrigation was applied to provide for 755 mm of water throughout the crop cycle. FIG. 3D provide transgenic soybean data indicating grain yield (kg/ha) corresponding to two homozygous transgenic soybean lines constitutively expressing HaHB4.2 (SEQ ID NO:4) and wild type control soybean (WT). Data in FIG. 3D were obtained from replicated field plots in location with sandy loam soil (pH 5.99%, OM 1.41%). Supplemental irrigation was applied to provide for 579 mm of water throughout the crop cycle.

Figure 4:
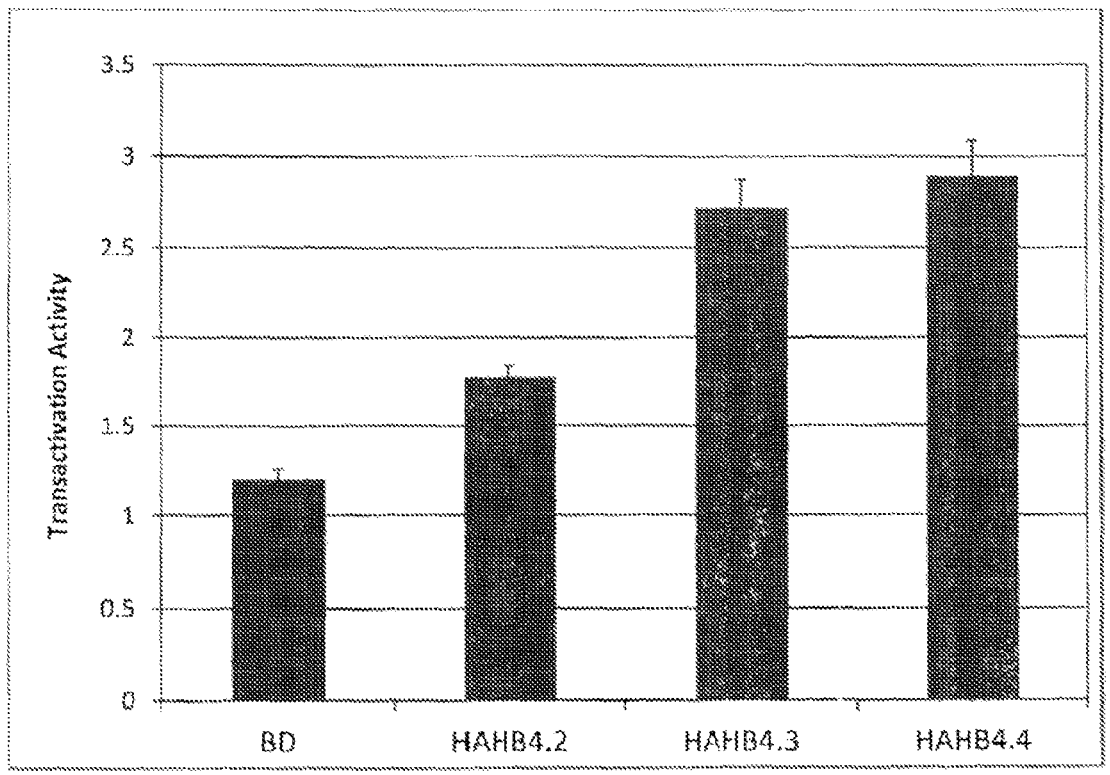

FIG. 4 provides a bar graph indicating transactivator activity of various modified HaHB4 in a simple yeast hybrid assay.

Figure 5:
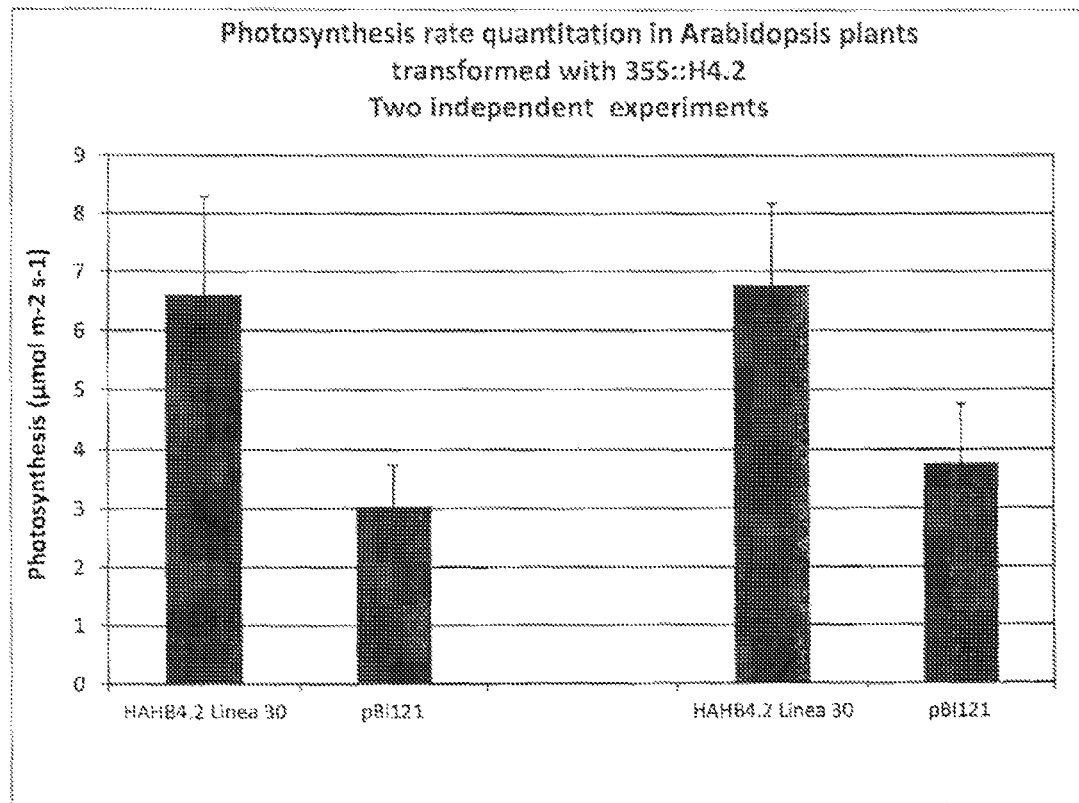

FIG. 5 provides a bar graph indicating the photosynthesis rate in two independent experiments of *Arabidopsis* plants transformed with an expression cassette containing the 35S constitutive promoter operably associated with nucleic acid sequence encoding mod1HaHB4 (HaHB4.2 (SEQ ID NO:4) (i.e., 35S.H4.2).

DETAILED DESCRIPTION OF THE INVENTION

Definitions

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties.

The term "polynucleotide" is intended to encompass a singular nucleic acid molecule as well as to any one or more nucleic acid segments, e.g., DNA or RNA fragments, present in a nucleic acid molecule, and refers to an isolated nucleic acid molecule or construct (e.g., vector), e.g., messenger RNA (mRNA) or plasmid DNA (pDNA) relating to a polynucleotide of the invention. The terms "nucleic acid" and "polynucleotide" are used interchangeably herein. By "isolated" nucleic acid or polynucleotide is intended a nucleic acid molecule, DNA or RNA, which has been removed from its native environment. For example, an isolated polynucleotide includes recombinant polynucleotides maintained in heterologous host cells or purified (partially or substantially) polynucleotides in solution. Isolated RNA molecules include in vivo or in vitro RNA transcripts of polynucleotides of the present invention. In addition, a polynucleotide or a nucleic acid can be or can include a regulatory element such as a promoter, ribosome binding site, or a transcription terminator.

As used herein, a "coding region" is a portion of nucleic acid molecule which consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. In addition, a vector, polynucleotide, or nucleic acid of the invention can encode heterologous coding regions.

In certain embodiments, the polynucleotide or nucleic acid is DNA. In the case of DNA, a polynucleotide comprising a nucleic acid which encodes a polypeptide can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" or "operably linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. Generally, operably linked means that the polynucleotide sequences being linked are contiguous and, where necessary to join two protein encoding regions, contiguous and in reading frame so as to produce a "fusion protein." A "fusion protein" is a protein comprising amino acid sequences derived from two or more heterologous polypeptides.

The term "promoter" as used herein refers a regulatory nucleic acid fragment that functions to control the transcription of one or more genes, located upstream with respect to the direction of transcription of the transcription initiation site of the gene, and is structurally identified by the presence of a binding site for DNA-dependent RNA polymerase transcription initiation sites and any other DNA sequences, including, but not limited to, transcription factor binding sites, repressor and activator protein binding sites, and any other polynucleotide sequence known in the art to act directly or indirectly to regulate the amount of transcription from the promoter.

A "plant promoter" is a promoter capable of initiating transcription in plant cells whether or not its origin is a plant cell, e.g., is it well known that *Agrobacterium* promoters are functional in plant cells. Accordingly, plant promoters include promoter DNA sequences derived from plants, plant viruses and bacteria such as *Agrobacterium*. Examples of promoters under developmental control include promoters that preferentially or only initiate transcription in certain cell types or tissues, such as leaves, roots, or seeds; and promoters that are "inducible" or "repressible" under environmental conditions including for example, anaerobic conditions, exposure to certain chemicals, and variations in exposure to light. Promoters of the invention include "constitutive" promoters that are active in most tissues under most physiological and developmental conditions and "non-constitutive" or "inducible" physiologically (e.g., by external application of certain compounds) or developmentally regulated promoters. Examples of constitutive promoters disclosed herein include, but are not limited to, the 35S CaMV promoter (see, e.g., pGmHaHB4.2 (FIG. 2A), and pZmHaHB4.2 (FIG. 2H)), and Ubi promoter (see, e.g., pTaHaHB4.2 (FIG. 2E)). Examples of inducible promoters useful according to the invention are also disclosed herein and include, but are not limited to, a modified HaHB4 promoter (see, e.g., pGmPrHR4.2 (FIG. 2B), pTaPrHB4.2 (FIG. 2F), and pZMPrHB4.2 (FIG. 2I)) and an inducible promoter composed of a modified version of HaHB4 promoter fused with the first intron of the *Arabidopsis* Cox5c-2 gene (see, e.g., pGmPrInHB4.2 (FIG. 2C), and pTaPrInHB4.2 (FIG. 2G), and pZmPrInHB4.2 (FIG. 2J)).

"Regulatory sequences" or "regulatory elements" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, operators, repressors, transcription termination signals, translation leader sequences, introns, polyadenylation recognition sequences, RNA processing site, effector binding site and stem-loop structure.

The terms "plasmid" and "vector" and "expression cassette" are used interchangeably herein and refer to an extra chromosomal element often carrying genes which are not part of the central metabolism of the cell. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. Any vector including a plasmid, cosmid, phage or *Agrobacterium* binary vector in double or single stranded linear or circular form which may or may not be self-transmissible or mobilizable, and which can transform prokaryotic or eukaryotic host either by integration into the cellular genome or exist extrachromosomally (e.g., an autonomously replicating plasmid with an origin of replication) can be used in practicing the methods and making the compositions of the invention. Specifically included are shuttle vectors by which is meant a DNA vehicle capable, naturally or by design, of replication in two different host organisms, which may be selected from for example, bacteria, higher plants, yeast or fungal cells.

Alternatively, the term "expression cassette" may refer to a nucleic acid fragment that expresses one or more specific proteins, including regulatory sequences preceding (5' non-coding sequences) and following (3' termination sequences) coding sequences for the proteins.

As used herein the term "transformation" refers to the transfer of a nucleic acid into a host organism, resulting in genetically stable inheritance. Host organisms containing the transformed nucleic acid fragments are referred to as "transgenic" or "recombinant" or "transformed" organisms.

The terms "express" or "expression", as used herein, refer to the transcription and accumulation of sense (mRNA) or antisense RNA derived from the nucleic acid fragment of the invention. Expression may also refer to translation of mRNA into a polypeptide. The process includes any manifestation of the functional presence of the expressed polynucleotide, gene, or polypeptide within the cell including, without limitation, gene knockdown as well as both transient expression and stable expression.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product or post-translationally modified form of the product. The terms "polypeptide" and "protein" are used interchangeably herein.

As used herein, the term "host cell" refers to any kind of cellular system which can be engineered to express the polypeptides of the invention. Host cells include cultured cells, yeast cells, insect cells, plant cells, and mammalian cells to name only a few, as well as cells comprised within a transgenic organism, such as a transgenic plant, or cultured plant tissue.

As used herein, the term "plant" includes reference to whole plants, plant parts (e.g., leaves, stems, roots, etc.), seeds, pollen and plant cells and progeny of same. Plant cell, as used herein includes, without limitation, seeds, suspension cultures, embryos, meristematic regions, callus tissue, leaves, roots, shoots, gametophytes, sporophytes, pollen, and microspores.

As used herein a "transgenic plant cell" means a plant cell that is transformed with a stably-integrated polynucleotide sequence of the invention or alternatively, with an autonomously replicating vector containing a polynucleotide sequence of the invention. The term "stably integrated" as used herein, refers to polynucleotides that are chromosomally integrated, genetically stable, and heritable by progeny through successive generations. Methods for transforming plant cells are described herein or otherwise known in the art and include, but are not limited to, *Agrobacterium*-mediated transformation, electroporation, and DNA coated microparticle bombardment. Transgenic plant cells of the invention include both originally-transformed plant cells that exists as a cell culture or organism, a progeny plant cell present in regenerated and/or into differentiated tissue, such as a transgenic plant with stably-integrated, non-natural recombinant polynucleotide sequences of the invention. Transgenic plant cells also include seed or pollen derived from a transgenic plant progeny. For the purposes of the invention, the terms "grain," "seed" and "kernel" are used interchangeably.

As used herein, "transgenic plant" includes reference to a plant, which comprises within its genome a polynucleotide of the invention. Generally, the polynucleotide of the invention is stably integrated within the genome of the host such that the polynucleotide is passed on to successive generations. The heterologous polynucleotide may be integrated into the genome alone or as part of a recombinant expression cassette. "Transgenic" is used herein to include any cell, cell line, callus, plant part or plant, containing a polynucleotide of the invention including those transgenics that are initially so altered as well as those created by sexual crosses or asexual propagation from the initial transgenic.

As used herein, the term "functionally active" refers to polynucleotides and polypeptides (including fragments and variants) capable of exhibiting at least one functional activity of HaHB4 or a modified HaHB4 transcription factor. In one embodiment, a functionally active polypeptide of the invention (including fragments and variants) is capable of binding the DNA sequence 5'-CAAT(A/T)ATTG-3' (SEQ ID NO:11) In vitro. In further embodiments, the functionally active polypeptides of the invention are capable of binding the DNA sequence 5'-CAAT(A/T)ATTG-3' (SEQ ID NO:11) in a solution consisting of 20 mM HEPES-NaOH (pH 7.6), 50 mM KCl, 2 mM $MgCl_2$, 0.5 mM EDTA, 1.0 mM DTT, 0.5% Triton X-100, 10% glycerol, and 1.0 µg poly(dI-dC), at 24° C. DNA-binding assays that can be used to identify functionally active polypeptides encoding by the polynucleotides of the invention are known in the art and can routinely be applied or modified as needed. According to one example, the presence of functional modified HaHB4 DNA binding proteins can be assayed by an electrophoretic mobility shift assay (EMSA) using a synthetic double-stranded oligonucleotide comprising the sequence 5'-CAAT(A/T)ATTG-3' (SEQ ID NO:11). For example, purified bacterial (e.g., *E. coli*) proteins or purified plant cell nuclear proteins can be incubated with radio-labeled double-stranded DNA containing the sequence 5'-AATTCAGATCTCAATAATTGAGAG-3' (SEQ ID NO:36) and 5-GATCCTCTCAATTATTGAGATCTG-3 (SEQ ID NO:37) in binding medium containing 20 mM HEPES-NaOH (pH 7.6), 50 mM KCl, 0-2 mM EDTA, 1.0 mM dithiothreitol (DTT), 0.5% Triton X-100, 20% glycerol, and 1.0 ug poly(dI-dC), for 20 min at 25° C. supplemented with 2.5% (w/v) Ficoll and the resulting reaction are then loaded on an acrylamide gel and subsequently evaluated for alterations in the mobility of the DNA on the gel run as a result of DNA binding. Other techniques and assays for evaluating the binding of transcription factors to DNA sequence motifs, and the binding affinities of proteins for DNA are known in the art.

In another embodiment, a functionally active polypeptide of the invention (including fragments and variants) binds one or more different endogenous host plant proteins under physiological conditions than HaHB4 transcription factor (SEQ ID NO:2). In some embodiments, a functionally active polypeptide of the invention is capable of binding an endogenous host plant protein that is not bound by the corresponding polypeptide portion of HaHB4. In other embodiments, a functionally active polypeptide of the invention is not capable of binding an endogenous host plant protein that is bound by the corresponding polypeptide portion of HaHB4. Methods and materials for determining protein-protein interaction including for example, the yeast-two hybrid system, are known in the art and can routinely be adapted and applied to evaluate protein-protein interactions of the polypeptides of the invention. In one embodiment, a functionally active polypeptide of the invention (including fragments and variants) binds one or more different *Arabidopsis thaliana* proteins under physiological conditions than HaHB4 transcription factor (SEQ ID NO:2). Exemplary methods useful in analyzing protein-protein interactions between a polypeptide of the invention and *Arabidopsis thaliana* proteins, include the *Arabidopsis* protoplast two-hybrid (P2H) system disclosed in Ehlert et al., Plant J. 46:890-900 (2006).

In additional embodiments, a host cell containing a functionally active polynucleotide or polypeptide of the invention (including fragments and variants) displays a different transcription profile as compared to a control (e.g. wild type genotype) not containing the polynucleotides or polypeptides of the invention. In one embodiment, a host cell containing a functionally active polynucleotide or polypeptide of the invention displays a different transcription profile under drought, salinity conditions or ethylene exposure, as compared to a control (e.g., wild type genotype) not containing the polynucleotides or polypeptides of the invention.

Transcription profile analyses can be performed using reagents and techniques known in the art. Such techniques include, but are not limited to, microarray, RT-PCR, RNAse protection, Northern, and Western analysis. Expression profiling, generally by microarray analysis, can be used to simultaneously measure differences or induced changes in the expression of many different genes. Techniques for microarray analysis and other techniques for evaluating the expression of a coding sequence, such as Northern, Western, PCR, and RNAse protection analysis are known in the art (Schena et al., Science 270:467-470 (1995); Baldwin et al., Curr. Opin. Plant Biol. 2(2):96-103 (1999); Dangond F, Physiol. Genomics 2:53-58 (2000); van Hal et al., J. Biotechnol. 78:271-280 (2000); Richmond and Somerville, Curr. Opin. Plant Biol. 3:108-116 (2000); Almoguera et al., Plant Mol. Biol. 19:781-792 (1992); and Ausubel et al., eds., 1998, Current Protocols in Molecular Biology, John Wiley & Sons, NY.

In one embodiment, the transcription profile analysis is performed on transgenic *Arabidopsis thaliana* plants, plant parts, or plant cells of the invention. Exemplary methods useful in transcription profile analyses of the transgenic plants, plant parts, or plant cells of the invention are provided in Manavella et al., Plant Journal 48:125-137 (2006) and Hilson et al., Gen. Res. 14:2176-2189 (2004); each of which is herein incorporated by reference in its entirety. For example, according to one method, transcriptome analysis is performed using a CATMA array containing 24,576 gene-specific tags from *Arabidopsis thaliana*. In additional methods, real time RT-PCR is performed using oligonucleotide primers designed using publicly available sequences (see, e.g., *Arabidopsis*.org; and Crowe et al., Nucl. Acids. Res. 31:156-158 (2003)).

In an additional embodiment, a host cell containing a functionally active polynucleotide or polypeptide of the invention displays a different transcription or expression profile of mRNA or protein selected from the group consisting of LOX2, CSD1, ERF2, ERF5, ACO, SAM, EIN1, and EIN3, as compared to a control (e.g., wild type genotype) not containing the polynucleotides or polypeptides of the invention. In an additional embodiment, a host cell containing a functionally active polynucleotide or polypeptide of the invention (including fragments and variants) displays a different transcription profile as compared to a transgenic HaHB4 host cell expressing HaHB4 (SEQ ID NO:2) under the same promoter. In a further embodiment, a host cell containing a functionally active polynucleotide or polypeptide of the invention displays a different transcription profile under drought conditions, salinity conditions, or ethylene exposure, as compared to a transgenic HaHB4 host cell expressing HaHB4 (SEQ ID NO:2) under the same promoter. In an additional embodiment, a host cell containing a functionally active polynucleotide or polypeptide of the invention displays a different expression mRNA or protein selected from the group consisting of LOX2, CSD1, ERF2, ERF5, ACO, SAM, EIN1, and EIN3, as compared to a transgenic 1HaHB4 host cell expressing HaHB4 (SEQ ID NO:2) under the same promoter.

In another embodiment, a transgenic plant containing a functionally active polynucleotide or polypeptide of the invention (including fragments and variants) displays an altered yield when compared to a control (e.g., wild type genotype) not containing the polynucleotides or polypeptides of the invention. In another embodiment, a transgenic plant containing a functionally active polynucleotide or polypeptide of the invention (including fragments and variants) displays an altered photosynthesis rate when compared to a control (e.g., wild type genotype) not containing the polynucleotides or polypeptides of the invention. In particular embodiments, a transgenic plant containing a functionally active polynucleotide or polypeptide of the invention displays an increased yield when compared to a control (e.g., wild type genotype) not containing the polynucleotides or polypeptides of the invention. In particular embodiments, a transgenic plant containing a functionally active polynucleotide or polypeptide of the invention displays an increased photosynthesis rate when compared to a control (e.g., wild type genotype) not containing the polynucleotides or polypeptides of the invention. In particular embodiments, a transgenic plant containing a functionally active polynucleotide or polypeptide of the invention displays an increased yield under non-water stressed conditions when compared to a control (e.g. wild type genotype) under the same non-water stressed conditions. In particular embodiments, a transgenic plant containing a functionally active polynucleotide or polypeptide of the invention displays an increased photosynthesis rate under non-water stressed conditions when compared to a control (e.g., wild type genotype) under the same non-water stressed conditions.

In an additional embodiment, a transgenic plant containing a functionally active polynucleotide or polypeptide of the invention (including fragments and variants) displays an altered yield when compared to a transgenic plant expressing HaHB4 (SEQ ID NO:2) under the same promoter. In an additional embodiment, a transgenic plant containing a functionally active polynucleotide or polypeptide of the invention (including fragments and variants) displays an altered photosynthesis rate when compared to a transgenic plant expressing HaHB4 (SEQ ID NO:2) under the same promoter.

In particular embodiments, a transgenic plant containing a functionally active polynucleotide or polypeptide of the invention displays an increased yield when compared to a transgenic plant expressing HaHB4 (SEQ ID NO:2) under the same promoter. In particular embodiments, a transgenic plant containing a functionally active polynucleotide or polypeptide of the invention displays an increased photosynthesis rate when compared to a transgenic plant expressing HaHB4 (SEQ ID NO:2) under the same promoter.

In some embodiments, a transgenic plant containing a functionally active polynucleotide or polypeptide of the invention displays an increased yield when grown under non-water stressed conditions as compared to a transgenic plant expressing HaHB4 (SEQ ID NO:2) under the same promoter and under the same water conditions. In some embodiments, a transgenic plant containing a functionally active polynucleotide or polypeptide of the invention displays an increased photosynthesis rate when grown under non-water stressed conditions as compared to a transgenic plant expressing HaHB4 (SEQ ID NO:2) under the same promoter and under the same water conditions. In some embodiments, a transgenic plant containing a functionally active polynucleotide or polypeptide of the invention displays an increased yield when grown under water-stressed conditions as compared to a transgenic plant expressing HaHB4 (SEQ ID NO:2) under the same promoter and under the same water conditions. In some embodiments, a transgenic plant containing a functionally active polynucleotide or polypeptide of the invention displays an increased photosynthesis rate when grown under water-stressed conditions as compared to a transgenic plant expressing HaHB4 (SEQ ID NO:2) under the same promoter and under the same water conditions.

In further embodiments, a transgenic plant containing a functionally active polynucleotide or polypeptide of the invention displays an increased yield when grown under water-stressed and non-water stressed conditions as compared to a transgenic plant expressing HaHB4 (SEQ ID NO:2) under the same promoter and under the same water conditions. In further embodiments, a transgenic plant containing a functionally active polynucleotide or polypeptide of the invention displays an increased photosynthesis rate when grown under water-stressed and non-water stressed conditions as compared to a transgenic plant expressing HaHB4 (SEQ ID NO:2) under the same promoter and under the same water conditions.

In other embodiments, a transgenic plant containing a functionally active polynucleotide or polypeptide of the invention displays an increased yield when grown under water-stressed or non-water stressed conditions as compared to a control (e.g. wild type genotype) under the same water conditions. In other embodiments, a transgenic plant containing a functionally active polynucleotide or polypeptide of the invention displays an increased photosynthesis rate when grown under water-stressed or non-water stressed conditions as compared to a control (e.g., wild type genotype) under the same water conditions. In particular embodiments, a transgenic plant containing a functionally active polynucleotide or polypeptide of the invention displays an increased yield when grown under water-stressed or non-water stressed conditions as compared to a transgenic plant containing HaHB4 (SEQ ID NO:2) under the same promoter and under the same water conditions. In particular embodiments, a transgenic plant containing a functionally active polynucleotide or polypeptide of the invention displays an increased photosynthesis rate when grown under water-stressed or non-water stressed conditions as compared to a transgenic plant containing HaHB4 (SEQ ID NO:2) under the same promoter and under the same water conditions.

Particular embodiments are directed to methods of using the polynucleotides of the invention to produce a plant which has an increased yield under non-water limiting conditions, water limiting conditions, or under both non-water limiting and water limiting conditions, comprising the steps of introducing a polynucleotide of the invention into a host plant cell, selecting for the presence of the polynucleotide molecule to produce a transgenic plant cell, and regenerating a transgenic plant from the transgenic plant cell, whereby the transgenic plant has an increased yield under non-water limiting conditions or water-limiting conditions, when compared to a comparable wild-type plant or a transgenic HaHB4 plant wherein HaHB4 is under control of the same promoter. Particular embodiments are directed to methods of using the polynucleotides of the invention to produce a plant which has an increased photosynthesis rate under non-water limiting conditions, water limiting conditions, or under both non-water limiting and water limiting conditions, comprising the steps of introducing a polynucleotide of the invention into a host plant cell, selecting for the presence of the polynucleotide molecule to produce a transgenic plant cell, and regenerating a transgenic plant from the transgenic plant cell, whereby the transgenic plant has an increased photosynthesis rate under non-water limiting conditions or water-limiting conditions, when compared to a comparable wild-type plant or a transgenic HaHB4 plant wherein HaHB4 is under control of the same promoter.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

As a practical matter, whether any particular nucleic acid molecule or polypeptide is at least 80%, 85%, 90%, 95%, 96%, 97%, 98%, or 99% identical to a nucleotide sequence or polypeptide sequence of the present invention can be determined conventionally using known computer programs. The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin. A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J, Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignments of the sequences are performed using the "Clustal method of alignment" which encompasses several varieties of the algorithm including the "Clustal V method of alignment" corresponding to the alignment method labeled Clustal V (described by Higgins and Sharp, CABIOS 5:151-153 (1989); Higgins et al., Comput. Appl. Biosci., 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, CABIOS. 5:151-153 (1989); Higgins et al., Comput. Appl. Biosci. 8:189-191 (1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to a reference polypeptide can be determined conventionally using known computer programs. One method for determining the best overall match between a query sequence (a sequence of the present invention) and a subject sequence, also referred to as a global sequence alignment, can be determined using the FASTDB computer program based on the algorithm of Brutlag et al., Comp. App. Biosci. 6:237-245 (1990). In a sequence alignment the query and subject sequences are either both nucleotide sequences or both amino acid sequences. The result of said global sequence alignment is in percent identity. Preferred parameters used in a FASTDB amino acid alignment are: Matrix-PAM 0, k-tuple-2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to be made for the purposes of the present invention.

Percent identity of polynucleotides and/or polypeptides can also be determined using the BLAST programs available through the National Center for Biotechnology Information (NCBI), with the default parameters indicated in the programs.

As used herein, "percent identity" means the extent to which two optimally aligned DNA or protein segments are invariant throughout a window of alignment of components, for example nucleotide sequence or amino acid sequence. An "identity fraction" for aligned segments of a test sequence and a reference sequence is the number of identical components to that are shared by sequences of the two aligned segments divided by the total number of sequence components in the reference segment over a window of alignment which is the smaller of the full test sequence or the full reference sequence. "Percent identity" ("% identity") is the identity fraction times 100. Such optimal alignment is understood to be deemed as local alignment of DNA sequences. For protein alignment, a local alignment of protein sequences should allow introduction of gaps to achieve optimal alignment. Percent identity is calculated over the aligned length not including the gaps introduced by the alignment per se.

As used herein, the term "variant" polynucleotides or polypeptides refers to a polynucleotide or polypeptide differing from a specifically recited polynucleotide or polypeptide of the invention by insertions, deletions, mutations, and substitutions, in amino acid residue and polynucleotide positions, respectively, created using, eg., recombinant DNA techniques. Specifically, recombinant variants encoding these same or similar polypeptides may be synthesized or selected by making use of the "redundancy" in the genetic code. Various codon substitutions, such as the silent changes that produce various restriction sites, may be introduced to optimize cloning into a plasmid or viral vector or expression in a particular prokaryotic or eukaryotic system (i.e., host directed "codon optimization"). Mutations in the polynucleotide sequence may be reflected in the polypeptide or domains of other peptides added to the polypeptide to modify the properties of any part of the polypeptide, to change characteristics such as DNA and other ligand-binding affinities, or degradation/turnover rate. According to some embodiments, the polynucleotides of the invention are codon optimized for optimizing expression of the polypeptide in a transgenic host.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

Many organisms display a bias for use of particular codons to code for insertion of a particular amino acid in a growing peptide chain. Codon preference, or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at the "Codon Usage Database" available on the World Wide Web at kazusa.or.jp/codon/ (visited Mar. 20, 2008), and these tables can be adapted in a number of ways. See Nakamura et al. Nucl. Acids Res. 28:292 (2000).

Using codon usage tables, one of ordinary skill in the art can apply the frequencies to any given polypeptide sequence, and produce a nucleic acid fragment of a codon-optimized coding region which encodes the polypeptide, but which uses codons optimal for expressing a sequence of interest in a host of interest.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the VectorNTI Suite, available from InforMax, Inc., Bethesda, Md., and the "backtranslate" function in the GCG-Wisconsin Package, available from Accetrys, Inc., San Diego, Calif. In addition, various resources are publicly available to codon-optimize coding region sequences, e.g., the "backtranslation" function at the http: "entelechon.com/bioinformatics/backtranslation.php?lang=eng and the "backtranseq" function available at the http "bioinfo.pbi.nrc.ca:8090/EMBOSS/index.html." Constructing a rudimentary algorithm to assign codons based on a given frequency can also easily be accomplished with basic mathematical functions by one of ordinary skill in the art. Moreover, codon-optimized coding regions can be designed by various methods known to those in the art including software packages such as "synthetic gene designer" having an http: that of "phenotype.biosci.umbc.edu/codon/sgd/index.php."

In some embodiments, the invention encompasses polynucleotides that are codon optimized for expressing the polypeptides of interest in a host of interest. Thus, for example, although polynucleotides of the invention may be expressed in both monocotyledonous and dicotyledonous plant species, the polynucleotide sequences can be modified to account for the specific codon preferences and GC content preferences to a monocotyledonous plant or dicotyledonous plant of interest. Codon usage tables and software programs useful for guidance in codon optimizing any given sequence for expression in a host cell of interest are readily available and can be routinely applied using the techniques described herein or otherwise known in the art. For exemplary codon utilization guidance, see e.g., Murray et al., Nucleic Acids Res. 17:477-98 (1989), which is incorporated by reference in its entirety. Polynucleotides encoding the polypeptides of the invention can likewise be recombinantly designed to remove potential destabilizing sequences and potential secondary structure that can be readily identified and modified using techniques known in the art.

As used herein a "control plant" means a plant that does not contain a polynucleotide sequence of the invention. Suitable control plants include the non-transgenic plant of the parental line used to generate a transgenic plant or a non-transgenic plant that is the same variety of the transgenic plant, which may generally be referred to herein as a "wild-type" plant.

As used herein an "enhanced trait" means a characteristic of a transgenic plant that includes, but is not limited to, an enhance agronomic trait characterized by enhanced plant morphology, physiology, growth and development, yield, nutritional enhancement, disease or pest resistance, or environmental or chemical tolerance. In more specific aspects of this invention enhanced trait is selected from the group of enhanced traits consisting of enhanced water use efficiency (e.g., "drought tolerance"), enhanced salinity tolerance, enhanced cold tolerance, increased yield, and enhanced nitrogen use efficiency.

As used herein, "reduced water conditions" or "non-water stressed" conditions are used interchangeably and refer to conditions in which plants or cells are grown without water limitations and for which the cell, plant, or majority of plants do not display visible signs or symptoms associated with water-deficit conditions. By contrast "restricted water conditions," "water deficit conditions" and "water stressed conditions" are used interchangeably to refer to conditions in which plants or cells are grown under water limiting conditions and for which the cell, plant, or majority of plants display visible signs or symptoms associated with drought, and water stress.

As used herein, "reduced water conditions" or "non-water stressed" conditions are used interchangeably and refer to conditions in which plants or cells are grown without water limitations and for which the cell, plant, or majority of plants do not display visible signs or symptoms associated with water-deficit conditions. By contrast "restricted water conditions," "water deficit conditions" and "water stressed conditions" are used interchangeably to refer to conditions in which plants or cells are grown under water limiting conditions and for which the cell, plant, or majority of plants display visible signs or symptoms associated with drought, and water stress.

The term "Increased yield" as used herein is intended to conform with the way this term would be typically used and understood in the fields of agriculture and/or research. Increased yield of a transgenic plant of the invention can be measured in a number of ways, including test weight, seed number per plant, seed weight, seed number or weight per unit area (e.g., seeds, or weight of seeds, per acre). In a particular embodiment, increased yield refers to a statistically significant increase in the seed or grain production weight by a plant or group of plants (per unit area). According to one embodiment, the seed or grain weight yield of a statistically significant sample size of transgenic plants of the invention (e.g., n=10 or more) is increased at least 5% when compared to the seed or grain weight yield of a comparable number of control plants.

The term "increased photosynthesis rate" as used herein is intended to conform with the way this term would be typically used and understood in the fields of agriculture and/or research. Increased photosynthesis of a transgenic plant of the invention can be measured in a number of ways, including leaf $CO_2$ gas exchange measurement. In a particular embodiment, increased photosynthesis rate refers to a statistically significant increase in leaf $CO_2$ gas exchange by a plant or group of plants (per unit area). According to one embodiment, the photosynthesis rate of a statistically significant sample size of transgenic plants of the invention (e.g., n=10 or more) is increased at least 5% when compared to the photosynthetic rate of a comparable number of control plants.

Modified HaHB4 Polynucleotides Polypeptides

The invention relates to the discovery that sequence modifications of the HaHB4 transcription factor surprisingly result in enhanced traits in transgenic plants that have been transformed with polynucleotide sequences encoding the modified HaHB4 protein. The HaHB4 gene (including promoter and regulatory sequences), protein, and HaHB4 transgenic hosts are further described and characterized in U.S. Pat. No. 7,674,955, herein incorporated by reference in its entirety.

In some embodiments, the invention provides for nucleic acid molecules comprising polynucleotide sequences encoding a modified HaHB4 protein. In additional embodiments, the invention provides for nucleic acid molecules comprising polynucleotide sequences encoding a functionally active fragment or variant of modified HaHB4 having a sequence that is distinct from HaHB4 (SEQ ID NO:2). Proteins encoded by these and other polynucleotides of the invention are also encompassed by the invention.

As disclosed herein, transgenic plants transformed with modified HaHB4 (modHaHB4) protein having the amino acid sequence of SEQ ID NO:4 and SEQ ID NO:8 unexpectedly display enhanced traits including increased yield when grown under water-stressed or non-water stressed conditions as compared to control plants. Similarly, as disclosed herein, transgenic plants transformed with modified HaHB4 (modHaHB4) protein having the amino acid sequence of SEQ ID NO:4 and SEQ ID NO:8 unexpectedly display enhanced traits including increased photosynthesis when grown under water-stressed or non-water stressed conditions as compared to control plants. Thus, in one embodiment, the invention is directed to nucleic acid molecules comprising a polynucleotide sequence encoding a modified *Hellanthux annuus* HB-4 (mod1HaHB4) protein having the amino acid sequence of SEQ ID NO:4. In a particular embodiment, the nucleic acid comprises the polynucleotide sequence of SEQ ID NO:3, SEQ ID NO:12, SEQ ID NO:13, SEQ ID NO:15 or SEQ ID NO:16. In another embodiment, the invention is directed to nucleic acid molecules comprising a polynucleotide sequence encoding a modified *Helianthus annuus* HB4 (mod2HaHB4) protein having the amino acid sequence of SEQ ID NO:8. In particular embodiments, the nucleic acid comprises the polynucleotide sequence of SEQ ID NO:14 or SEQ ID NO:17.

Transgenic plants transformed with modified HaHB4 (modHaHB4) protein having the amino acid sequence of SEQ ID NO:38 and SEQ ID NO:39 are also encompassed by the invention. In particular embodiments, these plants display enhanced traits including increased yield and/or increased photosynthesis when grown under water-stressed or non-water stressed conditions as compared to control plants. Thus, in one embodiment, the invention is directed to nucleic acid molecules comprising a polynucleotide sequence encoding a mod3HaHB4 protein having the amino acid sequence of SEQ ID NO:38. In another embodiment, the invention is directed to nucleic acid molecules comprising a polynucleotide sequence encoding a mod4HaHB4 protein having the amino acid sequence of SEQ ID NO:39.

The invention further provides polynucleotides encoding functionally active fragments of mod1HaHB4(HaHB4.2 (SEQ ID NO:4)) comprising a sequence of mod1HaHB4 that is not present in the corresponding sequence of HaHB4 (SEQ ID NO:2). In some embodiments, the functionally active fragments comprise at least 15, 20, 25, 30, 40, 50, 60, 75, 100, 125, 150, or 175 consecutive amino acid residues of the amino acid sequence of mod1HaHB4 (SEQ ID NO:4). In further embodiments, the fragments comprise 10-50, 25-75, 50-100, 75-125, or 100-175 consecutive amino acid residues of the amino acid sequence of mod1HaHB4 (SEQ ID NO:4). In additional embodiments, the fragments comprise the sequence of amino acid residues 2-10 of SEQ ID NO:4, amino acid residues 13-25 of SEQ ID:4, or amino acid residues 150-170 of SEQ ID:4.

The invention further provides polynucleotides encoding functionally active fragments of mod2HaHB4 (HaHB4.3 (SEQ ID NO:8)) comprising a sequence of mod2HaHB4 that is not present in HaHB4 (SEQ ID NO:2). In some embodiments, the functionally active fragments comprise at least 15, 20, 25, 30, 40, 50, 60, 75, 100, 125, 150, or 175 consecutive amino acid residues of the amino acid sequence of mod2HaHB4 (SEQ ID NO:8). In additional embodiments the fragments comprise 10-50, 25-75, 50-100, 75-125, or 100-175 consecutive amino acid residues of the amino acid sequence of mod2HaHB4 (SEQ ID NO:8). In additional embodiments, the fragments comprise the sequence of amino acid residues 2-10 of SEQ ID NO:8.

The invention further provides polynucleotides encoding functionally active fragments of mod3HaHB4 (HaHB4.4 (SEQ ID NO:38)) comprising a sequence of mod3HaHB4 that is not present in HaHB4 (SEQ ID NO:2). In some embodiments, the functionally active fragments comprise the sequence of amino acid residues 2-15 or 165-175 of SEQ ID NO:38 and comprise at least 15, 20, 25, 30, 40, 50, 60, 75, 100, 125, 150, or 175 consecutive amino acid residues of the amino acid sequence of mod3HaHB4 (SEQ ID NO:38). In additional embodiments the fragments the functionally active fragments comprise the sequence of amino acid residues 2-15 or 165-175 of SEQ ID NO:38 and comprise 10-50, 25-75, 50-100, 75-125, or 100-175 consecutive amino acid residues of the amino acid sequence of mod3HaHB4 (SEQ ID NO:38).

The invention further provides polynucleotides encoding functionally active fragments of mod4HaHB4 (SEQ ID NO:39)) comprising a sequence of mod4HaHB4 that is not present in HaHB4 (SEQ ID NO:2). In some embodiments, the functionally active fragments comprise the sequence of amino acid residues 2-10 of SEQ ID NO:39 and comprise at least 15, 20, 25, 30, 40, 50, 60, 75, 100, 125, 150, or 175 consecutive amino acid residues of the amino acid sequence of mod4HaHB4 (SEQ ID NO:39). In additional embodiments the fragments comprise the sequence of amino acid residues 2-10 of SEQ ID NO:39 and comprise 10-50, 25-75, 50-100, 75-125, or 100-175 consecutive amino acid residues of the amino acid sequence of mod4HaHB4 (SEQ ID NO:39).

In another embodiment, the polynucleotides of the invention encode functionally active fragments corresponding to N-terminal and/or C-terminal deletions of mod1HaHB4 (SEQ ID NO:4). Thus, according to some embodiments, the polynucleotides of the invention encode functionally active fragments of mod1HaHB4 having at least 1, but less than 5, 10, 15, or 20 amino acids deleted from the N-terminus of mod1HaHB4 (SEQ ID NO:4). In additional embodiments, the polynucleotides of the invention encode functionally active fragments of mod1HaHB4 (SEQ ID NO:4) having at least 1, but less than 10, 25, 50, 75, or 100 amino acids deleted from the C-terminus of mod1HaHB4 (SEQ ID NO:4). In further embodiments, the polynucleotides of the invention encode functionally active fragments of mod1HaHB4 having at least 1, but less than 5, 10, 15, or 20 amino acids deleted from the N-terminus and at least 1, but less than 10, 25, 50, 75, or 100 amino acids deleted from the C-terminus of mod1HaHB4 (SEQ ID NO:4).

In another embodiment, the polynucleotides of the invention encode functionally active fragments corresponding to N-terminal and/or C-terminal deletions of mod2HaHB4 (SEQ ID NO:8). Thus, according to some embodiments, the polynucleotides of the invention encode functionally active fragments of mod2HaHB4 having at least 1, but less than 5, 10, 15, or 20 amino acids deleted from the N-terminus of mod2HaHB4 (SEQ ID NO:8). In additional embodiments, the polynucleotides of the invention encode functionally active fragments of mod2HaHB4 (SEQ ID NO:8) having at least 1, but less than 10, 25, 50, 75, or 100 amino acids deleted from the C-terminus of mod2HaHB4 (SEQ DU NO:8). In further embodiments, the polynucleotides of the invention encode functionally active fragments of mod2HaHB4 having at least 1, but less than 5, 10, 15, or 20 amino acids deleted from the N-terminus and at least 1, but less than 10, 25, 50, 75, or 100 amino acids deleted from the C-terminus of mod2HaHB4 (SEQ ID NO:8).

In another embodiment, the polynucleotides of the invention encode functionally active fragments corresponding to N-terminal and/or C-terminal deletions of mod4HaHB4 (HaHB4.3 (SEQ ID NO:38)). Thus, according to some embodiments, the polynucleotides of the invention encode functionally active fragments of mod3HaHB4 having at least 1, but less than 9, 10, 15, or 20 amino acids deleted from the N-terminus of mod4HaHB4 (SEQ ID NO:38). In additional embodiments, the polynucleotides of the invention encode functionally active fragments of mod3HaHB4 (SEQ ID NO:38) having at least 1, but less than 9 amino acids deleted from the C-terminus of mod3HaHB4 (SEQ ID NO:38). In further embodiments, the polynucleotides of the invention encode functionally active fragments of mod3HaHB4 having at least 1, but less than 5, 10, 15, or amino acids deleted from the N-terminus and at least 1, but less than 10, 25, 50, 75, or 100 amino acids deleted from the C-terminus of mod3HaHB4 (SEQ ID NO:38).

In another embodiment, the polynucleotides of the invention encode functionally active fragments corresponding to N-terminal and/or C-terminal deletions of mod4HaHB4 (SEQ ID NO:39). Thus, according to some embodiments, the polynucleotides of the invention encode functionally active fragments of mod4HaHB4 having at least 1, but less than 5, 10, 15, or 20 amino acids deleted from the N-terminus of mod4HaHB4 (SEQ ID NO:39). In additional embodiments, the polynucleotides of the invention encode functionally active fragments of mod4HaHB4 (SEQ ID NO:39) having at least 1, but less than 10, 25, 50, 75, or 100 amino acids deleted from the C-terminus of mod4HaHB4 (SEQ ID NO:39). In further embodiments, the polynucleotides of the invention encode functionally active fragments of mod4HaHB4 having at least 1, but less than 5, 10, 15, or 20 amino acids deleted from the N-terminus and at least 1, but less than 7 amino acids deleted from the C-terminus of mod4HaHB4 (SEQ ID NO:39).

Regions of modHaHB4 proteins (e.g., mod1HaHB11 (SEQ ID NO:4)) and mod2HaHB11 (SEQ ID NO:8)) include the amino terminal region ("NTR": SEQ ID NO:6 or SEQ ID NO:9); homeodomain ("HD": amino acid residues 13-78 of SEQ ID NO:4; amino acid residues 12-77 of SEQ ID NO:8); leucine zipper ("LZ": amino acid residues 79-108 of SEQ ID NO:4 or amino acid residues 78-107 of SEQ ID NO:8); and the carboxy terminal region ("CTR": amino acid residues 109-177 of SEQ ID NO:4 or amino acid residues 108-176 of SEQ ID NO:8). According to some embodiments, the polynucleotides include proteins comprising one or more regions of the mod1HaHB4 protein selected from the group consisting of: the NTR (SEQ ID NO:6 or SEQ ID NO:9), homeodomain (amino acid residues 13-78 of SEQ ID NO:4 or amino acid residues 12-77 of SEQ ID NO:8); leucine zipper (amino acid residues 79-108 of SEQ ID NO:4; or amino acid residues 78-107 of SEQ ID NO:8); and CTR (amino acid residues 109-177 of SEQ ID NO:4 or amino acid residues 108-176 of SEQ ID NO:8). Also provided are polynucleotides encoding any combination of two or more modHaHB4 regions selected from the group consisting of: the NTR (SEQ ID NO:6 or SEQ ID NO:9), homeodomain (amino acid residues 13-78 of SEQ ID NO:4); leucine zipper (amino acid residues 79-108 of SEQ ID NO:4); and CTR (amino acid residues 109-177 of SEQ ID NO:4).

Regions of mod3HaHB4 protein (SEQ ID NO:38) include the homeodomain ("HD": amino acid residues 13-78 of SEQ ID NO:38); the carboxy terminal region ("CTR": amino acid residues 109-177 of SEQ ID NO:38). According to some embodiments, the polynucleotides include proteins comprising one or more regions of the mod3HaHB4 protein selected from the group consisting of: the homeodomain (amino acid residues 13-78 of SEQ ID NO:38; and CTR (amino acid residues 109-177 of SEQ ID NO:38).

In additional embodiments, the invention encompasses polynucleotides encoding functionally active variants of mod1HaHB4 (SEQ ID NO:4) or mod2HaHB4 (SEQ ID NO:8), wherein the sequence of the variant is not that of HaHB4 (SEQ ID NO:2). In additional embodiments, the invention encompasses polynucleotides encoding functionally active variants of mod3HaHB4 (SEQ ID NO:38) or mod4HaHB4 (SEQ ID NO:39), wherein the sequence of the variant is not that of HaHB4 (SEQ ID NO:2). Variants of the invention include additions, substitutions in the sequences of mod1HaHB4 or mod2HaHB4. Variants of the invention include additions, substitutions in the sequences of mod3HaHB4 or mod4HaHB4. Amino acid "substitutions" can result in replacing one amino acid with another amino acid having similar structural and/or chemical properties, e.g., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are generally in the range of about 1 to about 20 amino acids, more specifically about 1 to about 10 amino acids, and even more specifically, about 2 to about 5 amino acids. Non-conservative substitutions entail exchanging a member of one of these classes for another class. For example, amino acid substitutions can also result in replacing one amino acid with another amino acid having different structural and/or chemical properties, for example, replacing an amino acid from one group (e.g. polar) with another amino acid from a different group (e.g., basic). The variation allowed may be experimentally determined by systematically making insertions, deletions, or substitutions of amino acids in a polypeptide molecule using recombinant DNA techniques and assaying the resulting recombinant variants for activity.

In particular embodiments, the polynucleotides of the invention encode functionally active variants of mod1HaHB4 or mod2HaHB4 that contain 1, 2, 3, 4, 5, 10, or more substitutions, insertions, or deletions when compared to the corresponding sequence of mod1HaHB4 protein (SEQ ID NO:4) or mod2HaHB4 protein (SEQ ID NO:8), wherein the variants do not contain the corresponding amino acid sequence of HaHB4 (SEQ ID NO:2). In some embodiments, the polynucleotides encode functionally active variants of mod1HaHB4 or mod2HaHB4 that contain 1, 2, 3, 4, 5, 10, or more conservative substitutions when compared to the corresponding sequence of mod1HaHB4 protein (SEQ ID NO:4) or mod2HaHB4 protein (SEQ ID NO:8). In further embodiments, the polynucleotides encode functionally active variants of mod1HaHB4 or mod2HaHB4 that contain 1, 2, 3, 4, 5, 10, or more non-conservative substitutions when compared to the corresponding sequence of mod1HaHB4 protein (SEQ ID NO:4) or mod2HaHB4 protein (SEQ ID NO:8).

In additional embodiments, the polynucleotides encode functionally active variants of mod1HaHB4 or mod2HaHB4 protein that contain 1-10, 1-20 or 1-25 substitutions, insertions, or deletions when compared to the corresponding sequence of mod1HaHB4 protein (SEQ ID NO:4) or mod2HaHB4 protein (SEQ ID NO:8), wherein the variants do not contain the corresponding amino acid sequence of HaHB4 (SEQ ID NO:2). In some embodiments, the polynucleotides encode functionally active variants of mod1HaHB4 or mod2HaHB4 protein that contain 1-10, 1-20 or 1-25 conservative substitutions when compared to the corresponding sequence of mod1HaHB4 protein (SEQ ID NO:4) or mod2HaHB4 protein (SEQ ID NO:8). In additional embodiments, the polynucleotides encode functionally active variants of mod1HaHB4 or mod2HaHB4 protein that contain 1-10, 1-20 or 1-25 non-conservative substitutions when compared to the corresponding sequence of mod1HaHB4 protein (SEQ ID NO:4) or mod2HaHB4 protein (SEQ ID NO:8).

In particular embodiments, the polynucleotides encode functionally active variants of mod1HaHB4 protein that contain an insertion of a serine at position 7, a substitution of threonine with serine at position 9, substitution of arginine with lysine at position 18, or substitution of lysine with phenylalanine at position 155.

In particular embodiments, functionally active modified HaHB4 protein that contain substitution of threonine with serine at position 9 of native HaHB4 protein (SEQ ID NO:2), substitution of threonine with serine at position 13 of native HaHB4 protein (SEQ ID NO:2), substitution of lysine with arginine at position 22 of native HaHB4 protein (SEQ ID NO:2), substitution of phenylalanine with lysine at position 159 of native HaHB4 protein (SEQ ID NO:2), or substitution of leucine at position 175 of native HaHB4 protein (SEQ ID NO:2).

In additional embodiments, the invention encompasses polynucleotides encoding functionally active variants of mod1HaHB4 protein wherein said variant comprises an amino acid sequence that is at least 80%, 85%, 90%, 92%, 95%, 95%, 96%, 97%, 98%, or 99% identical to the amino acid sequence of mod1HaHB4 protein (SEQ ID NO:4), and wherein the variants do not contain the corresponding amino acid sequence of HaHB4 (SEQ ID NO:2). Further, suitable polynucleotide fragments having the above homologies encode a polypeptide having at least 50 amino acids, at least 100 amino acids, at least 150 amino acids, wherein the corresponding sequence is not present in HaHB4 (SEQ ID NO:2). Suitable polynucleotide fragments having the above homologies encode a polypeptide having at least 50 amino acids, at least 100 amino acids, at least 150 amino acids and do not contain the corresponding amino acid sequence of HaHB4 (SEQ ID NO:2).

In additional embodiments, the invention encompasses polynucleotides encoding functionally active variants of mod2HaHB4 protein, wherein said variant comprises an amino acid sequence that is at least 80%, 85%, 90%, 92%, 95%, 95%, 96%, 97%, 98%, or 99% identical to the amino acid sequence of mod2HaHB4 protein (SEQ ID NO:8), and wherein the variants do not contain the corresponding amino acid sequence of HaHB4 (SEQ ID NO:2). Suitable polynucleotide fragments having the above homologies encode a polypeptide having at least 50 amino acids, at least 100 amino acids, or at least 150 amino acids and do not contain the corresponding amino acid sequence of HaHB4 (SEQ ID NO:2).

In further embodiments, the invention encompasses a polynucleotide variant that is at least 80%, 85%, 90%, 92%. 95%, 95%, 96%, 97%, 98%, or 99% identical to the polynucleotide sequence of SEQ ID NO:3, SEQ ID NO:12, SEQ ID NO:13, SEQ ID NO:15 or SEQ ID NO:16 SEQ ID NO:14, or SEQ ID NO:17, or the complementary strand of any of these sequences, or fragments thereof, wherein the polynucleotide sequence is not present in the corresponding polynucleotide sequence of HaHB4 (SEQ ID NO:1) and does not encode HaHB4 (SEQ ID NO:2). Suitable polynucleotide fragments having the above homologies include fragments that are at least 20 nucleotides, at least 30 nucleotides, at least 40 nucleotides, at least 50 nucleotides, at least 75 nucleotides, or at least 100 nucleotides in length.

In an additional embodiment, the invention encompasses a nucleic acid molecule comprising a polynucleotide sequence encoding (a) mod1HaHB4 (SEQ ID NO:4); (b) a functionally active fragment of said modified protein wherein the amino acid sequence of said fragment is absent in HaHB4 (SEQ ID NO:2); or (c) a functionally active variant of modified HaHB4 protein wherein said variant comprises an amino acid sequence that is at least 80%, 85%, 90%, 95%, 96%, 97%, 98%, or 99% identical to the amino acid sequence of SEQ ID NO:4; wherein the amino acid sequence of said fragment or variant is not present in the HaHB4 amino acid sequence of SEQ ID NO:2.

In another embodiment, the invention encompasses a nucleic acid molecule comprising a polynucleotide sequence encoding (a) mod1HaHB4 (SEQ ID NO:4); (b) a functionally active fragment of mod1HaHB4 wherein the amino acid sequence of said fragment is absent in HaHB4 (SEQ ID NO:2); or (c) a functionally active variant of mod1HaHB4 wherein said variant comprises an amino acid sequence that is at least 80%, 85%, 90%, 95%, 97%, 98%, or 99% identical to the amino acid sequence of SEQ ID NO:4 and wherein the amino acid sequence of said fragment or variant is not present in the HaHB4 (SEQ ID NO:2).

The invention further provides for nucleic acids comprising a polynucleotide sequence (including fragments of modHaHB4 encoding polynucleotides described herein) that hybridizes under stringent hybridization conditions, to a nucleic acid containing a complementary strand of a polynucleotide encoding mod1HaHB4 (SEQ ID NO:4) or mod2HaHB4 (SEQ ID NO:8), wherein the hybridizing polynucleotides encode a functionally active polypeptide that is not HaHB4 (SEQ ID NO:2). In additional embodiments, polynucleotides hybridize under stringent hybridization conditions, to a nucleic acid containing a complementary strand of the polynucleotide sequence of SEQ ID NO:3 or SEQ ID NO:14, wherein the hybridizing polynucleotide encodes a functionally active polypeptide that is not HaHB4 (SEQ ID NO:2).

As used herein, a polynucleotide that is "hybridizable" to another polynucleotide or nucleic acid fragment, such as a cDNA, genomic DNA, or RNA molecule, when a single-stranded form of the polynucleotide or nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. Molecular Cloning: A Laboratory Manual, $2^{nd}$ ed., Cold Spring Harbor Laboratory: Cold Spring Harbor, N.Y. (1989), particularly Chapter 11 and Table 11.1 therein (which is incorporated by reference in its entirety). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2×SSC, 0.5% SDS was increased to 60° C. Yet another set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. In another embodiment, a minimum length for a hybridizable nucleic acid is at least about 15 nucleotides. In yet another embodiment, a minimum length for a hybridizable nucleic acid is at least about 20 nucleotides or at least about 30 nucleotides. Furthermore, the skilled artisan will recognize that the temperature and wash solution salt concentration may be adjusted as necessary according to factors such as length of the probe.

Standard recombinant DNA and molecular cloning techniques used herein are well known in the art and are described by Sambrook, J., Fritsch, B. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-Interscience (1987); Frohman (Frohman Cloning PCR products. In The Polymerase Chain Reaction, eds. K. B. Mullis, F. Fre, & R. A. Gibas, pages 14-37; each of which is incorporated by reference in its entirety), to generate proteins having a different amino acid sequence, for example to create amino acid substitutions, deletions, and/or insertions.

Vectors and Host Cells

Vectors (including expression cassettes) containing the modHaHB4 polynucleotides are also encompassed by the invention.

Vectors of the invention may be composed of DNA or RNA, and may be linear or a closed circular plasmid. The vectors may be cloning, amplification, shuttle, or expression vectors. The vector system may be a single vector or plasmid or two or more vectors that together contain or control the replication, integration and/or expression of the polynucleotides of the invention in the host cell. The polynucleotides of the invention can be inserted into the vector in either a forward or reverse orientation with respect to any particular promoter sequence contained in the vector.

Vector components for host cell transformation (e.g., bacterial or plant) generally include, but are not limited to, one or more of the following: a signal sequence, an origin of replication, one or more selectable marker genes, and optionally a promoter, such as an inducible promoter, allowing the expression of exogenous DNA. Generally, selectable marker genes encode a protein necessary for the survival or growth of transformed host cells grown in a selective culture medium. Typical selection genes encode proteins that confer resistance to antibiotics or other toxins (e.g., ampicillin, kanamycin, tetracycline, neomycin, trimethoprim, streptomycin, sulfonamides or methotrexate), (b) complement auxotrophic deficiencies, or (c) supply critical nutrients not available from complex media. Those cells that are successfully transformed with a heterologous protein or fragment thereof produce a protein conferring drug resistance and thus survive the selection regimen.

Construction of suitable vectors containing one or more of the above-listed components and the polynucleotides of the invention employs standard recombinant DNA techniques and can be readily prepared using methods and reagents available in the art. See, e.g., Sambrook et al., supra, and Ausubel et al., supra. Generally, isolated nucleic acid plasmids or DNA fragments are routinely cleaved, tailored, and re-ligated to form a vector construct containing the necessary associated components so as to provide the construct with desired function and properties. Numerous suitable vectors and promoters are commercially available and/or known in the art and can routinely be used or modified for use according to the invention. Representative examples of bacterial vectors include: pQE70, pQE80L, pQF81L, pQE82L, pQE60, and pQE-9 (Qiagen); pBS, pD10, phagescript, psiX174, pBS® SK, pBS® KS, pNH8A, pNH16a, pNH18A, pNH46A; pGEX-3X, pGEX-4T-1 to pGEX-4T-3, pGEX-5X-1 to pGEX-5X-3, and pGEX-6P-1 to pGEX-6P-3; pBluescript SK and pBluescript KS, and pBluescript II (Stratagene, La Jolla, Calif.), pIN vectors (Van Heeke and Schuster, 1989), pTRC99a, pKK223-3, pKK233-3, pDR540, and pRIT5 (Pharmacia Uppsala, Sweden). Representative examples of eukaryotic vectors include: pWLNEO, pSV2CAT, pOG44, pXT1, pSG (Stratagene), pSG5, pSVK3, pBPV, pMSB, pSVL, GEM1 (Promega Biotec, Madison, Wis.) and pSVLSV40.

In some embodiments, polynucleotides of the invention are inserted into a vector in operable linkage with a suitable promoter that functions in a host plant to drive expression of the polynucleotide sequence. Many vectors are known in the art for this purpose and can be routinely selected for construction and used according to the invention based on factors that include, for example, the size of polynucleotide sequence to be inserted into the vector and the particular host cell to be transformed with the vector. Plant transformation vectors of the invention may also contain a functional HaHB4 or heterologous intron sequence positioned either upstream of the coding sequence or even within the coding sequence of the polynucleotides of the invention, and may also contain a five prime (5') untranslated leader sequence (i.e., a UTR or 5'-UTR) positioned between the promoter and the point of translation initiation.

The vectors of the invention preferably contain a selectable marker that confers a selectable phenotype that allows for the identification of transformed cells that express and/or contain the polynucleotides of the invention. For example, in various embodiments, the selectable marker gene encodes a protein conferring biocide resistance, antibiotic resistance (e.g., kanamycin, G418 bleomycin, hygromycin, etc.), or herbicide resistance (e.g., glyphosate, etc.). Examples of selectable markers that may be used according to the compositions and methods of the invention include, but are not limited to, a neo gene which codes for kanamycin resistance and can be selected for using kanamycin, the nptII gene, which confers resistance to kanamycin and related antibiotics (Messing et al., Gene 19:259-268 (1982); Bevan et al., Nature 304:184-187 (1983)), the bar gene, which confers resistance to the herbicide phosphinothricin (White et al., Nucl. Acids Res. 18:1062 (1990), Spencer et al., Theor. Appl. Genet. 79:625-631 (1990)), the hph gene, which confers resistance to the antibiotic hygromycin (Blochinger et al., Mol. Cell. Biol. 4:2929-2931 (1984); G418, a mutant EPSP synthase gene which encodes resistance to glyphosate (U.S. Pat. Nos. 4,940, 835 and 5,188,642); a mutant acetolactate synthase gene (ALS) which confers imidazolinone or sulfonylurea resistance; a nitrilase gene which confers resistance to bromoxynil; and a methotrexate resistant DHFR gene. Additionally, multiple selectable markers are available for conferring resistance to ampicillin, bleomycin, chloramphenicol, gentamycin, hygromycin, kanamycin, lincomycin, methotrexate, phosphinothricin, puromycin, spectinomycin, rifampicin, and tetracycline. Examples of such selectable markers are illustrated in U.S. Pat. Nos. 5,550,318; 5,633,435; 5,780.708 and 6,118,047 the entire contents of each of which is incorporated by reference in its entirety.

According to some embodiments, the invention is directed to nucleic acids, including vectors and expression cassettes, comprising the polynucleotides of the invention operably associated with a promoter. In some embodiments, the polynucleotides of the invention are operably associated with a constitutive promoter. In particular embodiments, the constitutive promoter is the 35S CaMV promoter or the Ubi promoter. According to other embodiments, the polynucleotides of the invention are operably associated with an inducible promoter. In particular embodiments, the inducible promoter is a stress-inducible promoter. In further embodiments, the inducible promoter is the modified version of HaHB4 promoter fused with the first intron of *Arabidopsis* Cox2-c.

In additional embodiments, the vectors of the invention contain the HaHB4 small allele promoter sequence (SEQ ID NO:20), the HaHB4 large allele promoter sequence (SEQ ID NO:21), or a functionally active fragment or derivative of the HaHB4 promoter large or small allele promoter sequence. According to one embodiment, the promoter comprises the sequence of nucleotides 805 to 1221, 904 to 1221, 1011 to 1221, or 15 to 622 of the HaHB4 small allele promoter sequence (SEQ ID NO:20). According to another embodiment, the promoter comprises the sequence of polynucleotides 15-409 or 805 to 1221 of the HaHB4 large allele promoter sequence (SEQ ID NO:21). According to another embodiment, the promoter comprises the sequence of polynucleotides 15-409 or 805 to 1221 of the HaHB4 large allele promoter sequence (SEQ ID NO:21). In another embodiment, the promoter comprises the sequence of a fragment of at least 50, 100, 150, 200, 250, 300, 350, 400, 450, 500, 600, 700, or 800 nucleotides of the of the HaHB4 small allele promoter sequence (SEQ ID NO:20). In an additional embodiment, the promoter comprises the sequence of a fragment of at least 50, 100, 150, 200, 250, 300, 350, 400, 450, 500, 600, 700, or 800 nucleotides of the HaHB4 large allele promoter sequence (SEQ ID NO:21).

Numerous additional promoters that are active in plant cells are known in the art and are provided in plant expression vectors according to various embodiments of the invention. These promoters include promoters present in plant genomes as well as promoters from viruses, bacteria and other sources, including nopaline synthase (NOS) promoter and octopine synthase (OCS) promoters carried on tumor-inducing plasmids of *A. tumefaciens* and caulimovirus promoters such as the cauliflower mosaic virus or Figwort mosaic virus promoters. See, for example, U.S. Pat. Nos. 5,858,742 and 5,322,938 which disclose versions of the constitutive promoter derived from cauliflower mosaic virus (CaMV35S), U.S. Pat. No. 5,378,619 which discloses a Figwort Mosaic Virus (FMV) 35S promoter, U.S. Pat. No. 6,437,217 which discloses a maize RS81 promoter), U.S. Pat. No. 5,641,876 which discloses a rice actin promoter, U.S. Pat. No. 6,426,446 which discloses a maize RS324 promoter, U.S. Pat. No. 6,429,362 which discloses a maize PR-1 promoter, U.S. Pat. No. 6,232,526 which discloses a maize A3 promoter, U.S. Pat. No. 6,177,611 which discloses constitutive maize promoters, U.S. Pat. No. 6,433,252 which discloses a maize L3 oleosin promoter, U.S. Pat. No. 6,429,357 which discloses a rice actin 2 promoter and intron, U.S. Pat. No. 5,837,848 which discloses a root specific promoter, U.S. Pat. No. 6,084,089 which discloses cold inducible promoters, U.S. Pat. No. 6,294,714 which discloses light inducible promoters, U.S. Pat. No. 6,140,078 which discloses salt inducible promoters, U.S. Pat. No. 6,252,138 which discloses pathogen inducible promoters, U.S. Pat. No. 6,175,060 which discloses phosphorus deficiency inducible promoters, U.S. Appl. Publ. No. 2002/0192813A1 which discloses 5', 3' and intron elements useful in the design of effective plant expression vectors, U.S. application Ser. No. 09/078,972 which discloses a coixin promoter, U.S. application Ser. No. 09/757,089 which discloses a maize chloroplast aldolase promoter, and U.S. application Ser. No. 10/739,565 which discloses water-deficit inducible promoters, each of which is herein incorporated by reference. These and numerous other promoters that function in plant cells are known in the art and may be operably linked to the polynucleotides of the invention and or used in the vectors of the invention to drive and control the expression of the polynucleotide sequences in transgenic plant cells.

In additional embodiments, the polynucleotides of the invention (alone or in association with vector sequence) are operably linked to a promoter derived from the regulatory region of a plant gene that is over expressed in water deficit conditions. In particular embodiments, polynucleotides of the invention are operably linked to a promoter derived from the 5' regulatory region corresponding to a gene selected from: heat shock protein 17.5 (HSP17.5), HVA22 (HVA22), Rab17, or cinnamic acid 4-hydroxylase (CA4H). Exemplary water-deficit-inducible promoters are disclosed in U.S. application Ser. No. 10/739,565, which is herein incorporated herein by reference in its entirety.

In further embodiments, the polynucleotides of the invention are operably linked to a promoter that is in turn operably linked to one or more "enhancer sequences" that elevates the gene expression driven by the promoter. Such enhancers can often be inserted in the forward or reverse orientation 5' or 3' to the coding sequence and may be present in intron. Numerous enhancers are known and/or can readily be identified using reagents and techniques known in the art. Exemplary enhancers that may be operably associated with the polynucleotides of the invention include the 5' introns of the rice actin 1 and rice actin 2 genes, and elements from the CaMV 35S promoter (Odell et al., Nature 6:810-812 (1985), octopine synthase genes, the maize alcohol dehydrogenase gene, the maize shrunken 1 gene, the Adh intron 1 (Callis et al., Genes and Develop., 1:1183 (1987)), sucrose synthase intron (Vasil et al., Plant Physiol. 91:1575 (1989)) and TMV omega element (Gallie et al., Plant Cell 1:301 (1989)).

In additional embodiments, the polynucleotides of the invention (alone or in association with vector sequence) are operably linked to a transcription terminator that is responsible for terminating transcription beyond the polynucleotides of the invention and correct mRNA polyadenylation. Exemplary suitable transcriptional terminators known to function in plants include, but are not limited to, the CaMV 35S terminator, the tml terminator, the nopaline synthase terminator derived from *A. tumefaciens* (kBvan et al., Nucl. Acids Res., 11:369 (1983), Depicker et al., J. Mol. Appl. Genet. 1:561-573 (1982)), the pea rbcS E9 terminator, the terminator for the T7 transcript from the octopine synthase gene of *A. tumefaciens*, and the 3' end of the protease inhibitor I or II genes from potato or tomato.

Preferred plant transformation vectors include those derived from a Ti plasmid of *A. tumefaciens* (e.g. as described in U.S. Pat. Nos. 5,981,840, 5,501,967, 4,536,475, 4,658,082, 4,693,977, and 4,886,937, and Simpson et al., Plant Mol. Biol. 6:403-15 (1986) and EP 0 122 791)), the contents of each of which is incorporated by reference in its entirety). Other preferred plant transformation vectors include those disclosed, e.g., by Herrera-Estrella et al., Nature 303:209-213 (1983); Bevan, M., Nucl. Acids Res. 12: 8711-8721 (1984), and EP 0 120 516, the contents of each of which is incorporated by reference in its entirety. For *A. tumefaciens* based plant transformation system, additional elements present in the transformation vector construct include T-DNA left and right border sequences to facilitate incorporation of the recombinant polynucleotide into the plant genome. Descriptions of the *Agrobacterium* vector systems and methods for *Agrobacterium*-mediated gene transfer are provided in for example, Gruber et al., "Vectors for Plant Transformation," in Methods in Plant Molecular Biology and Biotechnology supra; and Moloney et al., Plant Cell Reports 8:238 (1989). According to further embodiments the vectors are part of binary vector system, such as pBin19, pC22, pGA482, pCV001, pJJ1881, pPZP111, pPVP, pGreen0029, pCGN1547, pMON10098, pBI121 (Bevan, Nucl. Acids Res. 12:8711-8721 (1984), pBI101 (Jefferson et al., EMBO J. 6:3901-3907 (1987)) Risch et al., Plant Mol. Biol. 27:405-409 (1995), and Rothstein et al., Gene 53:153-161 (1987)), see also, Becker et al., Plant Mol. Biol. 20:1195-1197 (1992) and Hajdukiewicz et al. Plant Mol. Biol. 25:989-994 (1994), each of which is incorporated by reference in its entirety).

Additional vectors (including expression cassettes) and in vitro culture methods and reagents for plant cell or tissue transformation and regeneration of plants are known in the art and can readily be applied or modified to practice the invention. The cloning, nucleic acid manipulation and synthesis, vector constructions and other recombinant techniques necessary to make and use the polynucleotides, polypeptides, host cells, and transgenic plants of the invention are generally known in the art, for example, as described in Sambrook et al., Molecular Cloning: A Laboratory Manual. 2nd Edition, Cold Spring Harbor, N.Y., Cold Spring Harbor Laboratory Press (1989); and Ausubel et al., Current Protocols in Molecular Biology, John Wiley & Sons. New York, N.Y., (1989); and Kriegler, Gene Transfer and Expression: A Laboratory Manual (1990), which is incorporated by reference in its entirety In general it may be preferred to introduce a functional recombinant DNA at a non-specific location in a plant genome. In special cases it may be useful to insert a recombinant DNA construct by site-specific integration. Several site-specific recombination systems exist which are known to function in plants include cre-lox as disclosed in for example, U.S. Pat. No. 4,959,317 and FLP-FRT as disclosed in U.S. Pat. No. 5,527,695, the contents of both of which are incorporated by reference in its entirety.

The invention also provides host cells comprising the vectors (including expression cassettes) and/or polynucleotides of the invention. Host cells comprising polynucleotides of the invention include, but are not limited to, bacterial (e.g., *E. coli*), fungal, insect, plant and animal cells. The polynucleotides of the invention may be integrated into the host cellular genome or exist in the host extrachromosomally (e.g., an autonomously replicating plasmid with an origin of replication). According to some embodiments, polynucleotide sequence of the invention is operably linked to a promoter.

Suitable methods for transformation of host cells for use with the current invention are believed to include virtually any method known in the art by which DNA can be introduced (transiently or stably) into a cell. For example, polynucleotides of the invention can routinely be transformed into the bacterial host cells, such as *E coli*, and other hosts by calcium phosphate transfection, DEAE-Dextran mediated transfection, or electroporation (Davis et al., Basic Methods in Molecular Biology (1986)).

Alternatively, host cells may be transformed with polynucleotides of the invention using techniques such as, direct uptake of DNA into protoplasts using $CaCl_2$ precipitation, polyvinyl alcohol, or poly-L-ornithine (see, e.g., Hain et al., Mol. Gen. Genet. 199:161 (1985); and Draper et al., Plant Cell Physiol. 23:451 (1982)).

In additional embodiments, host cells are transformed with polynucleotides of the invention using a technique known in the art. Exemplary techniques for transforming hosts cells include protoplast transformation (see, e.g., U.S. Pat. No. 5,508,184), microinjection (Crossway, et al., Biotechniques 4:320-334 (1986); and U.S. Pat. No. 6,300,543), electroporation (Riggs et al., Proc. Natl. Acad. Sci. USA 83:5602-5606 (1986) Fromm, et al., Proc. Natl. Acad. Sci. USA 82:5824-5828 (1985)), direct gene transfer (Paszkowski et al., EMBO J. 3:2717-2722 (1984)), sonication methods (Bao et al., Ultrasound in Medicine & Biology 23:953-959 (1997); Finer et al. Lett. Appl. Microbiol. 30:406-10 (2000); Amoah et al., J. Exp. Bot. 52:1135-42 (2001)); polyethylene glycol methods (Krens et al., Nature 296:72-77 (1982)); desiccation/inhibition-mediated DNA uptake (Potrykus et alt, Molec. Genet. 199:183 (1985), electroporation (U.S. Pat. No. 5,384,253), agitation with silicon carbide fibers (U.S. Pat. Nos. 5,302,523 and 5,464.765), by *Agrobacterium*-mediated transformation (U.S. Pat. Nos. 5,563,055; 5,591,616; 5,693,512; 5,824,877; 5,981,840; 6,384,301) and by DNA coated microprojectile bombardment (U.S. Pat. Nos. 6,399,861; 6,160,208; 6,403, 865; 5,015,580; 5,550,318; 5,538,880; 4,945,050; Int. App. Pub. No. WO 91/10725; and McCabe et al., Biotechnology 6:923-926 (1988)), Sanford, Physiol. Plant 79:206 (1990); and Klein et al., Biotechnology 10:268 (1992)), Tomes et al., "Direct DNA Transfer into Intact Plant Cells Via Microprojectile Bombardment" pp. 197-213 in Plant Cell, Tissue and Organ Culture, Fundamental Methods, eds. O. L. Gamborg & G. C. Phillips. Springer-Verlag Berlin Heidelberg New York, 1995; Padgette et al., 1995).

In the case of multicellular species, the transgenic cells may be regenerated into transgenic organisms using techniques known in the art such as those described in, Christou et al. Plant Physiol. 87:671-674 (1988) (soybean); Datta et al., Biotechnology 8:736-740 (1990) (rice); Klein et al., Proc. Natl. Acad. Sci. USA 85:4305-4309 (1988) (maize); Klein et al., Biotechnology 6:559-563 (1988) (maize); int. App. Pub. No. WO91/10725 (maize): Klein et al., Plant Physiol. 91:440-444 (1988) (maize); and Gordon-Kamm et al., Plant Cell 2:603-618 (1990) (maize).

The polynucleotides of the invention can generally be introduced (transiently or stably) into plants by one or more techniques typically used for direct delivery into cells. Such protocols may vary depending on the type of plant e.g., monocot or dicot) and the plant pert targeted for gene modification. Numerous methods for producing plant cell nuclei with recombinant DNA are known and may be used according to the invention. Two commonly used methods for plant transformation are *Agrobacterium*-mediated transformation and microprojectile bombardment. Exemplary microprojectile bombardment methods are disclosed in U.S. Pat. No. 5,015, 580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn) and U.S. Pat. No. 6,153,812 (wheat). Exemplary *Agrobacterium*-mediated transformation methods are described in U.S. Pat. No. 5,159,135 (cotton); U.S. Pat. No. 5,824,877 (soybean); U.S. Pat. No. 5,591,616 (corn); and U.S. Pat. No. 6,384,301 (soybean), and Horsch et al., Science 227:1229-31 (1985)), the contents of each of which is incorporated by reference in its entirety. In additional embodiments, *Agrobacterium* mediated transformation is performed according to the methods disclosed in Hofgen et al., Nucleic Acid Research 16: 9977 (1998), or using an immersion method (floral dip), such as described by Clough et al., Plant J. 16:735-743 (1998), the contents each of which is incorporated by reference in its entirety.

Plant cell recipients of the polynucleotides of the invention include, but are not limited to, plant cell culture, meristem cells, callus, immature embryos and pollen and egg cells. According to some embodiments, the host plant cell is a dicot.

According to other embodiments, the host plant cell is a monocot. Once transformed, the plant cells can be used to regenerate transgenic plants. Exemplary transformation reagents and methods for making transgenic plants are described for example, in U.S. Pat. Nos. 6,194,636, 6,232,526, and 4,658,082, and Shahin, Theor. Appl. Genet. 69:235-40 (1985); the contents of each of which is incorporated by reference in its entirety.

Transgenic plants seed, pollen and plant parts comprising a polynucleotide or polypeptide of the invention are encompassed by the invention. In some embodiments, the polynucleotides of the invention are integrated into the transgenic plant DNA. In specific embodiments, the polynucleotides of the invention are stably integrated into the host genomic DNA. In additional embodiments the polynucleotides of the invention exist extrachromosomally (e.g., an autonomously replicating plasmid with an origin of replication) within the plant host cell. According to some embodiments, the polynucleotides of the invention are operably linked to a promoter. In further embodiments, at least one cell in a transgenic plant, plant cell, seed, pollen or plant part expresses or is capable of expressing a polypeptide of the invention. In yet a further embodiment, a least one cell in a transgenic plant, plant cell, seed, pollen or plant part expresses or is capable of expressing a protein of the invention that is capable of binding endogenous noncoding DNA sequence of the host plant cell in vitro.

"Host" plants, plant cells, seed, pollen and plant parts that can be used and produced according to the methods of the invention (as well as their sexually or asexually reproduced progeny) include virtually any plant species into which polynucleotides of the invention can be introduced (transiently or stably). Host plants and host plant cells of the invention include, crop plants or plants used to produce food or feed. According to some embodiments, the host plant, plant cell, seed, pollen and plants part is a monocot. In some embodiments, the host plant, plant cell, seed, pollen, plants part, or transgenic product thereof is soybean (*Glycine max*). In some embodiments, the host plant, plant cell, seed, pollen, plants part, or transgenic product thereof is wheat (*Triticum aestivum*). In additional embodiments, the host plant, plant cell, seed, pollen, plants part, or transgenic product thereof is corn (*Zea mays*). In additional embodiments, the host plant, plant cell, seed, pollen, plants part, or transgenic product thereof is rice (*Oryza sativa*). In further embodiments, the host plant, plant cell, seed, pollen, plants part, or transgenic product thereof is cotton (*Gossypium barbadense, Gossypium hirsutum*). In other embodiments, the host plant, plant cell, seed, pollen, plants part, or transgenic product thereof is sugarcane (*Saccharum* spp.). In additional embodiments, the host plant, plant cell, seed, pollen, plants part, or transgenic product thereof is *Arabidopsis* (e.g., *Arabidopsis thaliana*).

According to additional embodiments, the host plant, plant cell, seed, pollen, plants part, or transgenic product thereof is a selected from the group consisting of: alfalfa (*Medicago sativa*), *Brassica* sp. (e.g., *B. napus, B. rapa, B. juncea*): particularly those *Brassica* species useful as sources of seed oil including, canola, sunflower (*Helianthus annuus*), safflower (*Carthamus tinctorius*), peanuts (*Arachis hypogaea*, sorghum (*Sorghum bicolor, Sorghum vulgare*), oat, rye (*Secale cereale*), millet (e.g., pearl millet (*Pennisetum glaucum*), proso millet (*Panicum miliaceum*), foxtail millet (*Setaria italica*), finger millet (*Eleusine coracana*), tobacco (*Nicotiana tabacum*), barley (*Hordeum*), oats (*Avena sativa*), tomatoes (*Lycopersicon esculentum*), squash, melons (e.g., musk melon (*C. melon*), and cantaloupe (*C. cantalupensis*)), sugarcane (*Saccharum* spp.), a legume crop other than soybean, and starchy tuber/roots, e.g., potato (*Solanum tuberosum*), sweet potato (*Ipomoea batatus*), cassaya (*Manihot esculenta*), taro, *canna*, and sugar beets (*Beta vulgaris*).

In further embodiments, the host plant, plant cell, seed, pollen, plants part, or transgenic product thereof is a vegetable. Vegetable host cells (plants) of the invention include, for example, lettuce (e.g., *Lactuca saliva*), green beans (*Phaseolus vulgaris*), lima beans (*Phaseolus limensis*), peas (*Lathyrus* spp.), and members of the genus *Cucumis* such as cucumber (*C. sativus*).

In other embodiments, the host plant, plant cell, seed, pollen, plants part, or transgenic product thereof is selected from the group consisting of: coffee (*Cofea* spp.), coconut (*Cocos nucifera*), pineapple (*Anana comosus*), citrus trees (*Citrus* spp.), cocoa (*Theobroma cacao*), tea (*Camellia sinensis*), banana (*Musa* spp.), avocado (*Persea ameericana*), fig (*Ficus casica*), guava (*Psidium guajava*), mango (*Mangijera indica*), olive (*Olea europaea*), papaya (*Carica papaya*), cashew (*Anacardium occidentale*), macadamia (*Macadamia integrifolia*), and almond (*Prunus amygdalus*).

Seed, pollen, tissue, cells and progeny of the transgenic plants and cells of the invention are also within the scope of the invention.

In one embodiment, the invention encompasses a transgenic plant transformed with a nucleic acid molecule comprising the polynucleotide sequence of the invention, wherein the polynucleotide sequence is expressed so as to produce a recombinant protein in the plant and wherein the recombinant protein provides an increased yield of the plant as compared to a wild type variety of the plant under the same conditions. According to some embodiments, the plant is a monocot. In another embodiment, the plant is maize. In an additional embodiment, the plant is wheat. In another embodiment, the plant is rice. According to other embodiments, the transgenic plant is a dicot. In one embodiment, the transgenic plant is soybean. In an additional embodiment, the transgenic plant is *Arabidopsis*.

In another embodiment, the invention encompasses a transgenic plant seed transformed with a nucleic acid molecule comprising the polynucleotide sequence of the invention, wherein the polynucleotide sequence is expressed so as to produce a recombinant protein in the plant seed and wherein said recombinant protein provides an increased tolerance to drought as compared to a wild type variety of the plant seed under the same conditions. According to some embodiments, the transgenic plant seed is a monocot. In one embodiment, the transgenic plant seed is maize. In one embodiment, the transgenic plant seed is wheat. In another embodiment, the transgenic plant seed is rice. According to other embodiments, the transgenic plant seed is a dicot. In one embodiment, the transgenic plant seed is soybean. In an additional embodiment, the transgenic plant seed is *Arabidopsis*.

In another embodiment, the invention encompasses a method of producing a higher yielding transgenic host comprising (a) stably transforming a plant cell with a nucleic acid molecule comprising a polynucleotide sequence of the invention, wherein the nucleic acid is capable of being expressed in the plant cell, and (b) regenerating the cell into a plant. According to one embodiment, the plant cell is a monocot. In a further embodiment, the plant cell is maize. In one embodiment, plant cell is wheat. In another embodiment, the plant cell is rice. According to other embodiments, the plant cell is a dicot. In one embodiment, the plant cell is soybean. In an additional embodiment, the plant cell is *Arabidopsis*.

Methods and reagents for regenerating plants and plant tissue from transgenic cell are known in the art and vary from species to species of plants. Generally, the cell is grown to callus formation and shoot formation is induced from the callus and subsequently rooted. Alternatively, embryo formation can be induced in the callus tissue. These embryos germinate as natural embryos to form plants. The culture media generally contains sufficient components to sustain cell growth and division, and includes for example, amino acids and hormones such as, auxins and cytokinins, to sustain growth and induce cellular differentiation. It is envisioned that after the stable integration of polynucleotides of the invention into the host genomic DNA, the polynucleotides can be transferred to other plants by sexual crossing. Any of a number of standard breeding techniques can be used, depending upon the species to be crossed. Once transgenic plants of this type are produced, the plants themselves can be cultivated in accordance with conventional procedure so that the nucleic acid construct is present in the resulting plants. Alternatively, transgenic seeds or propagules (e.g., cuttings) are recovered from the transgenic plants. These seeds can then be planted in the soil and cultivated using conventional procedures to produce transgenic plants.

In some embodiments, the invention provides a method of growing a transgenic plant comprising, (a) planting a transgenic seed comprising a nucleic acid, vector and/or expression cassette of the invention and (b) growing a transgenic plant from the transgenic seed. In some embodiments, the method further comprises the step of harvesting the transgenic plant. In additional embodiments, the method further comprises the step of replanting seed from the transgenic plant. In some embodiments, the transgenic plant is a monocot. In additional embodiments, the transgenic plant is maize. In other embodiments, the transgenic plant is wheat. In some embodiments, the transgenic plant is rice. In other embodiments, the transgenic plant is a dicot. In some embodiments, the transgenic plant is soybean.

A transgenic plant formed using *Agrobacterium* transformation methods typically may contain a single simple recombinant DNA sequence inserted into one chromosome, referred to as a transgenic event. Such transgenic plants can be referred to as being heterozygous for the inserted exogenous sequence. A transgenic plant homozygous with respect to a transgene can be obtained by sexually mating ("selfing") an independent segregant transgenic plant that contains a single exogenous gene sequence to itself, for example an F0 plant, to produce F1 seed. One fourth of the F1 seed produced will be homozygous with respect to the transgene. Germinating F1 seed results in plants that can be tested for heterozygosity, typically using a SNP assay or a thermal amplification assay that allows for the distinction between heterozygotes and homozygotes (i.e., a zygosity assay). Crossing a heterozygous plant with itself or another heterozygous plant results in heterozygous progeny, as well as homozygous transgenic and homozygous null progeny.

In addition to the direct transformation of a plant with a polynucleotide of the invention, transgenic plants can be prepared by crossing a first plant having a polynucleotide of the invention with a second plant lacking the polynucleotide of the invention. For example, a polynucleotide of the invention can be stably introduced (i.e., integrated in the genomic DNA) into first plant line that is amenable to transformation to produce a transgenic plant that can be crossed with a second plant line to introgress the polynucleotide of the invention into the second plant line.

Also provided are methods of using the polynucleotides of the invention to produce a plant which has an enhanced trait, comprising the steps of introducing a polynucleotide of the invention into a host plant cell, selecting for the presence of the polynucleotide molecule to produce a transgenic plant cell, and regenerating a transgenic plant from the transgenic plant cell, whereby the transgenic plant has an enhanced trait when compared to a comparable wild-type plant or a transgenic HaHB4 plant wherein HaHB4 is under the same promoter. Enhanced traits of transgenic plants that can be selected according to the methods of the invention, include, but are not limited to, enhanced water use efficiency (e.g., "drought tolerance"), enhanced salinity tolerance, enhanced tolerance to osmotic stress, increased yield, and combinations thereof.

Plant, Seed and Plant Part Products

In additional embodiments, the invention relates to plant commodity products and methods for producing plant commodity products, produced from a plant or plant part as described herein. Commodity products containing polynucleotide or polypeptide sequences of the invention, and produced from a transgenic plant or seed containing the polynucleotide sequences of the invention are specifically contemplated as embodiments of the invention. A commodity product containing a polynucleotide or polypeptide of the invention is intended to include, but not be limited to, meals, oils, crushed or whole grains or seeds of a plant, or any food product comprising any meal, oil, or crushed or whole grain of a recombinant plant or seed containing one or more of the sequences of the present invention. Thus, according to one embodiment, the invention encompasses processed plant product containing a detectable amount of a polynucleotide or polypeptide of the invention wherein the plant product comprises a feed, a meal, a flour, extract, or homogenate obtained from at least one part of a plant. In an additional embodiment, the invention encompasses a processed plant product containing a detectable amount of a polynucleotide or polypeptide of the invention wherein the plant product comprises a feed, a meal, a flour, extract, or homogenate obtained from a seed. The detection of polynucleotides and polypeptides of the invention in processed plant products can be performed using techniques and regents known in the art, including for example PCR, and Northern, Southern, and Western analysis.

Gene Stacking

The present invention also encompasses seeds and plants having one or more transgenic events. The invention also contemplates that polynucleotides and polypeptides of the invention can be used in combination with other transgenic "events" to create plants with multiple desired traits or a further enhanced trait. These "stacked" transgenic events can be events that are directed to the same target organism or trait, or they can be directed to different target pathogens, pests, or traits. Moreover, the stacked events can be created by any method, including but not limited to, cross breeding of transgenic plants, or multiple genetic transformation.

In some embodiments, a transgenic seed or plant of the invention additionally has a stacked transgenic event that provides herbicide tolerance. Examples of herbicides for which recombinant expression provides resistance include, but are not limited to, dicamba, glufosinate-ammonium and glyphosate and N-(phosphonomethyl)glycine, including its isopropylamine salt form.

In additional embodiments, a transgenic seed or plant of the invention additionally has a stacked transgenic event that provides resistance to insects. Examples of genes for which recombinant expression provides resistance to insects include, but are not limited to, variants of the *Bacillus thuringiensis* Cry (e.g., Cry1A, Cry1Ac, Cry2A, Cry1F-1Ac, Cry3A, Cry3Bb, Cry35Ab1) and/or Cyt gene families.

In other embodiments, a transgenic seed or plant of the invention additionally has a stacked transgenic event that provides resistance to fungal disease, viral disease or bacterial disease, or infestation (e.g., nematode infestation).

In further embodiments, a transgenic seed or plant of the invention additionally has a stacked transgenic event that provides resistance to an environmental stress selected from the group consisting of: drought conditions, salinity conditions, osmotic stress, cold temperature exposure, heat exposure, reduced nitrogen nutrient availability, reduced phosphorous nutrient availability, and high plant density.

In further embodiments, a transgenic seed or plant of the invention additionally has a stacked transgenic event that provides increased nitrogen use efficiency or yield.

EXAMPLES

The invention is further described in the following Examples. It should be understood that these Examples, are provided by way of illustration only. From the above discussion and the following Examples, one can ascertain the essential characteristics of this invention, and without departing from the spirit and scope thereof, can make various changes and modifications of the invention to adapt it to various uses and conditions.

Example 1

Generation and Characterization of Modified HaHB4.2 Expression Constructs

The open reading frame of cDNA encoding full-length HaHB4 (SEQ ID NO:1) cloned into the BamH1/Sac1 sites of pBlueScript SK⁻ vector (Stratagene, Upsala, Sweden) was used as a template for a series of PCR reactions to create modified HaHB4. In a first step, a PCR reaction was performed using the H4m-F forward primer (5'-ATGTCTCTTCAACAAGTAACAACCACCAGG-3'; SEQ ID NO:22) and the Transf2 reverse primer (5'-GCCGAGCTCTTAGAACTCCCACCACTTTTG-3'; SEQ ID NO:23) to generate a first amplified PCR product. The primer design for this amplification run, amplified a product that contains a newly introduced transcription initiation site and transcription termination site. The first PCR amplification product was cloned into a pGEM®-T-Easy vector (Promega, Madison, Wis.) and named "pTHaHB4.2a."

pTHaHB4.2a was in turn used as the template in a second PCR amplification reaction using the H4m-F forward primer (5'-ATGTCTCTTCAACAAGTAACAACCACCAGG-3'; SEQ ID NO:22) and a reverse primer designated H4m-R (5-TTAGAACTCCC ACCACTTTTGAAGGTCTGG-3'; SEQ ID NO:24) to generate a second PCR amplification product that was then cloned into a pGEM®-T-Easy vector and named pTHaHB4.2b.

In a third PCR amplification reaction, pTHaHB4.2b was used as a template in a PCR reaction using two sets of primers, one set of primers corresponding to the Transf-1 forward primer (5'-GCGGGATCCACCATGTCTCTTCAACAAGTA-3'; SEQ ID NO:26) and a reverse primer designated H4m-R1 (5'-GTTTCCTTCTTCAAGGTACGCAAAACCGTCGC-3'; SEQ ID NO:27) and a second set of primers consisting of the H4m-F1 forward primer (5'-CGGTTTTGCGTACCTTGAAGAAGGAAACAGTTTG-3'; SEQ ID NO:25) and the reverse primer Transf-2 (5'-GCCGAGCTCTTAGAACTCCAACCACTTTTG-3'; SEQ ID NO:23). The amplified products of the 2 sets of primers were then fused into a contiguous chimeric polynucleotide sequence using conventional recombinant techniques. See, e.g., Silver J. Limjoco T, Feinstone S (1995) Site-specific mutagenesis using the polymerase chain reaction. In: Innis M A, Gelfand D H, Sninsky J J (eds.) PCR Strategies. Academic Press Inc, San Diego, pp 179-188. Briefly, the strategy included denaturation of both PCR products followed by mixing and hybridization steps. The hybridization products were extended with Klenow enzyme and a further PCR reaction was performed the chimeric polynucleotide sequence as the template, the Transf-1 forward primer (SEQ ID NO: 26) and the Transf-2 reverse (SEQ ID NO: 23) primers. The amplified PCR product of this reaction was then cloned into a pGEM®-T-Easy vector and named pTHaHB4.2c.

A sequence analysis of the amplified products at each step of the pTHaHB4.2c expression construct generation process revealed the following when compared with the HaHB4 polynucleotide sequence of SEQ ID NO:1: (a) the amplified PCR product encoded a polypeptide containing a four amino acid deletion in the amino terminal region (amino acid residues 7-10 of SEQ ID NO:2); (b) the second amplified PCR product contained a mutation of P175L in a region encoding the putative activation domain of HaHB4, and a deletion of four nucleotides located in the 5' UTR; (c) the product of the third PCR reaction contained an L159F mutation in a region encoding the carboxy terminal portion of HaHB4; and (d) the amplified product of the last PCR reaction described above, contained a conservative R22K mutation.

The insert in pTHaHB4.2c was then further amplified in a PCR reaction in order to introduce a conservative amino acid change K22R. The sequence corresponding to the amplified insert in pTHaHB4.2c was sequenced and determined to correspond to polynucleotide SEQ ID NO:3 and to encode the polypeptide sequence disclosed in FIG. 1A-B (SEQ ID NO:4). FIG. 1A-B presents an alignment indicating the sequence differences of HaHB4 (SEQ ID NO:2), HaHB4.2 (mod1HaHB4 (SEQ ID NO:4)) and an additional modified HaHB4 transcription factor (mod2HaHB4 (SEQ ID NO:8)).

HaHB4.2 Expression Constructs

The pTHaHB4.2c (HaHB4.2) polynucleotide sequences generated above were cloned in operable linkage into maize, soybean and wheat vectors to generate the soybean (FIGS. 2A-2C), wheat (FIGS. 2D-2G) and maize (FIGS. 2H-2J) expression constructs schematically depicted in FIGS. 2A-2J. Each of the expression constructs described in FIGS. 2A-23, contain a HaHB4.2 sequence that encodes an 177 amino acid, full length mod1HaHB4 (i.e., HaHB4.2 (SEQ ID NO:4)) protein and is operably linked with either (a) a constitutive promoter, such as the 35S CaMV promoter (pZmHaHB4.2, pGmHaHB4.2) or Ubi promoter (pTaHaHB4.2), or (b) an inducible promoter composed of a modified version of the HaHB4 promoter fused with the first intron of the *Arabidopsis* Cox5c-2 gene (LPF-Cox) (pZmPrInHBH4.2, pGmPrInHB4.2, and pTaPrInHB4.2). Each of the expression constructs depicted in FIGS. 2A-2J, also contain a selection marker and a nos terminator downstream of HaHB4.2 cDNA.

Example 2

Production of Modified HaHB4 Transgenic Plants

Generation and Selection of Soybean mod1HaHB4 Transgenic Events mod1HaHB4 soybean transgenic events were generated using an *Agrobacterium*-mediated protocol and the cultivar Williams 82. $T_1$ seeds were obtained for 35 independent events using three different expression cassettes reflecting one constitutive and two inducible strategies. The expression of the mod1HaHB4 cDNA coding sequence in the constitutive events was driven by the 35S CaMV promoter. Expression of the mod1HaHB4 cDNA coding sequence in the inducible events was directed by either the native HaHB4 promoter long allele or a chimeric polynucleotide sequence containing the same HaHB4 promoter long allele and the AtCOX5c2 intron.

The first multiplication of the transformed cells was conducted in a greenhouse during which time 10 $T_1$ individuals derived from each event were sampled for a segregation test by PCR determination. Lines derived from selfings of individuals from selected events (3:1 segregation in $T_1$) were sowed and plants were sampled using PCR analysis to identify homozygous lines, as indicate by the absence of negative segregants among sampled progeny (at least 5 individuals sampled per line). Some negative segregants identified during the screening process were maintained as control "null lines."

Seed augmentation ($T_3$ seed) of single-copy homozygous and null lines was conducted in a greenhouse during which seeds of selected mod1HaHB4 homozygous lines were used to confirm ethylene insensitivity and to quantify HaHB4 and downstream gene (LOX2 and CSD-1) expression levels in the selected lines. The selected mod1HaHB4 homozygous lines were also evaluated for drought stress tolerance under lab conditions. Twenty-two single-copy mod1HaHB4 homozygous cell lines were identified for further study.

Field Trials of mod1HaHB4 Transgenic Soybean

Soybean transgenic (mod1HaHB4 (SEQ ID NO:4)) and control lines were evaluated under field conditions at Liborio Luna (33°35'15"S, 65°38'09"W), San Luis, Argentina. Soil was a sandy loam with a pH of 5.99 and organic matter content of 1.41%. Annual mean rainfall is 800 mm.

Fifteen transgenic lines, seven negative segregants (null) lines and the wild type (Williams 82) were planted at a rate of 28 plants $m^{-2}$. The experimental design was a complete randomized block, split plot with 3 replications with the irrigation as the main plot and the soybean lines as the subplots. Two levels (low and high) of irrigation regime were applied. For the low irrigation regime the water supply was suspended from plant reproductive stages R1 to R6. Therefore, this regime consisted of only two water applications, one at the beginning of the season and the other one at the end of the season. As indicated in Table 1, the high irrigation regime consisted of monthly water applications.

Plots were 5 m long with 4 rows spaced at 0.7 m. Pesticides and fertilizers were applied according to local practices. Yield data was obtained from the two central rows in each plot. Plants were hand-clipped and threshed with stationary equipment. Seed weight and moisture were recorded. Yield for each replication is presented in Table 2.

TABLE 1

Irrigation Regime and Rainfall During Growing Season of Field Trial

| Month | Precipitation | High Irrigation | Low Irrigation |
|---|---|---|---|
| January | 80.52 mm | 115.0 mm | 115.0 mm |
| February | 65.02 mm | 112.0 mm | NA |
| March | 51.05 mm | 130.0 mm | NA |
| April | 6.1 mm | 20.0 mm | 20.0 |
| TOTAL | 202.69 mm | 377.0 mm | 135.0 mm |

Yield data was analyzed as split plot, using GLM procedure (SAS software) which allows analyses of variance for data sets with missing values. Significant differences were detected at an alpha level of 0.05. Treatment (high and low irrigation) was the main plot and soybean lines were the subplots. The yield data is presented in Table 2.

There were significant treatment (p=0.0079) and line (p<0.0001) main effects. The low irrigation regime caused a yield reduction of 35% compared to the high irrigation regime (from 2900 Kg $ha^{-1}$ to 1897 Kg $ha^{-1}$). Given that not all homozygous lines had their null counterparts, comparisons between homozygous and null lines were carried out within or between constructions. Homozygous mod1HaHB4 transgenic lines within or between constructions and within the same line had higher yield than the null lines, except the line a3H. This homozygous line had lower yield than six null lines (a7N, a9N, b1N, b8N, b10N, c4N). There were no significant yield differences between transgenic and null lines for inducible transgenic events within the same line. However, constitutive mod1HaHB4 transgenic events a7H and a9H had higher yield than their null counterparts respectively, in both the high and low irrigation regimes. Null events a9N, a7N and a homozygous (a3H) line had a significant yield reduction when compared to Williams 82.

TABLE 2

Yield (kg · $ha^{-1}$) data for the low and high irrigated growing conditions for the constitutive mod1HaHB4 transgenic soybean lines tested. (NA = not available).

| Line | Irrigated Treatment | Yield Block 1 | Block 2 | Block 3 | Mean | SE |
|---|---|---|---|---|---|---|
| a3H | Low | 1063.11 | 1221.52 | NA | 1142.32 | 79.20 |
|  | High | 1672.54 | 1777.71 | NA | 1725.13 | 52.59 |
| a5H | Low | 1931.31 | 2021.73 | 2271.80 | 2074.95 | 101.83 |
|  | High | 2704.24 | 3355.42 | 3562.40 | 3207.35 | 258.55 |
| a7H | Low | 2253.47 | 1568.59 | 2192.43 | 2004.83 | 218.83 |
|  | High | 3004.71 | 3285.00 | 3001.79 | 3097.17 | 93.92 |
| a8H | Low | 1975.54 | 1901.83 | 2106.19 | 1994.52 | 59.75 |
|  | High | 3073.30 | 3315.00 | 3070.29 | 3152.86 | 81.07 |
| a9H | Low | 2170.36 | 1997.26 | 1872.34 | 2013.32 | 86.40 |
|  | High | 2979.64 | 3056.01 | 2809.58 | 2948.41 | 72.83 |
| a10H | Low | 2088.81 | 1935.13 | 1905.47 | 1976.47 | 56.82 |
|  | High | 2260.03 | 2827.00 | 3333.66 | 2806.90 | 310.09 |
| a7N | Low | 1874.16 | 1885.18 | 1802.11 | 1853.82 | 26.05 |
|  | High | 1957.21 | 2292.51 | 2690.64 | 2313.46 | 211.98 |
| a9N | Low | 1607.35 | 1694.60 | 1656.00 | 1652.65 | 25.24 |
|  | High | 2214.50 | 2756.25 | 3072.30 | 2681.02 | 250.47 |

FIGS. 3A-3D provide bar graphs indicating yield improvement in transgenic crops under irrigated field conditions (without water limitations under non-water stressed conditions) in a high productivity environment. FIGS. 3A-3B present bar graphs depicting yield improvement of two homozygous transgenic maize lines (expressing HaHB4.2 (SEQ ID NO:4) under the control of an 35S constitutive promoter) as compared to the yield of wild type control maize (WT). Data were collected from replicated field plots in two locations with different soil types: in a silty loam soil with 626 mm of rain received throughout the growing period (FIG. 3A), and in a well-drained silty loam soil with 545 mm of rain received during the crop cycle (FIG. 3B). FIG. 3C presents a bar graph depicting yield improvement of a homozygous transgenic wheat line (expressing HaHB4.2 (SEQ ID NO:4) under the control of an 35S constitutive promoter) as compared to the yield of wild type control wheat (WT). Data in FIG. 3C were obtained from replicated field plots in a location with well drained sandy loam soil (pH 7.14%, OM 1.57%). Supplemental irrigation was applied to provide for 755 mm of water throughout the crop cycle. FIG. 3D presents a bar graph depicting yield improvement of two homozygous transgenic soybean lines (expressing HaHB4.2 (SEQ ID NO:4) under the control of an 35S constitutive promoter) as compared to the yield of wild type control soybean (WT). Data in FIG. 3D were obtained from replicated field plots in location with sandy loam soil (pH 5.99%, OM 1.41%). Supplemental irrigation was applied to provide for 579 mm of water throughout the crop cycle.

Procedure for Characterizing Transgenes from Maize and Soybean Lines

Northern analysis was initially conducted using methods and materials known in the art to confirm HaHB4 expression in the transgenic maize and soybean lines. The coding sequences of transgenes corresponding to homozygous HaHB4 transformed plant lines were then amplified using conventional PCR methods and materials as generally described herein. Maize and soybean transgenic genomic DNA was prepared using methods known in the art and was used as the template in the PCR reactions. Transgenes corresponding to constitutive (35S CaMV promoter) expression cassettes were amplified in PCR reactions using the 35S PrimF forward primer (5'-TGACGCACAATCCCACTATC-3' (SEQ ID NO:34) and the NOS121R reverse primer (5-GAATTCCCGATCTAGTAACATA-3' (SEQ ID NO:35). Transgenes corresponding to inducible (TRANSF1Xba promoter) expression cassettes were amplified in PCR reactions using the TRANSF1Xba forward primer (5'-ATGTCTCT-TCAACAAGTACCCAC-3' (SEQ ID NO:32)), the NOS121R reverse primer (5'-GAATTCCCGATCTAGTAA-CATA-3' (SEQ ID NO:33), and maize or soybean transgenic genomic DNA as the template.

Sequence analysis of the amplified HaHB4 polynucleotides identified multiple variations between the amplified sequence and the sequence of native HaHB4 (SEQ ID NO:1). FIG. 1 provides an alignment between native HaHB4 and the sequence encoded by the mod1HaHB4 (HaHB4.2 (SEQ ID NO:4)) and mod2HaHB4 (HaHB4.3 ((SEQ ID NO:8)) identified by this analysis.

Example 3

Transactivation by Modified HaHB4 in Yeast

Polynucleotides encoding modified HaHB4 proteins (HaHB4.2 (mod1HaHB4)HaHB4.3 (mod2HaHB4), or HaHB4.4 (mod3HaHB4)) were cloned in the pGBKT7 vector in operative association with the GAL4 DNA binding domain in the vector and the yeast transformed with the resulting expression constructs were assayed in a yeast simple hybrid assay to determine transactivation by the encoded modified HaHB4. Transactivation by modified HaHB4 (and control HaHB4 protein) was determined by measuring β-galactosidase activity for the yeast containing modified HaHB4 proteins (and control HaHB4 protein) by using ONPG as substrate. FIG. 4 provides a bar graph showing that all modified HaHB4 proteins act as an activator in the yeast simple hybrid assay system.

Similarly, in order to determine the ability of the modified HaHB4 protein to heterodimerize, yeast two hybrid assays were performed. HaHB4.2 cDNA was cloned into the pGAD vector and fused to the activation domain of the yeast transcription factor GAL4. The resulting expression construct was then transformed into S. cerevisiae strain AH109, and a two hybrid assay was performed using the yeast expressing the modified protein and four Arabidopsis HD-Zip proteins with deleted carboxy termini that were previously cloned in the pGBK7 vector and fused with the GAL4 binding domain therein. The putative interactions were evaluated by auxotrophy in a (−HIS) SD medium. The results indicated that HaHB4.2 acted as a transcription factor and was able to interact with AtHB1, AtHB7 and AtHB12. (Data not shown)

These results indicate that the interaction with endogenous proteins may constitute a partial mechanism of mod1HaHB4 (HaHB4.2) to exert its function.

Example 4

Morphology and Photosynthesis Rate of Transgenic Arabidopsis Plants

Arabidopsis plants were transformed with 35S::H4.2 (an expression construct comprising mod1HaHB4 (SEQ ID NO:4) operably associated with an 35S constitutive promoter) by floral dip technique to generate transgenic Arabidopsis plants. Leaf $CO_2$ gas exchange measurements were made on three plants per pot. One detached leaf of each sampled plant was placed into the leaf cuvette of a Licor 6400 XT photosynthesis system. Leaves were illuminated by the Licor 6400 LED light source providing a photosynthetic photon flux density around 1000 μmol m-2 s-1

Photosynthesis rate (μmol m-2 s-1) was measured when foliar $CO_2$ uptake was steady, while the air flowing into the leaf cuvette was regulated by the Licor 6400 system to maintain a temperature around 24° C. and a CO2 concentration around 500 μmol mol-1. FIG. 5 provides a bar graph showing photosynthesis rate in transgenic plants expressing empty vector (pBH21) and transgenic plants expressing mod1HaHB4 (HaHB4.2 Line 30) in two independent experiments. It was observed that transgenic plants expressing mod1HaHB4 had a significantly higher photosynthesis rate than the control plants expressing empty vector. This increase may be responsible for the increased yield observed in crops transformed with modified mod1HaHB4.

This application claims the benefit of U.S. Provisional Appl. No. 61/601,335, filed Feb. 21, 2012, which is incorporated by reference in its entirety. In addition, all the publications referenced to herein are incorporated by reference in their entirety.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

What is claimed is:

1. An isolated nucleic acid molecule comprising a polynucleotide sequence encoding SEQ ID NO: 4.

2. The nucleic acid molecule of claim 1, which is operably linked to a promoter.

3. The nucleic acid molecule of claim 2, which is operably linked to a constitutive promoter.

4. The nucleic acid molecule of claim 3, wherein the promoter is the 35S CaMV promoter or the Ub1 promoter.

5. The nucleic acid molecule of claim 2, which is operably linked to an inducible promoter.

6. The nucleic acid molecule of claim 5, wherein the promoter comprises at least 200 nucleotides of SEQ ID NO:20 or SEQ ID NO:21.

7. The nucleic acid molecule of claim 6, wherein the promoter is fused with the first intron of the *Arabidopsis* Cox5c2.

8. A vector comprising the nucleic acid molecule of claim 1.

9. The vector of claim 8 further comprising a promoter operably linked to the nucleic acid molecule.

10. A host cell comprising the nucleic acid molecule of claim 1.

11. The host cell of claim 10, wherein the host cell is a bacterial, fungal, insect, plant or animal cell.

12. The host cell of claim 11, wherein the host cell is a plant cell.

13. The plant cell of claim 12, which is from a monocot or a dicot.

14. The plant cell of claim 13, which is selected from the group consisting of a maize cell, a wheat cell, a rice cell, and a soybean cell.

15. The host plant cell of claim 12 wherein the nucleic acid molecule is operably linked to a promoter.

16. The host plant cell of claim 15, which expresses SEQ ID NO:4.

17. A transgenic plant seed, a transgenic pollen or a transgenic plant part comprising the nucleic acid molecule of claim 1.

18. The transgenic plant seed, transgenic pollen or transgenic plant part of claim 17, which is from a monocot or a dicot.

19. The transgenic plant seed, transgenic pollen grain or transgenic plant part of claim 18, which is selected from the group consisting of maize, wheat, rice, and soybean.

20. The transgenic plant seed, pollen or plant part of claim 17, wherein the nucleic acid molecule is integrated into the transgenic plant cell's DNA.

21. The transgenic plant seed, pollen or plant part of claim 17 wherein the nucleic acid molecule is operably linked to a promoter.

22. The transgenic plant seed, transgenic pollen or transgenic plant part of claim 17 which expresses SEQ ID NO:4.

23. The transgenic plant seed, transgenic pollen or transgenic plant part of claim 17 which has gene stacking.

24. A seed or pollen grain of the transgenic plant of claim 17 comprising the nucleic acid molecule of claim 1.

25. A transgenic plant grown from the seed of claim 17 comprising the nucleic acid molecule of claim 1.

26. A progeny plant of any generation of the transgenic plant of claim 17, wherein said progeny plant comprises a nucleic acid molecule encoding SEQ ID NO: 4.

27. A protein encoded by the nucleic acid molecule of claim 1, wherein said protein comprises SEQ ID NO:4.

28. A processed plant product comprising a detectable amount of the nucleic acid molecule of claim 1.

29. A method of producing a higher yielding transgenic host comprising (a) stably transforming a plant cell with a nucleic acid molecule comprising a nucleic acid molecule encoding SEQ ID NO: 4, wherein the nucleic acid is capable of being expressed in the plant cell, and (b) regenerating the cell into a plant.

30. A method of growing a transgenic plant comprising
   (a) planting a transgenic seed comprising the nucleic acid molecule of claim 1; and
   (b) growing a transgenic plant from the transgenic seed.

* * * * *

SEQUENCE LISTING

<160> NUMBER OF SEQ ID NOS: 39

<210> SEQ ID NO 1

<211> LENGTH: 673
<212> TYPE: DNA
<213> ORGANISM: Helianthus annuus
<220> FEATURE:
<221> NAME/KEY: misc_feature
<222> LOCATION: (1)..(673)
<223> OTHER INFORMATION: Hahb-4

<400> SEQUENCE: 1

```
tcactagtac cataatattc acaaacacac acacctcaga aacgaagctt gcacataatg      60
tctcttcaac aagtacccac aacagaaaca accaccagga agaaccgaaa cgaggggcgg     120
aaacgattta ccgacaaaca aataagtttc ctagagtaca tgtttgagac acagtcgaga     180
cccgagttaa ggatgaaaca ccagttggca cataaactcg ggcttcatcc tcgtcaagtg     240
gcgatatggt tccagaacaa acgcgcgcga tcaaagtcga ggcagattga gcaagagtat     300
aacgcgctaa agcataacta cgagacgctt gcgtctaaat ccgagtctct aaagaaagag     360
aatcaggccc tactcaatca gttggaggtg ctgagaaatg tagcagaaaa gcatcaagag     420
aaaactagta gtagtggcag cggtgaagaa tcggatgatc ggtttacgaa ctctccggac     480
gttatgtttg gtcaagaaat gaatgttccg ttttgcgacg gttttgcgta ctttgaagaa     540
ggaaacagtt tgttggagat tgaagaacaa ctgccagacc ctcaaaagtg gtgggagttc     600
taaagagtaa agaaggatgt agaagtagta gagtaaaaac taaaacatac cagatagttg     660
gtttacactt tgt                                                        673
```

<210> SEQ ID NO 2
<211> LENGTH: 181
<212> TYPE: PRT
<213> ORGANISM: Helianthus annuus
<220> FEATURE:
<221> NAME/KEY: MISC_FEATURE
<222> LOCATION: (1)..(181)
<223> OTHER INFORMATION: Hahb-4

<400> SEQUENCE: 2

```
Met Ser Leu Gln Gln Val Pro Thr Thr Glu Thr Thr Thr Arg Lys Asn
1               5                   10                  15

Arg Asn Glu Gly Arg Lys Arg Phe Thr Asp Lys Gln Ile Ser Phe Leu
            20                  25                  30

Glu Tyr Met Phe Glu Thr Gln Ser Arg Pro Glu Leu Arg Met Lys His
        35                  40                  45

Gln Leu Ala His Lys Leu Gly Leu His Pro Arg Gln Val Ala Ile Trp
    50                  55                  60

Phe Gln Asn Lys Arg Ala Arg Ser Lys Ser Arg Gln Ile Glu Gln Glu
65                  70                  75                  80

Tyr Asn Ala Leu Lys His Asn Tyr Glu Thr Leu Ala Ser Lys Ser Glu
                85                  90                  95

Ser Leu Lys Lys Glu Asn Gln Ala Leu Leu Asn Gln Leu Glu Val Leu
            100                 105                 110

Arg Asn Val Ala Glu Lys His Gln Glu Lys Thr Ser Ser Ser Gly Ser
        115                 120                 125

Gly Glu Glu Ser Asp Asp Arg Phe Thr Asn Ser Pro Asp Val Met Phe
    130                 135                 140

Gly Gln Glu Met Asn Val Pro Phe Cys Asp Gly Phe Ala Tyr Phe Glu
145                 150                 155                 160

Glu Gly Asn Ser Leu Leu Glu Ile Glu Glu Gln Leu Pro Asp Pro Gln
                165                 170                 175
```

```
Lys Trp Trp Glu Phe
            180

<210> SEQ ID NO 3
<211> LENGTH: 167
<212> TYPE: DNA
<213> ORGANISM: Helianthus annuus
<220> FEATURE:
<221> NAME/KEY: misc_feature
<222> LOCATION: (1)..(167)
<223> OTHER INFORMATION: Hahb-4

<400> SEQUENCE: 3
atgtctcttc aacaagtaac aaccaccagg aagaaccgaa atgaggggcg gagacgattt      60
accgacaaac aaataagttt cctagagtac atgtttgaga cacagtcgag acccgagtta    120
aggatgaaac accagttggc acataaactc gggcttcatc ctcgtca                  167

<210> SEQ ID NO 4
<211> LENGTH: 177
<212> TYPE: PRT
<213> ORGANISM: Helianthus annuus
<220> FEATURE:
<221> NAME/KEY: MISC_FEATURE
<222> LOCATION: (1)..(177)
<223> OTHER INFORMATION: modified Hahb-4

<400> SEQUENCE: 4

Met Ser Leu Gln Gln Val Thr Thr Thr Arg Lys Asn Arg Asn Glu Gly
1               5                   10                  15

Arg Arg Arg Phe Thr Asp Lys Gln Ile Ser Phe Leu Glu Tyr Met Phe
            20                  25                  30

Glu Thr Gln Ser Arg Pro Glu Leu Arg Met Lys His Gln Leu Ala His
        35                  40                  45

Lys Leu Gly Leu His Pro Arg Gln Val Ala Ile Trp Phe Gln Asn Lys
    50                  55                  60

Arg Ala Arg Ser Lys Ser Arg Gln Ile Glu Gln Glu Tyr Asn Ala Leu
65                  70                  75                  80

Lys His Asn Tyr Glu Thr Leu Ala Ser Lys Ser Glu Ser Leu Lys Lys
                85                  90                  95

Glu Asn Gln Ala Leu Leu Asn Gln Leu Glu Val Leu Arg Asn Val Ala
            100                 105                 110

Glu Lys His Gln Glu Lys Thr Ser Ser Gly Ser Gly Glu Ser
        115                 120                 125

Asp Asp Arg Phe Thr Asn Ser Pro Asp Val Met Phe Gly Gln Glu Met
    130                 135                 140

Asn Val Pro Phe Cys Asp Gly Phe Ala Tyr Leu Glu Glu Gly Asn Ser
145                 150                 155                 160

Leu Leu Glu Ile Glu Glu Gln Leu Pro Asp Leu Gln Lys Trp Trp Glu
                165                 170                 175

Phe

<210> SEQ ID NO 5
<211> LENGTH: 99
<212> TYPE: PRT
<213> ORGANISM: Helianthus annuus
<220> FEATURE:
<221> NAME/KEY: MISC_FEATURE
<222> LOCATION: (1)..(99)
<223> OTHER INFORMATION: modified Hahb-4 homeodomain-leucine zipper

<400> SEQUENCE: 5
```

```
Arg Asn Glu Gly Arg Arg Arg Phe Thr Asp Lys Gln Ile Ser Phe Leu
1               5                   10                  15

Glu Tyr Met Phe Glu Thr Gln Ser Arg Pro Glu Leu Arg Met Lys His
            20                  25                  30

Gln Leu Ala His Lys Leu Gly Leu His Pro Arg Gln Val Ala Ile Trp
        35                  40                  45

Phe Gln Asn Lys Arg Ala Arg Ser Lys Ser Arg Gln Ile Glu Gln Glu
    50                  55                  60

Tyr Asn Ala Leu Lys His Asn Tyr Glu Thr Leu Ala Ser Lys Ser Glu
65                  70                  75                  80

Ser Leu Lys Lys Glu Asn Gln Ala Leu Leu Asn Gln Leu Glu Val Leu
                85                  90                  95

Arg Asn Val

<210> SEQ ID NO 6
<211> LENGTH: 12
<212> TYPE: PRT
<213> ORGANISM: Helianthus annuus
<220> FEATURE:
<221> NAME/KEY: MISC_FEATURE
<222> LOCATION: (1)..(12)
<223> OTHER INFORMATION: modified Hahb-4

<400> SEQUENCE: 6

Met Ser Leu Gln Gln Val Thr Thr Thr Arg Lys Asn
1               5                   10

<210> SEQ ID NO 7
<211> LENGTH: 17
<212> TYPE: PRT
<213> ORGANISM: Helianthus annuus
<220> FEATURE:
<221> NAME/KEY: MISC_FEATURE
<222> LOCATION: (1)..(17)
<223> OTHER INFORMATION: modified Hahb-4

<400> SEQUENCE: 7

Leu Glu Glu Gly Asn Ser Leu Leu Glu Ile Glu Glu Gln Leu Pro Asp
1               5                   10                  15

Leu

<210> SEQ ID NO 8
<211> LENGTH: 176
<212> TYPE: PRT
<213> ORGANISM: Helianthus annuus
<220> FEATURE:
<221> NAME/KEY: MISC_FEATURE
<222> LOCATION: (1)..(176)
<223> OTHER INFORMATION: modified Hahb-4

<400> SEQUENCE: 8

Met Ser Leu Gln Gln Val Pro Thr Arg Lys Asn Arg Asn Glu Gly Arg
1               5                   10                  15

Arg Arg Phe Thr Asp Lys Gln Ile Ser Phe Leu Glu Tyr Met Phe Glu
            20                  25                  30

Thr Gln Ser Arg Pro Glu Leu Arg Met Lys His Gln Leu Ala His Lys
        35                  40                  45

Leu Gly Leu His Pro Arg Gln Val Ala Ile Trp Phe Gln Asn Lys Arg
    50                  55                  60

Ala Arg Ser Lys Ser Arg Gln Ile Glu Gln Glu Tyr Asn Ala Leu Lys
65                  70                  75                  80
```

```
His Asn Tyr Glu Thr Leu Ala Ser Lys Ser Glu Ser Leu Lys Lys Glu
                85                  90                  95

Asn Gln Ala Leu Leu Asn Gln Leu Glu Val Leu Arg Asn Val Ala Glu
            100                 105                 110

Lys His Gln Glu Lys Thr Ser Ser Gly Ser Gly Glu Ser Asp
        115                 120                 125

Asp Arg Phe Thr Asn Ser Pro Asp Val Met Phe Gly Gln Glu Met Asn
    130                 135                 140

Val Pro Phe Cys Asp Gly Phe Ala Tyr Leu Glu Gly Asn Ser Leu
145                 150                 155                 160

Leu Glu Ile Glu Glu Gln Leu Pro Asp Leu Gln Lys Trp Trp Glu Phe
                165                 170                 175
```

<210> SEQ ID NO 9
<211> LENGTH: 11
<212> TYPE: PRT
<213> ORGANISM: Helianthus annuus
<220> FEATURE:
<221> NAME/KEY: MISC_FEATURE
<222> LOCATION: (1)..(11)
<223> OTHER INFORMATION: modified Hahb-4

<400> SEQUENCE: 9

```
Met Ser Leu Gln Gln Val Pro Thr Arg Lys Asn
1               5                   10
```

<210> SEQ ID NO 10
<211> LENGTH: 99
<212> TYPE: PRT
<213> ORGANISM: Helianthus annuus
<220> FEATURE:
<221> NAME/KEY: MISC_FEATURE
<222> LOCATION: (1)..(99)
<223> OTHER INFORMATION: Hahb-4 homeodomain-leucine zipper

<400> SEQUENCE: 10

```
Arg Asn Glu Gly Arg Lys Arg Phe Thr Asp Lys Gln Ile Ser Phe Leu
1               5                   10                  15

Glu Tyr Met Phe Glu Thr Gln Ser Arg Pro Gly Leu Arg Met Lys His
            20                  25                  30

Gln Leu Ala His Lys Leu Gly Leu His Pro Arg Gln Val Ala Ile Trp
        35                  40                  45

Phe Gln Asn Lys Arg Ala Arg Ser Lys Ser Arg Gln Ile Glu Gln Glu
    50                  55                  60

Tyr Asn Ala Leu Lys His Asn Tyr Glu Thr Leu Ala Ser Lys Ser Glu
65                  70                  75                  80

Ser Leu Lys Lys Glu Asn Gln Ala Leu Leu Asn Gln Leu Glu Val Leu
                85                  90                  95

Arg Asn Val
```

<210> SEQ ID NO 11
<211> LENGTH: 9
<212> TYPE: DNA
<213> ORGANISM: Helianthus annuus
<220> FEATURE:
<221> NAME/KEY: misc_feature
<222> LOCATION: (5)..(5)
<223> OTHER INFORMATION: n is A or T

<400> SEQUENCE: 11 caatnattg                                                         9

-continued

<210> SEQ ID NO 12
<211> LENGTH: 531
<212> TYPE: DNA
<213> ORGANISM: Helianthus annuus
<220> FEATURE:
<221> NAME/KEY: misc_feature
<222> LOCATION: (1)..(167)
<223> OTHER INFORMATION: Hahb-4

<400> SEQUENCE: 12

```
atgtctcttc aacaagtaac aaccaccagg aagaaccgaa atgaggggcg gagacgattt      60
accgacaaac aaataagttt cctagagtac atgtttgaga cacagtcgag acccgagtta     120
aggatgaaac accagttggc acataaactc gggcttcatc ctcgtcaagt ggcgatatgg     180
ttccagaaca aacgcgcgcg atcaaagtcg aggcagattg agcaagagta taacgcgcta     240
aagcataact acgagacgct tgcgtctaaa tccgagtctc taaagaaaga gaatcaggcc     300
ctactcaatc aattggaggt gctgagaaat gtagccgaaa agcatcaaga gaaaactagt     360
agtagtggca gcggtgaaga atcggatgat cggtttacga actctccgga cgttatgttt     420
ggtcaagaaa tgaatgttcc gttttgcgac ggttttgcgt accttgaaga aggaaacagt     480
ttgttggaga ttgaagaaca actgccagac cttcaaaagt ggtgggagtt c              531
```

<210> SEQ ID NO 13
<211> LENGTH: 531
<212> TYPE: DNA
<213> ORGANISM: Helianthus annuus
<220> FEATURE:
<221> NAME/KEY: misc_feature
<222> LOCATION: (1)..(167)
<223> OTHER INFORMATION: Hahb-4

<400> SEQUENCE: 13

```
atgtctcttc aacaagtaac aaccaccagg aagaaccgaa atgaggggcg gagacgattt      60
accgacaaac aaataagttt cctagagtac atgtttgaga cacagtcgag acccgagtta     120
aggatgaaac accagttggc acataaactc gggcttcatc ctcgtcaagt ggcgatatgg     180
ttccagaaca aacgcgcgcg atcaaagtcg aggcagattg agcaagagta taacgcgcta     240
aagcataact acgagacgct tgcgtctaaa tccgagtctc taaagaaaga gaatcaggcc     300
ctactcaatc aattggaggt gctgagaaat gtagccgaaa agcatcaaga gaaaactagt     360
agtagtggca gcggtgaaga atcggatgat cggtttacga actctccgga cgttatgttt     420
ggtcaagaaa tgaatgttcc gttttgcgac ggttttgcgt accttgaaga aggaaacagt     480
ttgttggaga ttgaagaaca actgccagac cttcaaaagt ggtgggagtt c              531
```

<210> SEQ ID NO 14
<211> LENGTH: 537
<212> TYPE: DNA
<213> ORGANISM: Helianthus annuus
<220> FEATURE:
<221> NAME/KEY: misc_feature
<222> LOCATION: (1)..(176)
<223> OTHER INFORMATION: Hahb-4

<400> SEQUENCE: 14

```
tctagaacca tgtctcttca acaagtaccc accaggaaga accgaaatga ggggcggaga      60
cgatttaccg acaaacaaat aagtttccta gagtacatgt ttgagacaca gtcgagaccc     120
gagttaagga tgaaacacca gttggcacat aaactcgggc ttcatcctcg tcaagtggcg     180
```

```
atatggttcc agaacaaacg cgcgcgatca aagtcgaggc agattgagca agagtataac    240
gcgctaaagc ataactacga gacgcttgcg tctaaatccg agtctctaaa gaaagagaat    300
caggccctac tcaatcaatt ggaggtgctg agaaatgtag ccgaaaagca tcaagagaaa    360
actagtagta gtggcagcgg tgaagaatcg gatgatcggt ttacgaactc tccggacgtt    420
atgtttggtc aagaaatgaa tgttccgttt tgcgacggtt ttgcgtacct tgaagaagga    480
aacagtttgt ggagattga agaacaactg ccagaccttc aaaagtggtg gagttc        537
```

```
<210> SEQ ID NO 15
<211> LENGTH: 182
<212> TYPE: DNA
<213> ORGANISM: Helianthus annuus
<220> FEATURE:
<221> NAME/KEY: misc_feature
<222> LOCATION: (1)..(182)
<223> OTHER INFORMATION: Hahb-4

<400> SEQUENCE: 15
tctagaggat ccaccatgtc tcttcaacaa gtaacaacca ccaggaagaa ccgaaatgag    60
gggcggagac gatttaccga caaacaaaca gtttcctag agtacatgtt tgagacacag    120
tcgagacccg agttaaggat gaaacaccag ttggcacata aactcgggct tcatcctcgt    180
ca                                                                  182
```

```
<210> SEQ ID NO 16
<211> LENGTH: 182
<212> TYPE: DNA
<213> ORGANISM: Helianthus annuus
<220> FEATURE:
<221> NAME/KEY: misc_feature
<222> LOCATION: (1)..(182)
<223> OTHER INFORMATION: Hahb-4

<400> SEQUENCE: 16
tctagaggat ccaccatgtc tcttcaacaa gtaacaacca ccaggaagaa ccgaaatgag    60
gggcggagac gatttaccga caaacaaata gtttcctag agtacatgtt tgagacacag    120
tcgagacccg agttaaggat gaaacaccag ttggcacata aactcgggct tcatcctcgt    180
ca                                                                  182
```

```
<210> SEQ ID NO 17
<211> LENGTH: 528
<212> TYPE: DNA
<213> ORGANISM: Helianthus annuus
<220> FEATURE:
<221> NAME/KEY: misc_feature
<222> LOCATION: (1)..(164)
<223> OTHER INFORMATION: Hahb-4

<400> SEQUENCE: 17
atgtctcttc aacaagtacc caccaggaag aaccgaaatg aggggcggag acgatttacc    60
gacaaacaaa taagttttcct agagtacatg tttgagacac agtcgagacc cgagttaagg    120
atgaaacacc agttggcaca taaactcggg cttcatcctc gtcaagtggc gatatggttc    180
cagaacaaac gcgcgcgatc aaagtcgagg cagattgagc aagagtataa cgcgctaaag    240
cataactacg agacgcttgc gtctaaatcc gagtctctaa agaaagagaa tcaggcccta    300
ctcaatcaat tggaggtgct gagaaatgta gccgaaaagc atcaagagaa aactagtagt    360
agtggcagcg gtgaagaatc ggatgatcgg tttacgaact ctccggacgt tatgtttggt    420
caagaaatga atgttccgtt tttgcgacggt tttgcgtacc ttgaagaagg aaacagtttg    480
```

```
ttggagattg aagaacaact gccagacctt caaaagtggt gggagttc          528
```

<210> SEQ ID NO 18
<211> LENGTH: 774
<212> TYPE: DNA
<213> ORGANISM: Helianthus annuus
<220> FEATURE:
<221> NAME/KEY: misc_feature
<222> LOCATION: (1)..(774)
<223> OTHER INFORMATION: Hahb-4 genomic sequence

<400> SEQUENCE: 18

```
tcactagtac cataatattc acaaacacac acacctcaga aacgaagctt gcacataatg    60
tctcttcaac aagtacccac aacagaaaca accaccagga agaaccgaaa cgaggggcgg   120
aaacgattta ccgacaaaca aataagtttc ctagagtaca tgtttgagac acagtcgaga   180
cccgagttaa ggatgaaaca ccagttggca cataaactcg ggcttcatcc tcgtcaagtg   240
gcgatatggt tccagaacaa acgcgcgcga tcaaagtcga ggcagattga gcaagagtat   300
aacgcgctaa agcataacta cgagacgctt gcgtctaaat ccgagtctct aaagaaagag   360
aatcaggccc tactcaatca ggtatggttg caaacttaca atgttgcatt caactattta   420
agtagttttg aattttttgtg acaataaaga ttgacaaatg ttgtttgata attgattaac   480
agttggaggt gctgagaaat gtagcagaaa agcatcaaga gaaaactagt agtagtggca   540
gcggtgaaga atcggatgat cggtttacga actctccgga cgttatgttt ggtcaagaaa   600
tgaatgttcc gttttgcgac ggttttgcgt actttgaaga aggaaacagt ttgttggaga   660
ttgaagaaca actgccagac cctcaaaagt ggtgggagtt ctaaagagta aagaaggatg   720
tagaagtagt agagtaaaaa ctaaaacata ccagatagtt ggtttacact ttgt         774
```

<210> SEQ ID NO 19
<211> LENGTH: 101
<212> TYPE: DNA
<213> ORGANISM: Helianthus annuus
<220> FEATURE:
<221> NAME/KEY: misc_feature
<222> LOCATION: (1)..(101)
<223> OTHER INFORMATION: Hahb-4 genomic DNA intron sequence

<400> SEQUENCE: 19

```
gtatggttgc aaacttacaa tgttgcattc aactatttaa gtagttttga attttttgtga   60
caataaagat tgacaaatgt tgtttgataa ttgattaaca g                       101
```

<210> SEQ ID NO 20
<211> LENGTH: 1221
<212> TYPE: DNA
<213> ORGANISM: Helianthus annuus
<220> FEATURE:
<221> NAME/KEY: misc_feature
<222> LOCATION: (1)..(1221)
<223> OTHER INFORMATION: Hahb-4 promoter small allele

<400> SEQUENCE: 20

```
gatccaattg gaccacctgg cacatcgtat cttatctctt ttgtcgtttc caacacacca    60
caacacacct acaaacgtgt caattcacac ttcaccaatt tcatttcctt ttagtcaatc   120
atattaaaag tagtagcccc cacccccatt tgttacctac catttcccac tttaataatc   180
acccacgcta tgtccacttg tactttttgtt tgcacacaac tcttcccata aaatatcaaa   240
ccaaattttt tttagtggaa aacaaattcc ccaaatagaa tactaacgaa attcatcgca   300
```

```
tcagaataca ctcatctctg aacagtggcg aagcttgacg ttttcgacgg ggggtcggaa      360
aacgtatgta cccgaaattt ctatagaatc gggggtcga aaacgtatat acccaaaatt       420
tctatacgaa aactacatat ataacactac tgagcaaaaa gttcgggggt tcgggcgccc     480
ctcccggccc cttcaaagct tcgccaatgt ctctgaaccg aagaaaaccc tcactcgtct     540
actagccaat gaatcctcac cagggaaacc ctcactcgtc ttactggact attggcgctt    600
ccaaatggac tacttgcgaa attcaccaca tcgggataca ctcgtctact gcggtgaggt    660
aaaacccgct tggctcaagg atcgaactag cgattgctgc ctactcgcct aatctcccat    720
catcaacagg tgccgccgaa acaaaatgct ggggcggga gttgaaccta ggtccagtga    780
cgcacccatg aattttttt ctagggatgc gaacgagtgg tttaaccata cttttaagag     840
gtgcgatcgg aaattttacc tataaaatac actaaaaaag ttccaagggt ccacccaccc    900
cttaacctaa gtccgccttt gtctggatca cgtgaaacat caggtctctc ccttaccagt    960
ccagctacga ctcattgaca aaatatcaaa accatatgat tttgagtttt atctcaaccg    1020
aaagtgacat catgacagag aatcgacata accaaaacgt gtaaacgtac aactcaccat    1080
tgcgttgaaa aggacaaaac aggtaggatt cttgtcaaat tcaacgcgta cacctgtgct    1140
tcatctaaac cccatacttt aagaaccttt ataaagacca ctcactatat atacacatat    1200
ataatatcac ttatcaaacc c                                              1221

<210> SEQ ID NO 21
<211> LENGTH: 1015
<212> TYPE: DNA
<213> ORGANISM: Helianthus annuus
<220> FEATURE:
<221> NAME/KEY: misc_feature
<222> LOCATION: (1)..(1015)
<223> OTHER INFORMATION: Hahb-4 promoter large allele

<400> SEQUENCE: 21
gatccaattg gaccacctgg cacatcgtat cttatctctt ttgtcgtttc caacacacca     60
caacacacct acaaacgtgt caattcacac ttcaccaatt tcatttcctt ttagtcaatc    120
atattaaaag tagtagcccc cacccccatt tgttacctac catttcccac tttaataatc    180
acccacgcta tgtccacttg tacttttgtt tgcacacaac tcttcccata aaatatcaaa    240
ccaaattttt tttaatggaa aacaaatact tcaaatgcac tattggtgaa attcaccaca    300
tcagaataca cccgtctcta ctcatctact ggccaacgaa tcttcacggg ggaaaccctc    360
actcgtctac tgggactact ggcgcttcaa aatggactac tgacaaaatt caccacatcg    420
ggatacactt gtctactgcg gtgaggtaaa atccgccgct cagctcaatg atcgaactag    480
cgatcgccac ccactcacct tgtctcccat catcaccagg tgccgccaaa acaaaatgtt    540 ggggcggga attgaaccta ggtccagtgg cgcacccatg aattttttt ctagggatgc     600 gaacgagtga tttaaccata cttttaagag gtgcgatcgg aaattttacc tataaaatat    660
actaaaaaaa tttcaagggt ccgcccaccc accccttaac ctaagtccgc ctctgcctgg   720
atcacgtgaa acatcaggtc tctctcttac cagttcacct acaactcatt gacaaaatat    780
caaaaccata tgattttgag ttttatctca accgaaagtg acatcatgac agagaatcga    840
cataaccaaa acgtgtaaac gtacaactca ccattgcgtt gaaaaggaca aaacaggtag    900
gattcttgtc aaattcaacg cgtacacctg tgcttcatct aaacccata ctttaagaac    960 ctttataaag accactcact atatacac atatataata tcacttatca aaccc          1015
```

<210> SEQ ID NO 22
<211> LENGTH: 30
<212> TYPE: DNA
<213> ORGANISM: Artificial
<220> FEATURE:
<223> OTHER INFORMATION: primer

<400> SEQUENCE: 22
atgtctcttc aacaagtaac aaccaccagg                              30

<210> SEQ ID NO 23
<211> LENGTH: 30
<212> TYPE: DNA
<213> ORGANISM: Artificial
<220> FEATURE:
<223> OTHER INFORMATION: primer

<400> SEQUENCE: 23
gccgagctct tagaactcca accactttg                               30

<210> SEQ ID NO 24
<211> LENGTH: 31
<212> TYPE: DNA
<213> ORGANISM: Artificial
<220> FEATURE:
<223> OTHER INFORMATION: primer

<400> SEQUENCE: 24
ttagaactcc caccactttt gaaggtctgg c                            31

<210> SEQ ID NO 25
<211> LENGTH: 34
<212> TYPE: DNA
<213> ORGANISM: Artificial
<220> FEATURE:
<223> OTHER INFORMATION: primer

<400> SEQUENCE: 25
cggttttgcg taccttgaag aaggaaacag tttg                         34

<210> SEQ ID NO 26
<211> LENGTH: 30
<212> TYPE: DNA
<213> ORGANISM: Artificial
<220> FEATURE:
<223> OTHER INFORMATION: primer

<400> SEQUENCE: 26
gcgggatcca ccatgtctct tcaacaagta                              30

<210> SEQ ID NO 27
<211> LENGTH: 32
<212> TYPE: DNA
<213> ORGANISM: Artificial
<220> FEATURE:
<223> OTHER INFORMATION: primer

<400> SEQUENCE: 27
gtttccttct tcaaggtacg caaaaccgtc gc                           32

<210> SEQ ID NO 28
<211> LENGTH: 19
<212> TYPE: DNA
<213> ORGANISM: Artificial
<220> FEATURE:
<223> OTHER INFORMATION: primer

<400> SEQUENCE: 28
acctggcaca tcgtatctt                                                    19

<210> SEQ ID NO 29
<211> LENGTH: 18
<212> TYPE: DNA
<213> ORGANISM: Artificial
<220> FEATURE:
<223> OTHER INFORMATION: primer +300

<400> SEQUENCE: 29
caaaggcgga cttaggtt                                                     18

<210> SEQ ID NO 30
<211> LENGTH: 19
<212> TYPE: DNA
<213> ORGANISM: Artificial
<220> FEATURE:
<223> OTHER INFORMATION: primer IPCR4

<400> SEQUENCE: 30
gatgcgaacg agtggttta                                                    19

<210> SEQ ID NO 31
<211> LENGTH: 17
<212> TYPE: DNA
<213> ORGANISM: Artificial
<220> FEATURE:
<223> OTHER INFORMATION: primer H4SCT R

<400> SEQUENCE: 31
ttcttcaccg ctgccac                                                      17

<210> SEQ ID NO 32
<211> LENGTH: 23
<212> TYPE: DNA
<213> ORGANISM: Artificial
<220> FEATURE:
<223> OTHER INFORMATION: primer TRANSF1Xba

<400> SEQUENCE: 32
atgtctcttc aacaagtacc cac                                               23

<210> SEQ ID NO 33
<211> LENGTH: 22
<212> TYPE: DNA
<213> ORGANISM: Artificial
<220> FEATURE:
<223> OTHER INFORMATION: primer NOS121 R

<400> SEQUENCE: 33
gaattcccga tctagtaaca ta                                                22

<210> SEQ ID NO 34
<211> LENGTH: 20
<212> TYPE: DNA
<213> ORGANISM: Artificial
<220> FEATURE:
<223> OTHER INFORMATION: primer 35S Prim F

<400> SEQUENCE: 34
tgacgcacaa tcccactatc                                                   20

<210> SEQ ID NO 35
<211> LENGTH: 22

```
<212> TYPE: DNA
<213> ORGANISM: Artificial
<220> FEATURE:
<223> OTHER INFORMATION: primer NOS121 R

<400> SEQUENCE: 35
gaattcccga tctagtaaca ta                                              22

<210> SEQ ID NO 36
<211> LENGTH: 24
<212> TYPE: DNA
<213> ORGANISM: Artificial
<220> FEATURE:
<223> OTHER INFORMATION: artificial oligonucleotide

<400> SEQUENCE: 36
aattcagatc tcaataattg agag                                            24

<210> SEQ ID NO 37
<211> LENGTH: 25
<212> TYPE: DNA
<213> ORGANISM: Artificial
<220> FEATURE:
<223> OTHER INFORMATION: artificial oligonucleotide

<400> SEQUENCE: 37
gatcctctca attattagag atctg                                           25

<210> SEQ ID NO 38
<211> LENGTH: 181
<212> TYPE: PRT
<213> ORGANISM: Helianthus annuus
<220> FEATURE:
<221> NAME/KEY: MISC_FEATURE
<222> LOCATION: (1)..(180)
<223> OTHER INFORMATION: HaHB4.3

<400> SEQUENCE: 38
```

Met Ser Leu Gln Gln Val Pro Thr Ser Glu Thr Thr Ser Arg Lys Asn
1               5                   10                  15

Arg Asn Glu Gly Arg Lys Arg Phe Thr Asp Lys Gln Ile Ser Phe Leu
            20                  25                  30

Glu Tyr Met Phe Glu Thr Gln Ser Arg Pro Glu Leu Arg Met Lys His
        35                  40                  45

Gln Leu Ala His Lys Leu Gly Leu His Pro Arg Gln Val Ala Ile Trp
    50                  55                  60

Phe Gln Asn Lys Arg Ala Arg Ser Lys Ser Arg Gln Ile Glu Gln Glu
65                  70                  75                  80

Tyr Asn Ala Leu Lys His Asn Tyr Glu Thr Leu Ala Ser Lys Ser Glu
                85                  90                  95

Ser Leu Lys Lys Glu Asn Gln Ala Leu Leu Asn Gln Leu Glu Val Leu
            100                 105                 110

Arg Asn Val Ala Glu Lys His Gln Glu Lys Thr Ser Ser Ser Gly Ser
        115                 120                 125

Gly Glu Glu Ser Asp Asp Arg Phe Thr Asn Ser Pro Asp Val Met Phe
    130                 135                 140

Gly Gln Trp Met Asn Val Pro Phe Cys Asp Gly Phe Ala Tyr Phe Glu
145                 150                 155                 160

Glu Gly Asn Ser Leu Leu Glu Ile Glu Glu Gln Leu Pro Asp Leu Gln
                165                 170                 175

Lys Trp Trp Glu Phe
            180

```
                                180

<210> SEQ ID NO 39
<211> LENGTH: 181
<212> TYPE: PRT
<213> ORGANISM: Helianthus annuus
<220> FEATURE:
<221> NAME/KEY: MISC_FEATURE
<222> LOCATION: (1)..(181)
<223> OTHER INFORMATION: HaHB4.4

<400> SEQUENCE: 39

Met Ser Leu Gln Gln Val Pro Thr Thr Glu Thr Thr Thr Arg Lys Asn
1               5                   10                  15

Arg Asn Glu Gly Arg Lys Arg Phe Thr Asp Lys Gln Ile Ser Phe Leu
                20                  25                  30

Glu Tyr Met Phe Glu Thr Gln Ser Arg Pro Glu Leu Arg Met Lys His
            35                  40                  45

Gln Leu Ala His Lys Leu Gly Leu His Pro Arg Gln Val Ala Ile Trp
        50                  55                  60

Phe Gln Asn Lys Arg Ala Arg Ser Lys Ser Arg Gln Ile Glu Gln Glu
65                  70                  75                  80

Tyr Asn Ala Leu Lys His Asn Tyr Glu Thr Leu Ala Ser Lys Ser Glu
                85                  90                  95

Ser Leu Lys Lys Glu Asn Gln Ala Leu Leu Asn Gln Leu Glu Val Leu
                100                 105                 110

Arg Asn Val Ala Glu Lys His Gln Glu Lys Thr Ser Ser Ser Gly Ser
            115                 120                 125

Gly Glu Glu Ser Asp Asp Arg Phe Thr Asn Ser Pro Asp Val Met Phe
        130                 135                 140

Gly Gln Trp Met Asn Val Pro Phe Cys Asp Gly Phe Ala Tyr Phe Glu
145                 150                 155                 160

Glu Gly Asn Ser Leu Leu Glu Ile Glu Glu Gln Leu Pro Asp Leu Gln
                165                 170                 175

Lys Trp Trp Glu Phe
                180
```